United States Patent
Dousson et al.

(10) Patent No.: US 11,730,748 B2
(45) Date of Patent: Aug. 22, 2023

(54) CYCLIC PHOSPHATE SUBSTITUTED NUCLEOSIDE DERIVATIVES FOR THE TREATMENT OF LIVER DISEASES

(71) Applicant: MSD International GMBH, Lucerne (CH)

(72) Inventors: Cyril B. Dousson, Canet (FR); David Dukhan, Montpellier (FR); Christophe C. Parsy, Jacou (FR); Stephane L. Bogen, Somerset, NJ (US)

(73) Assignee: MSD International GMBH, Lucerne (CH)

( * ) Notice: Subject to any disclaimer, the term of this patent is extended or adjusted under 35 U.S.C. 154(b) by 157 days.

(21) Appl. No.: 17/103,391

(22) Filed: Nov. 24, 2020

(65) Prior Publication Data

US 2021/0205339 A1     Jul. 8, 2021

Related U.S. Application Data

(63) Continuation of application No. 16/462,779, filed as application No. PCT/EP2017/079346 on Nov. 15, 2017, now abandoned.

(30) Foreign Application Priority Data

Nov. 21, 2016 (EP) .................................... 16306526

(51) Int. Cl.
| | |
|---|---|
| A61K 31/675 | (2006.01) |
| A61P 1/16 | (2006.01) |
| A61P 31/12 | (2006.01) |
| C07F 9/6558 | (2006.01) |
| C07F 9/6561 | (2006.01) |

(52) U.S. Cl.
CPC .............. *A61K 31/675* (2013.01); *A61P 1/16* (2018.01); *C07F 9/65586* (2013.01); *C07F 9/65616* (2013.01)

(58) Field of Classification Search
CPC .......... A61K 31/675; A61P 1/16; A61P 31/12; C07F 9/6552; C07F 9/65522; C07F 9/65586; C07F 9/65616; C07F 9/65744
See application file for complete search history.

(56) References Cited

U.S. PATENT DOCUMENTS

| | | | |
|---|---|---|---|
| 5,712,274 | A | 1/1998 | Sueoka et al. |
| 7,488,802 | B2 | 2/2009 | Collins et al. |
| 7,521,051 | B2 | 4/2009 | Collins et al. |
| 7,879,815 | B2 | 2/2011 | MacCoss et al. |
| 8,008,449 | B2 | 8/2011 | Korman et al. |
| 8,168,757 | B2 | 5/2012 | Finnefroch et al. |
| 8,354,509 | B2 | 1/2013 | Carven et al. |
| 8,383,796 | B2 | 2/2013 | Korman et al. |
| 8,476,260 | B2 | 7/2013 | Miyoshi et al. |
| 9,296,778 | B2 | 3/2016 | Parsy et al. |
| 9,439,962 | B2 | 9/2016 | Honjo et al. |
| 10,202,411 | B2 | 2/2019 | Dukhan et al. |
| 10,899,788 | B2 * | 1/2021 | Bogen .................. C07H 19/213 |
| 2008/0025979 | A1 | 1/2008 | Honjo et al. |
| 2010/0286127 | A1 | 11/2010 | Miyoshi et al. |
| 2011/0271358 | A1 | 11/2011 | Freeman et al. |
| 2014/0099283 | A1 | 4/2014 | Gosselin et al. |
| 2022/0040214 | A1 * | 2/2022 | Bogen ..................... A61P 31/14 |

FOREIGN PATENT DOCUMENTS

| | | |
|---|---|---|
| EP | 661284 A1 | 7/1995 |
| WO | 1994006802 A1 | 3/1994 |
| WO | 2001002369 A2 | 1/2001 |
| WO | 2002010192 A2 | 2/2002 |
| WO | 2002068470 A2 | 9/2002 |
| WO | 2004004771 A1 | 1/2004 |
| WO | 2004056875 A1 | 7/2004 |
| WO | 2004072286 A1 | 8/2004 |
| WO | 2005003047 A1 | 1/2005 |
| WO | 2008082602 A2 | 7/2008 |
| WO | 2009084693 A1 | 7/2009 |
| WO | 2010027827 A2 | 3/2010 |
| WO | 2010075517 A2 | 7/2010 |
| WO | 2010075549 A2 | 7/2010 |
| WO | 2010077634 A1 | 7/2010 |
| WO | 2010081628 A1 | 7/2010 |
| WO | 2011066342 A2 | 6/2011 |
| WO | 2013019906 A1 | 2/2013 |
| WO | 2013177195 A1 | 11/2013 |

(Continued)

OTHER PUBLICATIONS

Berge, S.M., et al.,, "Pharmaceutical Salts", J. Pharm. Sci, 1977, pp. 1-19, vol. 66, No. 1.

(Continued)

*Primary Examiner* — Brenda L Coleman
(74) *Attorney, Agent, or Firm* — Jeffrey P. Bergman; Catherine D. Fitch

(57) ABSTRACT

The present invention relates to Compounds of Formula (I) or Formula (II):

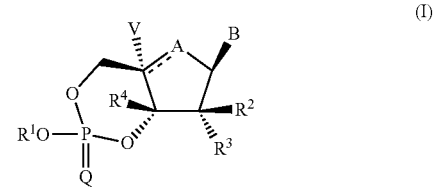

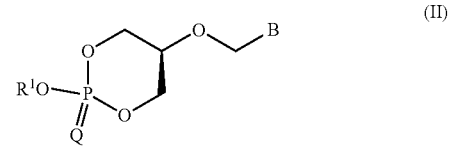

or a pharmaceutically acceptable salt, solvate or enantiomer thereof, wherein A, B, $R^1$, $R^2$, $R^3$, $R^4$, Q and V are as defined herein. The present invention also relates to pharmaceutical compositions comprising a Compound of Formula (I) or Formula (II) and to their use in therapy.

11 Claims, No Drawings

(56) References Cited

FOREIGN PATENT DOCUMENTS

| WO | 2014058801 A1 | 4/2014 |
| WO | 2015161137 A1 | 10/2015 |

OTHER PUBLICATIONS

Bingham, A.L., et al.,, "Over One Hundred Solvates of sulfathiazole", Chem. Commun., 2001, pp. 603-604.

Block, Timothy M., Molecular viral oncology of hepatocellular carcinoma, Oncogene, 2003, 5093-5107, 22.

Bobeck, et al.,, "Advances In Nucleoside Monophosphate Prodrugs As Anti-HCV Agents", Antiviral Therapy, 2010, pp. 935-950, vol. 15.

Caira, M.R., et al.,, "Preparation and Crystal Characterization of a Polymorph, a Monohydrate, and an Ethyl Acetate Solvate of the Antifungal Fluconazole", J. Pharmaceutical Sci., 2004, pp. 601-611, vol. 93, No. 3.

Erion, M., "Microsomes and Drug Oxidations", Proceedings of the International Symposium, 17th, 2008, pp. 7-12, Saratoga Sprints, NY, US.

Furman, et al.,, "Nucleoside Analog Inhibitors Of Hepatitis C Viral Replication: Recent Advances, Challenges And Trends", Future Medicinal Chemistry, 2009, pp. 1429-1452, vol. 1.

Gould, Salt Selections for Basic Drugs, Intl. J. Pharmaceutics, 1986, pp. 201-217, vol. 33.

Green & Wuts, Protective Groups in Organic Synthesis, 2nd Edition, 1991, -, -.

Higuchi, T., et al., "Pro-drugs as Novel Delivery Systems", A.C.S. Symposium Series, 1987, 14, pp. 1-6.

Mehellou, Y., "Phosphoramidate Prodrugs Deliver with Potency Against Hepatitis C Virus", Chem. Med. Chem., 2010, pp. 1841-1842, vol. 5.

Roche, E.B., Bioreversible Carriers in Drug Design, Theory and Application, Pergamon Press, 1987.

Stahl et al., Aminoquinazoline Compounds as A2A Antagonist, Handbook of Pharmaceutical Salts Properties, Selection, and Use, 2002, 330-331.

Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No., US.

\* cited by examiner

CYCLIC PHOSPHATE SUBSTITUTED NUCLEOSIDE DERIVATIVES FOR THE TREATMENT OF LIVER DISEASES

CROSS-REFERENCE TO RELATED APPLICATIONS

This application is a continuation of U.S. Ser. No. 16/462,779, filed May 21, 2019, currently pending, which is the national stage application under 35 U.S.C. 371 of International Patent Application No. PCT/EP17/079346, filed Nov. 15, 2017, which claims priority to European Patent Application No. 16306526.1, filed Nov. 21, 2016. Each of the aforementioned applications is incorporated by reference in its entirety.

FIELD OF THE INVENTION

The present invention relates to compounds of Formula (I) or Formula (II), compositions comprising the compounds of Formula (I) or Formula (II) and the compounds of Formula (I) or Formula (II) for use in treating or preventing liver diseases, such as cancer, Hepatitis B virus infection or Ebolavirus infection in a patient.

BACKGROUND OF THE INVENTION

Cancer is a disease characterised primarily by an uncontrolled division of abnormal cells derived from a given normal tissue and the invasion of adjacent tissues by these malignant cells. Blood or lymphatic transportation can spread cancer cells to other parts of the body leading to regional lymph nodes and to distant sites (metastasis). Cancer is a complex, multistep process that begins with minor preneoplastic changes, which may under certain conditions progress to neoplasia. There are more than 100 different types of cancer, which can be grouped into broader categories. The main categories include: carcinoma, sarcoma, leukemia, lymphoma and myeloma, and central nervous system cancers. The incidence of cancer continues to climb as the general population ages, as new cancers develop, and as susceptible populations (e.g., people infected with AIDS or excessively exposed to sunlight) grow.

Primary liver cancer is one of the most common forms of cancer in the world. Hepatocellular carcinoma, also known as malignant hepatoma, is the most common form of primary liver cancer, and develops within the hepatocyte. Hepatocellular carcinoma occurs mostly in men and patients that suffer from cirrhosis. It has been the third leading cause of cancer deaths worldwide (Block T. M. et al., 2003, *Oncogene* 22:5093-5107). Many patients with hepatocellular carcinoma remain asymptomatic until the disease is in its advanced stages, resulting in ineffective treatment and poor prognosis; the majority of unresectable hepatocellular carcinoma patients die within one year.

Treatment options for hepatocellular carcinoma have been limited, especially in the case of advanced or recurrent hepatocellular carcinoma. Surgery and radiation therapy are options for early stage liver cancer, but not very effective for advanced or recurrent hepatocellular carcinoma. Systematic chemotherapies have not been particularly effective, and there are a very limited number of drugs available for use. The recently approved kinase inhibitor sorafenib has been shown to be effective in treating hepatocellular carcinoma. However, it can slow or stop advanced liver cancer from progressing for only a few months longer than without treatment.

Liver cancers which can be treated include primary and secondary liver cancers. In particular cases, the liver cancer is hepatocellular carcinoma, cholangiocarcinoma, or biliary tract cancer. In particular cases, the liver cancer is a metastasis in the liver originated from other cancers (such as colon cancer, pancreatic cancer, etc.). In certain embodiments, the compounds described herein can be used to treat cancers such as breast cancer, ovarian cancer, lung cancer, pancreatic cancer and leukemic cancer Hepatitis B virus (HBV) infection is a major health problem that can lead to chronic liver disease, such as cirrhosis and hepatocellular carcinoma, in a substantial number of infected individuals. Although most individuals seem to resolve the infection following acute symptoms, approximately 30% of cases become chronic. According to recent estimates around five percent of the world's population have chronic hepatitis B, leading to half a million to one million deaths per year.

HBV is a small DNA virus that is considered to be the prototypical member of the hepadnaviridae. HBV is an enveloped virus with an unusual mode of replication, centering on the establishment of a covalently closed circular DNA (cccDNA) copy of its genome in the host cell nucleus. The episomal form is established from conversion of the partially double stranded circular DNA (relaxed circular, or rcDNA) genome upon initial infection and functions as the template for all HBV mRNAs. Unlike the mechanisms of most other DNA viruses, HBV cccDNA replicates through retrotranscription of a 1.1 genome unit-length RNA copy (pregenomic, or pgDNA) which is originally transcribed from the cccDNA template and which is acted upon by a virus encoded polymerase to yield progeny rcDNA. HBV DNA synthesis is coupled to assembly of its capsid and most copies of the encapsidated genome then efficiently associate with the envelope proteins for viron assembly and secretion; a minority of these genomes are shunted to the nucleus where they are converted to ccDNA, thus amplifying levels of the episome. HBV is classified into eight genotypes (A-H)

Although the viral polymerase and surface antigen (HBsAg) perform very different functions, both are essential proteins for the virus to complete its life cycle and be infectious. That is HBV lacking HBsAg is completely defective and cannot infect or cause infection. HBsAg is needed to protect the virus nucleocapsid, to begin the infectious cycle and to mediate morphogenesis and secretion of newly forming virus from the infected cells.

HBV is transmitted parenterally by contaminated blood and blood products, contaminated needles, or sexually and vertically from infected mothers or carrier mothers to their off-spring. People who are chronically affected with HBV are usually characterised by readily detectable levels of circulating antibody specific to the viral capsid (HBc), with little, if any, detectable levels of antibody to HBsAg. There is some evidence that chronic carriers do produce antibodies to HBsAg, but these antibodies are complexed with the circulating HBsAg, which can be present in milligram per milliliter amounts in a chronic carrier's circulation.

As the only enzyme encoded by HBV, the polymerase has been well exploited as a target for antiviral drug development, with several nucleoside polymerase inhibitors approved for drug use and others in development. Mutations in the primary sequence of the polymerase that confer resistance to lamivudine and adefovir have been identified clinically, and underly a rebound of serum virus titers that 70% of treated patients experience within three years of starting lamivudine therapy. Although resistance to telbivudine, adefovir and entecavir occurs more rarely, it has been recorded. α-interferon is the other major therapy available for treatment of hepatitis B, but is limited by poor long-term response and debilitating side-effects. Despite the availability of an effective vaccine, immunoglobulin therapy, interferon and antiviral drugs, there is a need for improved therapeutic agents that effectively combat chronic HBV infection.

The viruses of the Filoviridae family are enveloped negative sense, single-stranded, linear RNA viruses. Three genera within the Filoviridae family are Ebolavirus, Marburgvirus and 'Cuevavirus' (tentative). The five recognized species of Ebolavirus are Ebola virus (EBOV), Reston ebolavirus (REBOV), Sudan ebolavirus (SEBOV), Tai Forest ebolavirus (TAFV) and Bundibugyo ebolavirus (BEBOV). Ebolavirus and Marburgvirus are both highly infectious and contagious. Both viruses are transmitted by direct contact with the blood, body fluids and/or tissues of the infected persons. Ebolavirus and Marburgvirus can also be transmitted by handling sick or dead infected wild animals. Ebola hemorrhagic fever (EHF) is caused by an Ebolavirus infection. Marburg virus disease (MVD) is a human disease caused by Marburgvirus and causes Marburgvirus hemorrhagic fever (MHF). The primary organs infected by Ebolavirus have been shown to be the liver and the spleen as reported in *Rev. Fr. Histotechnol.*, 2012, vol. 25 no. 1, pages 65-80.

There remains a need for further therapies for the treatment of liver diseases, such as cancer or HBV infection or Ebolavirus infection which are safe and effective.

SUMMARY OF THE INVENTION

In one aspect, the present invention provides a compound according to Formula (I) or Formula (II):

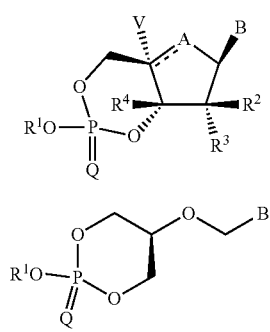

or a pharmaceutically acceptable salt, solvate or enantiomer thereof, wherein:

A is selected from O, S, $CH_2$, CF and C=$CH_2$, with the proviso that if $R^2$ is OH and $R^3$, $R^4$ and V are hydrogen, then A is other than S; and if A is CF or C=$CH_2$, then V is absent;

B is selected from the following groups:

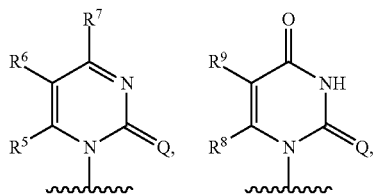

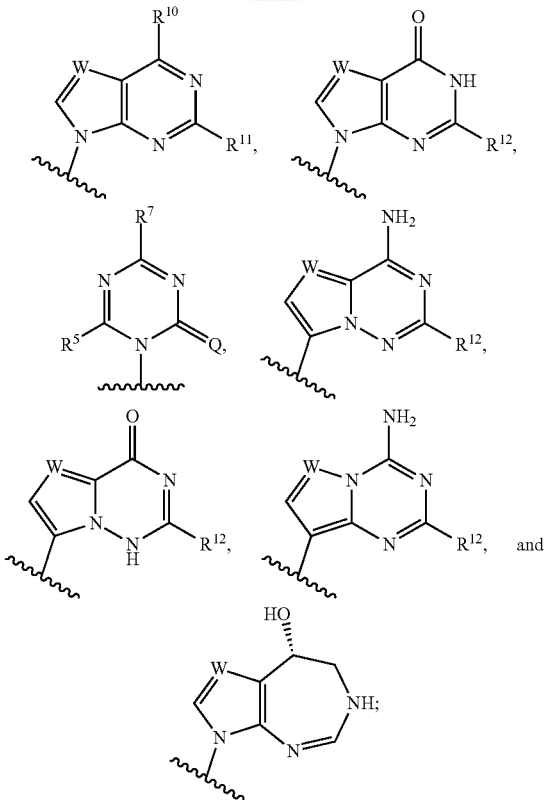

Q is O or S;

V is hydrogen, halogen, —$N(R^{13})_2$, —$OR^{13}$, alkyl, alkenyl, alkynyl, haloalkyl, $N_3$ or CN;

W is N, CH or CF;

$R^1$ is —$CH_2$—X—Y—$R^{16}$;

X is —$C(R^{14})_2$;

Y is —$C(R^{15})_2$ or $C_3$-$C_6$cycloalkylene;

$R^2$ is hydrogen, fluoro, chloro, —$OR^{13}$, —CN, —$N(R^{13})_2$, $N_3$, $C_1$-$C_3$alkyl, $C_1$-$C_3$haloalkyl, $C_2$-$C_6$alkenyl or $C_2$-$C_3$alkynyl;

$R^3$ is hydrogen, $C_1$-$C_6$alkyl, $C_2$-$C_6$alkenyl, $C_2$-$C_6$alkynyl, $C_1$-$C_6$haloalkyl, —$OR^{13}$, fluoro, chloro, $N_3$, —CN or —$N(R^{13})_2$ with the proviso that if $R^2$ is fluoro or chloro, then $R^3$ is other than fluoro or chloro;

$R^4$ is hydrogen, $C_1$-$C_6$alkyl, $C_2$-$C_6$alkenyl, $C_2$-$C_6$alkynyl, $C_1$-$C_6$haloalkyl, —$OR^{13}$, fluoro, chloro, $N_3$, —CN or —$N(R^{13})_2$;

$R^5$, $R^6$, $R^8$ and $R^9$ are each independently selected from hydrogen, $C_1$-$C_6$alkyl, $C_1$-$C_6$haloalkyl, $C_1$-$C_6$hydroxyalkyl, halogen, —$OR^{18}$, —$SR^{18}$ and —$N(R^{18})_2$; $C_1$-$C_{10}$ alkyl or —$COOR^7$;

$R^7$, $R^{10}$, $R^{11}$ and $R^{12}$ are each independently selected from hydrogen, $C_1$-$C_6$alkyl, $C_2$-$C_6$ alkenyl, $C_2$-$C_6$alkynyl, $C_3$-$C_7$cycloalkyl, $C_5$-$C_6$heteroary, $C_9$-$C_{10}$heteroaryl, halogen, —$OR^{18}$, —$SR^{18}$, —$S(O)R^{18}$, —$S(O)_2R^{18}$, —$S(O)_2N(R^8)_2$, —NHC(O)$OR^{18}$, —NHC(O)$N(R^8)_2$, $C_1$-$C_6$haloalkyl, $C_1$-$C_6$hydroxyalkyl, —$O(C_1$-$C_6$haloalkyl), —CN, —$NO_2$, —$N(R^{18})_2$, —NH($C_1$-$C_6$ alkylene)-($C_5$-$C_6$heteroaryl), —NH($C_1$-$C_6$ alkylene)-($C_9$-$C_{10}$heteroaryl), —$C(O)R^{18}$, —$C(O)OR^{18}$, —$C(O)N(R^{18})_2$ and —NHC(O)$R^{18}$, wherein said $C_2$-$C_6$alkenyl group and said $C_2$-$C_6$alkynyl group are optionally substituted with one or more halogen;

each occurrence of $R^{13}$ is independently selected from hydrogen, $C_1$-$C_6$ alkyl, —$C(O)R^{18}$ or —$C(O)OR^{18}$;

$R^{14}$ is hydrogen, halogen, $C_1$-$C_6$alkyl, $C_1$-$C_6$haloalkyl, $C_1$-$C_6$hydroxyalkyl, $C_6$-$C_{10}$aryl-, $OR^{17}$, —OC(O)$R^{17}$, —N($R^{12}$)C(O)O$R^{17}$ or —C(O)O$R^{17}$;

each occurrence of $R^{15}$ is independently selected from hydrogen, halogen, $C_1$-$C_6$ alkyl, $C_1$-$C_6$ haloalkyl, $C_1$-$C_6$ hydroxyalkyl, $C_6$-$C_{10}$aryl-, $OR^{17}$, —OC(O)$R^{17}$, —N($R^{12}$)C(O)O$R^{17}$ and —C(O)O$R^{17}$ or both $R^{15}$ groups together with the carbon atom to which they are attached can join to form a 3- to 6-membered spirocyclic cycloalkyl group;

$R^{16}$ is —C(O)O$R^{17}$;

each occurrence of $R^{17}$ is independently selected from hydrogen, halogen, $C_1$-$C_6$alkyl, $C_3$-$C_7$cycloalkyl and $C_6$-$C_{10}$aryl;

each occurrence of $R^{18}$ is independently selected from hydrogen, $C_1$-$C_{15}$alkyl, $C_1$-$C_6$haloalkyl, $C_1$-$C_6$hydroxyalkyl, —($C_1$-$C_3$alkylene)$_m$-($C_3$-$C_7$cycloalkyl), —($C_1$-$C_3$alkylene)$_m$-($C_6$-$C_{10}$aryl), —($C_1$-$C_3$alkylene)$_m$-($C_4$-$C_7$heterocycloalkyl), —($C_1$-$C_3$alkylene)$_m$-($C_5$-$C_6$heteroaryl) and —($C_1$-$C_3$alkylene)$_m$-($C_9$-$C_{10}$heteroaryl) and each occurrence of m is independently 0 or 1;

or the compound

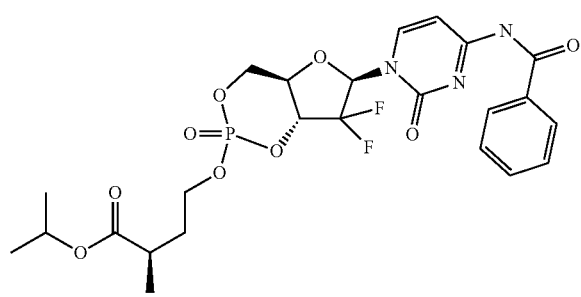

or a pharmaceutically acceptable salt or solvate thereof.

In a further aspect, the present invention provides a pharmaceutical composition comprising a compound according to Formula (I) or Formula (II) or a pharmaceutically acceptable salt, solvate or enantiomer thereof, and a pharmaceutically acceptable carrier or diluent.

The compounds of Formula (I) or Formula (II) or pharmaceutically acceptable salts, solvates or enantiomers thereof are useful in therapy. In particular, the compounds of Formula (I) or Formula (II) or pharmaceutically acceptable salts, solvates or enantiomers thereof are useful in the treatment or prevention of liver diseases in a patient. As such, compounds of Formula (I) or Formula (II) or pharmaceutically acceptable salts, solvates or enantiomers thereof can be useful, for example, for treating or preventing cancer in a patient.

Compounds of Formula (I) or Formula (II) or pharmaceutically acceptable salts, solvates or enantiomers thereof can also be useful for inhibiting HBV replication or replicon activity and for treating or preventing HBV infection in a patient. Compounds of Formula (I) or Formula (II) or pharmaceutically acceptable salts, solvates or enantiomers thereof can also be useful for treating or preventing Ebolavirus infection in a patient.

Accordingly, the present invention provides a compound of Formula (I) or Formula (II) or a pharmaceutically acceptable salt, solvate or enantiomer thereof for use in the treatment or prevention of liver diseases in a patient. The present invention further provides a compound of Formula (I) or Formula (II) or a pharmaceutically acceptable salt, solvate or enantiomer thereof for use in treating or preventing cancer in a patient. The present invention further provides a compound of Formula (I) or Formula (II) or a pharmaceutically acceptable salt, solvate or enantiomer thereof for use in treating or preventing HBV infection in a patient. The present invention further provides a compound of Formula (I) or Formula (II) or a pharmaceutically acceptable salt, solvate or enantiomer thereof for use in treating or preventing Ebolavirus infection in a patient.

The present invention further provides a combination comprising a compound of Formula (I) or Formula (II), or a pharmaceutically acceptable salt, solvate or enantiomer thereof and one, two, three or more other therapeutic agents.

The details of the invention are set forth in the accompanying detailed description below.

DETAILED DESCRIPTION OF THE INVENTION

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc.

As used herein, and throughout this disclosure, the following terms, unless otherwise indicated, shall be understood to have the following meanings:

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$alkyl), or from 1 to 3 carbon atoms ($C_1$-$C_3$alkyl). Examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. In one embodiment, an alkyl group is linear. In another embodiment, an alkyl group is branched. Unless otherwise indicated, an alkyl group is unsubstituted.

The term "$C_1$-$C_6$ alkoxy" as used herein, refers to a group having the formula —O—($C_1$-$C_6$alkyl), where the term "$C_1$-$C_6$ alkyl" is defined above herein.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from 2 to 12 carbon atoms. In another embodiment, an alkenyl group contains from 2 to 6 carbon atoms ($C_2$-$C_6$alkenyl). Examples of alkenyl groups include ethenyl, propenyl, n-butenyl, 3-methylbut-2-enyl, n-pentenyl, octenyl and decenyl. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from 2 to 6 carbon atoms ($C_2$-$C_6$alkynyl). In another embodiment, an alkynyl group contains from 2 to 3 carbon atoms ($C_2$-$C_3$alkynyl). Examples of alkynyl groups include ethynyl, propynyl, 2-butynyl and 3-methylbutynyl. Unless otherwise indicated, an alkynyl group is unsubstituted.

The term "alkylene," as used herein, refers to an alkyl group, as defined above, wherein one of the alkyl group's hydrogen atoms has been replaced with a bond. Examples of alkylene groups include —$CH_2$—, —$CH_2CH_2$—, —$CH_2CH_2CH_2$—, —$CH_2CH_2CH_2CH_2$—, —$CH(CH_3)$ $CH_2CH_2$—, —$CH(CH_3)$— and —$CH_2CH(CH_3)CH_2$—. In one embodiment, an alkylene group has from 1 to 6 carbon atoms ($C_1$-$C_6$alkylene). In another embodiment, an alkylene group has from 1 to 3 carbon atoms ($C_1$-$C_3$alkylene). In another embodiment, an alkylene group is branched. In another embodiment, an alkylene group is linear. In one embodiment, an alkylene group is —$CH_2$—.

The term "aryl," as used herein, refers to an aromatic monocyclic or multicyclic ring system comprising from about 6 to about 14 carbon atoms. In one embodiment, an aryl group contains from 6 to 10 carbon atoms ($C_6$-$C_{10}$aryl). In one embodiment, an aryl group can be optionally fused to a cycloalkyl or cycloalkanoyl group. Examples of aryl groups include phenyl and naphthyl. In one embodiment, an aryl group is phenyl. The term "aryloxy" as used herein, refers to a group having the formula —O-aryl, where the term "aryl" is defined above herein.

The term "cycloalkyl," as used herein, refers to a non-aromatic mono- or multicyclic ring system comprising from 3 to about 10 ring carbon atoms. In one embodiment, a cycloalkyl contains from 3 to 7 ring carbon atoms ($C_3$-$C_7$cycloalkyl). In another embodiment, a cycloalkyl contains from 5 to 6 ring atoms. Examples of monocyclic cycloalkyls include cyclopropyl, cyclobutyl, cyclopentyl, cyclohexyl, cycloheptyl and cyclooctyl. Examples of multicyclic cycloalkyls include 1-decalinyl, norbornyl and adamantyl. In one embodiment, a cycloalkyl group is unsubstituted. The term "3 to 6-membered cycloalkyl" refers to a cycloalkyl group having from 3 to 6 ring carbon atoms. A ring carbon atom of a cycloalkyl group may be functionalized as a carbonyl group. An illustrative example of such a cycloalkyl group (also referred to herein as a "cycloalkanoyl" group) includes cyclobutanoyl:

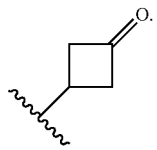

The term "cycloalkylene," as used herein, refers to a cycloalkyl group, as defined above, wherein one of the cycloalkyl group's hydrogen atoms has been replaced with a bond. Examples of cycloalkylene groups include cyclopropylene, cyclobutylene, cyclopentylene and cyclohexylene. In one embodiment, a cycloalkylene group has from 3 to 6 carbon atoms ($C_3$-$C_6$cycloalkylene).

The term "halogen," as used herein, means —F, —Cl, —Br or —I.

The term "haloalkyl," as used herein, refers to an alkyl group as defined above, wherein one or more of the alkyl group's hydrogen atoms have been replaced with a halogen. In one embodiment, a haloalkyl group has from 1 to 6 carbon atoms ($C_1$-$C_6$haloalkyl). In another embodiment, a haloalkyl group has from 1 to 3 carbon atoms ($C_1$-$C_3$haloalkyl). In another embodiment, a haloalkyl group is substituted with from 1 to 3 F atoms. Examples of haloalkyl groups include —$CH_2F$, —$CHF_2$, —$CF_3$, —$CH_2Cl$ and —$CCl_3$.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms ($C_1$-$C_6$hydroxyalkyl). Non-limiting examples of hydroxyalkyl groups include —$CH_2OH$, —$CH_2CH_2OH$, —$CH_2CH_2CH_2OH$ and —$CH_2CH(OH)$ $CH_3$.

The term "5 or 6-membered monocyclic heteroaryl," or $C_5$-$C_6$heteroaryl, as used herein, refers to an aromatic monocyclic ring system comprising 5 to 6 ring atoms, wherein from 1 to 4 of the ring atoms is independently O, N or S and the remaining ring atoms are carbon atoms. A 5 or 6-membered monocyclic heteroaryl group is joined via a ring carbon atom, and any nitrogen atom of a heteroaryl can be optionally oxidized to the corresponding N-oxide. Examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, imidazolyl, 1,2,4-triazinyl and the like, and all isomeric forms thereof.

The term "9 or 10-membered bicyclic heteroaryl," or $C_9$-$C_{10}$heteroaryl as used herein, refers to an aromatic bicyclic ring system comprising 9 to 10 ring atoms, wherein from 1 to 4 of the ring atoms is independently O, N or S and the remaining ring atoms are carbon atoms. A 9 or 10-membered bicyclic heteroaryl group is joined via a ring carbon atom, and any nitrogen atom of a heteroaryl can be optionally oxidized to the corresponding N-oxide. Examples of 9 or 10-membered bicyclic heteroaryls include imidazo[1,2-a]pyridinyl, imidazo[2,1-b]thiazolyl, benzofurazanyl, indolyl, azaindolyl, benzimidazolyl, benzothienyl, quinolinyl, benzimidazolyl, quinazolinyl, pyrrolopyridyl, imidazopyridyl, isoquinolinyl, benzoazaindolyl, benzothiazolyl, and the like, and all isomeric forms thereof.

The term "heterocycloalkyl," as used herein, refers to a non-aromatic monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from 3 to 7 ring atoms ($C_3$-$C_7$heterocycloalkyl). In another embodiment, a heterocycloalkyl group is monocyclic has from 4 to 7 ring atoms ($C_4$-$C_7$heterocycloalkyl). In another embodiment, a heterocycloalkyl group is bicyclic and has from 7 to 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. The nitrogen or sulfur atom of the heterocycloalkyl can be optionally oxidized to the corresponding N-oxide, S-oxide or S,S-dioxide. Examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Illustrative examples of a silyl-containing heterocycloalkyl group include:

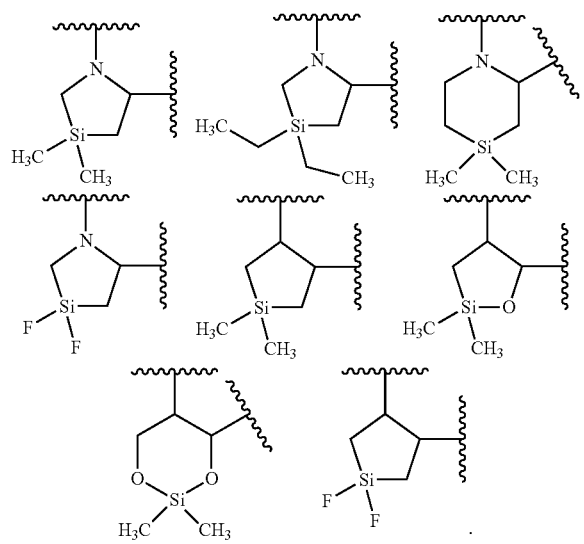

A ring carbon atom of a heterocycloalkyl group may be functionalized as a carbonyl group. An illustrative example of such a heterocycloalkyl group is:

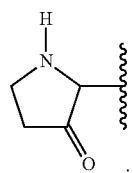

In one embodiment, a heterocycloalkyl group is a 5-membered monocyclic heterocycloalkyl. In another embodiment, a heterocycloalkyl group is a 6-membered monocyclic heterocycloalkyl. The term "3 to 6-membered monocyclic cycloalkyl" refers to a monocyclic heterocycloalkyl group having from 3 to 6 ring atoms. The term "4 to 6-membered monocyclic cycloalkyl" refers to a monocyclic heterocycloalkyl group having from 4 to 6 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "substituted", as used herein, means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

When referring to a substituent on a sugar ring of a nucleoside, the term "beta" refers to a substituent on the same side of the plane of the sugar ring as the 5' carbon and the term "alpha" refers to a substituent on the opposite side of the plane of the sugar ring from the 5' carbon. As shown below, substituent "A" is in the "alpha" position, and substituent "B" is in the "beta" position with respect to the 5' carbon.

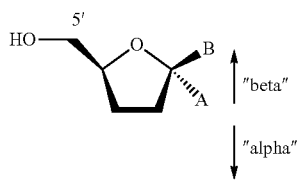

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York.

When any substituent or variable (e.g., alkyl, $R^6$, $R^a$, etc.) occurs more than one time in any constituent or in Formula (I) or Formula (II), its definition on each occurrence is independent of its definition at every other occurrence, unless otherwise indicated.

The term "composition," as used herein, is intended to encompass a product comprising the specified ingredients in the specified amounts, as well as any product which results directly from combination of the specified ingredients in the specified amounts.

$IC_{50}$, as used herein, refers to an amount, concentration or dosage of a particular test compound that achieves a 50% inhibition of a maximal response in an assay that measures such response.

The term "host," as used herein, refers to any unicellular or multicellular organism, including cell lines and animals, and in certain embodiments, a human. Alternatively, the host can be carrying a part of the Flaviviridae or Filovaridae viral genome, whose replication or function can be altered by the compounds of the present invention. The term "host" specifically includes infected cells, cells transfected with all or part of the Flaviviridae or Filovaridae genome and animals, in particular, primates (including chimpanzees) and humans. In most animal applications of the present invention, the host is a human patient. Veterinary applications, in certain indications, however, are clearly anticipated by the present invention (such as chimpanzees).

The terms "subject" and "patient," as used herein, are used interchangeably. The terms "subject" and "subjects" refer to a mammal including a non-primate (e.g., a cow, pig, horse, cat, dog, rat, and mouse) and a primate (e.g., a monkey such as a cynomolgous monkey, a chimpanzee and a human), and for example, a human. The subject may also be a farm animal (e.g., a horse, a cow, a pig, etc.) or a pet (e.g., a dog or a cat).

The terms "therapeutic agent" and "therapeutic agents," as used herein, refer to any agent(s) which can be used in the treatment or prevention of a disorder or one or more symptoms thereof. The term "therapeutic agent" includes a compound provided herein. In some cases, a therapeutic agent can be an agent which is known to be useful for, or has been or is currently being used for the treatment or prevention of a disorder or one or more symptoms thereof.

The term "effective amount," as used herein, refers to an amount of a compound of Formula (I) or Formula (II) and/or an additional therapeutic agent, or a composition thereof that is effective in producing the desired therapeutic, ameliorative, inhibitory or preventative effect when administered to a patient suffering from a viral infection or virus-related disorder. In the combination therapies of the present invention, an effective amount can refer to each individual agent or to the combination as a whole, wherein the amounts of all agents administered are together effective, but wherein the component agent of the combination may not be present individually in an effective amount. A "therapeutically effective amount" can vary depending on, inter alia, the compound, the disease and its severity, and the age, weight, etc., of the subject to be treated.

The term "treating" or "treatment" of any disease or disorder, as used herein, refers to ameliorating a disease or disorder that exists in a subject. In some cases, "treating" or "treatment" includes ameliorating at least one physical parameter, which may be indiscernible by the subject. In other cases, "treating" or "treatment" includes modulating the disease or disorder, either physically (e.g., stabilization of a discernible symptom) or physiologically (e.g., stabilization of a physical parameter) or both. In other cases, "treating" or "treatment" includes delaying the onset of the disease or disorder.

The term "preventing," as used herein with respect to a liver disease or disorder, refers to reducing the likelihood or severity of the liver disease or disorder.

The Compounds of Formula (I)

The present invention provides compounds of Formula (I), having the formula:

$$\text{(I)}$$

or a pharmaceutically acceptable salt, solvate or enantiomer thereof wherein A, B, $R^1$, $R^2$, $R^3$, $R^4$, Q and V are defined above for the compounds of Formula (I).

In one embodiment, A is O, S or $CH_2$, with the proviso that if $R^2$ is OH and $R^3$, $R^4$ and V are hydrogen, then A is other than S.

In another embodiment, A is O.

In another embodiment, A is S, with the proviso that if $R^2$ is OH, then $R^3$, $R^4$ and V cannot be hydrogen.

In another embodiment A, is CF or C=$CH_2$ and V is absent.

In another embodiment, A is CF and V is absent.

In another embodiment, A is C=$CH_2$ and V is absent.

In one embodiment, Q is O.

In another embodiment, Q is S.

In one embodiment, $R^1$ is —$CH_2$—$C(R^{14})_2$—$C(R^{15})_2$—$C(O)OR^{17}$, wherein $R^{14}$, $R^{15}$ and $R^{17}$ are as previously defined.

In one embodiment, $R^1$ is —$CH_2$—$C(R^{14})_2$—$C(R^{15})_2$—$C(O)OR^{17}$, wherein $R^{14}$, $R^{15}$ and $R^{17}$ are each independently selected from hydrogen and $C_1$-$C_6$alkyl.

In another embodiment, $R^1$ is —$CH_2$—$CH_2$—$C(R^{15})_2$—$C(O)OR^{17}$, wherein $R^{15}$ and $R^{17}$ are as previously defined.

In another embodiment, $R^1$ is wherein $R^{15}$ and $R^{17}$ are as previously defined.

In another embodiment, $R^1$ is wherein $R^{15}$ and $R^{17}$ are each independently selected from $C_1$-$C_6$alkyl.

In another embodiment, $R^1$ is wherein $R^{15}$ and $R^{17}$ are each independently selected from $C_1$-$C_6$alkyl.

In another embodiment, $R^1$ is wherein $R^{15}$ and $R^{17}$ are each independently selected from $C_1$-$C_6$alkyl.

In another embodiment, $R^1$ is

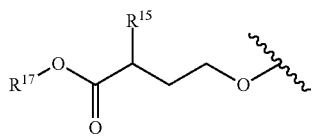

wherein $R^{15}$ is methyl and $R^{17}$ is selected from ethyl or propyl.

In another embodiment, $R^1$ is

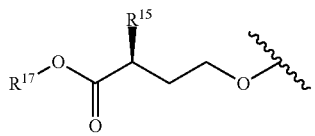

wherein $R^{15}$ is methyl and $R^{17}$ is selected from ethyl or propyl.

In another embodiment, $R^1$ is

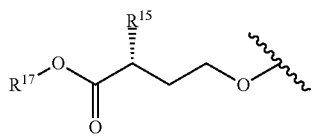

wherein $R^{15}$ is methyl and $R^{17}$ is selected from ethyl or propyl.

In another embodiment, $R^1$ is

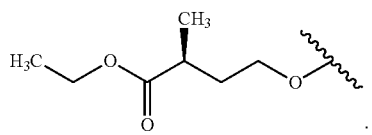 [SMILES: *OCC[C@H](C)C(=O)OCC]

In another embodiment, $R^1$ is

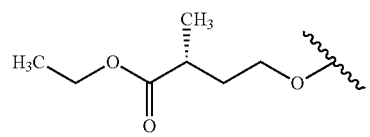 [SMILES: *OCC[C@@H](C)C(=O)OCC]

In another embodiment, $R^1$ is

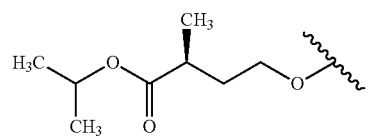 [SMILES: *OCC[C@H](C)C(=O)OC(C)C]

In another embodiment, $R^1$ is

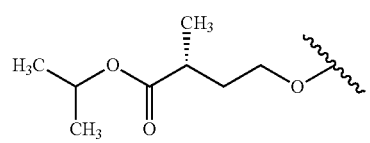

In one embodiment, $R^2$ is hydrogen, fluoro, chloro, —$OR^{13}$, —CN, —$N(R^{13})_2$ or $N_3$ with the proviso that if $R^2$ is OH and $R^3$, $R^4$ and V are hydrogen, then A is other than S and if $R^2$ is fluoro or chloro, then $R^3$ is other than fluoro or chloro.

In another embodiment, $R^2$ is $C_1$-$C_3$alkyl, $C_1$-$C_3$haloalkyl, $C_2$-$C_6$alkenyl or $C_2$-$C_3$alkynyl.

In another embodiment, $R^2$ is hydrogen, fluoro, chloro, methyl, amino or hydroxyl with the proviso that if $R^2$ is OH and $R^3$, $R^4$ and V are hydrogen, then A is other than S and if $R^2$ is fluoro or chloro, then $R^3$ is other than fluoro or chloro.

In another embodiment, $R^2$ is hydrogen, fluoro or —OH with the proviso that if $R^2$ is OH and $R^3$, $R^4$ and V are hydrogen, then A is other than S and if $R^2$ is fluoro or chloro, then $R^3$ is other than fluoro or chloro.

In another embodiment, $R^2$ is hydrogen.

In another embodiment, $R^2$ is fluoro and $R^3$ is other than fluoro or chloro.

In another embodiment, $R^2$ is OH and if $R^3$, $R^4$ and V are hydrogen, then A is other than S.

In one embodiment, $R^3$ is hydrogen, hydroxyl, fluoro, chloro, $N_3$, CN or $C_1$-$C_6$alkyl, with the proviso that if $R^2$ is fluoro or chloro, then $R^3$ is other than fluoro or chloro.

In another embodiment, $R^3$ is hydrogen, hydroxyl, fluoro, chloro or methyl with the proviso that if $R^2$ is fluoro or chloro, then $R^3$ is other than fluoro or chloro.

In another embodiment, $R^3$ is hydrogen.

In another embodiment, $R^4$ is hydrogen, $C_1$-$C_6$alkyl or $C_2$-$C_6$alkynyl.

In another embodiment, $R^4$ is hydrogen or ethynyl.

In another embodiment, $R^4$ is hydrogen.

In one embodiment, V is hydrogen or fluoro.

In another embodiment, V is hydrogen.

In one embodiment, V is hydrogen and each of $R^2$, $R^3$ and $R^4$ is hydrogen.

In another embodiment, V is fluoro and each of $R^2$, $R^3$ and $R^4$ is hydrogen.

In another embodiment, V is hydrogen, $R^2$ is fluoro and each of $R^3$ and $R^4$ is hydrogen.

In another embodiment, V is hydrogen, $R^2$ is hydroxyl and each of $R^3$ and $R^4$ is hydrogen.

In one embodiment, A is O, V is hydrogen and each of $R^2$, $R^3$ and $R^4$ is hydrogen.

In another embodiment, A is O, V is hydrogen, $R^2$ is fluoro and each of $R^3$ and $R^4$ is hydrogen.

In another embodiment, A is O, V is hydrogen, $R^2$ is hydroxyl and each of $R^3$ and $R^4$ is hydrogen.

In one embodiment, A is S, V is hydrogen and each of $R^2$, $R^3$ and $R^4$ is hydrogen.

In another embodiment, A is S, V is hydrogen, $R^2$ is fluoro and each of $R^3$ and $R^4$ is hydrogen.

In one embodiment, B is selected from the following groups:

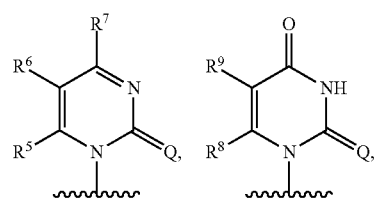

-continued

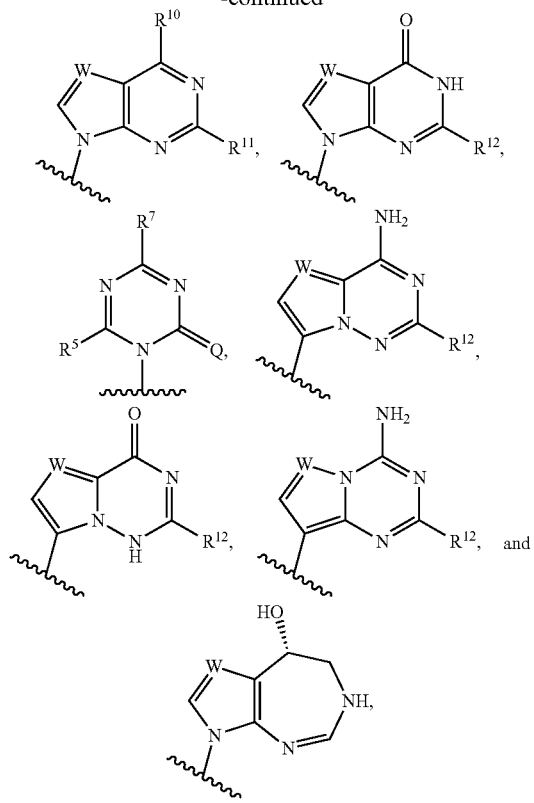

wherein Q, W and $R^5$ to $R^{12}$ are as defined previously.

In another embodiment, B is selected from the following groups:

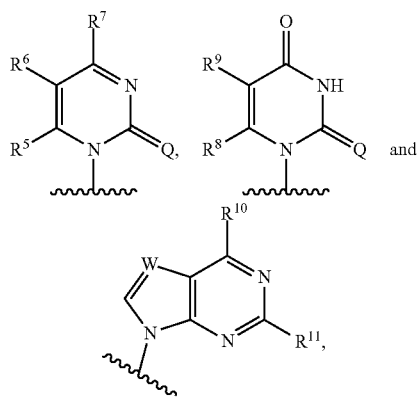

wherein Q, W and $R^5$ to $R^{11}$ are as defined previously.

In another embodiment, B is selected from the following groups:

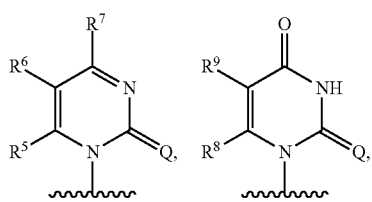

-continued

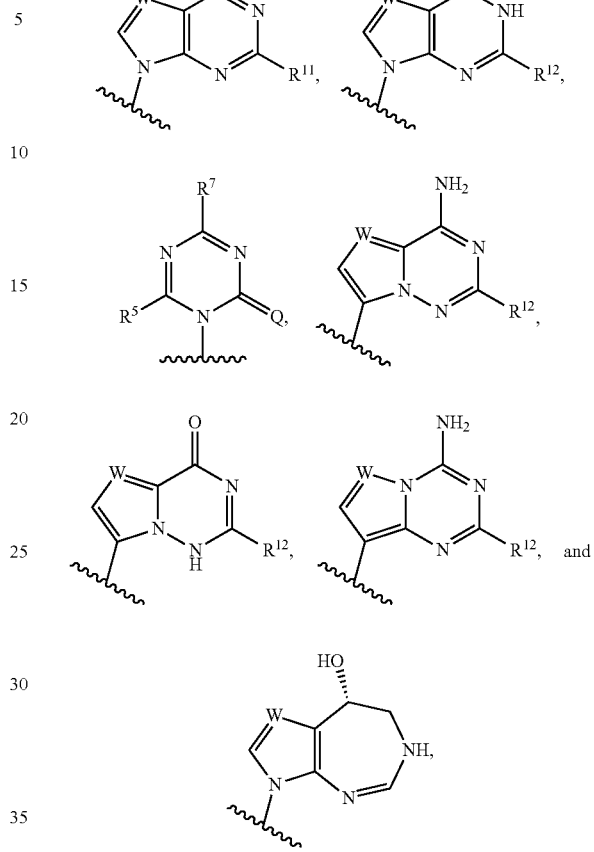

wherein Q is O; W is N or CH; $R^5$, $R^6$ and $R^8$ are each hydrogen; $R^7$ is amino or NHC(O)aryl; $R^9$ is hydrogen or trifluoromethyl; $R^{10}$ is —$NH_2$ or —O—$C_1$-$C_6$alkyl, $R^{11}$ is —$NH_2$ or halogen and $R^{12}$ is —$NH_2$ or halogen.

In another embodiment, B is selected from the following groups:

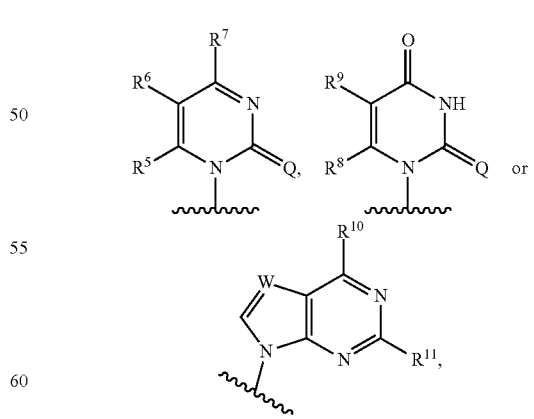

wherein Q is O; W is N; $R^5$, $R^6$ and $R^8$ are each hydrogen; $R^7$ is amino or NHC(O)aryl; $R^9$ is hydrogen or trifluoromethyl; $R^{10}$ is —$NH_2$ or —O—$C_1$-$C_6$alkyl and $R^{11}$ is —$NH_2$ or halogen.

In another embodiment, B is

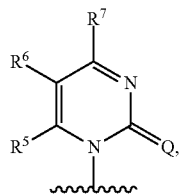

wherein, Q is O, $R^5$ and $R^6$ are each hydrogen and $R^7$ is amino or $NHC(O)R^{18}$, wherein $R^{18}$ is $C_1$-$C_6$alkyl or $C_6$-$C_{10}$aryl.

In another embodiment, B is

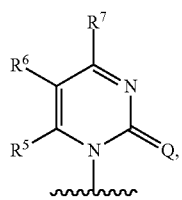

wherein, Q is O, $R^5$ and $R^6$ are each hydrogen and $R^7$ is amino.

In another embodiment, B is

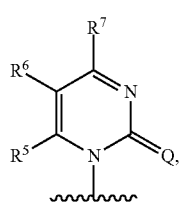

wherein, Q is O, $R^5$ and $R^6$ are each hydrogen and $R^7$ is $NHC(O)R^{18}$, wherein $R^{18}$ is $C_1$-$C_6$alkyl or $C_6$-$C_{10}$aryl.

In another embodiment, B is:

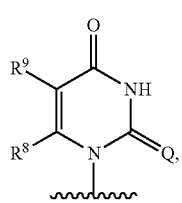

wherein Q is O and $R^8$ is hydrogen and $R^9$ is hydrogen or trifluoromethyl.

In another embodiment, B is:

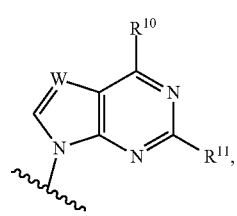

wherein W is N, $R^{10}$ is amino and $R^{11}$ is chloro.

In another embodiment, B is:

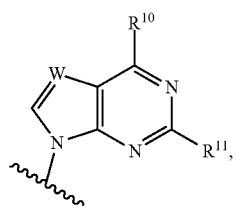

wherein W is N, $R^{10}$ is —$OR^{18}$ and $R^{11}$ is —$N(R^{18})_2$, wherein $R^8$ is as previously defined and each $R^{18}$ is selected independently of each other.

In another embodiment, B is:

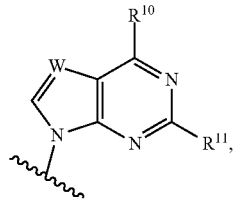

wherein W is N, $R^{10}$ is —O— $C_1$-$C_6$alkyl and $R^{11}$ is amino.

In another embodiment, B is:

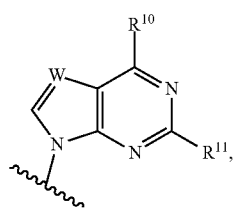

wherein W is N, $R^{10}$ is —O-ethyl and $R^{11}$ is amino.

In another embodiment, B is:

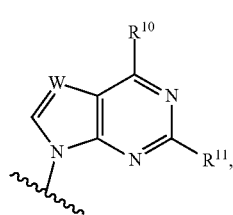

wherein W is N, $R^{10}$ is —O-methyl and $R^{11}$ is amino.

In another embodiment, B is:

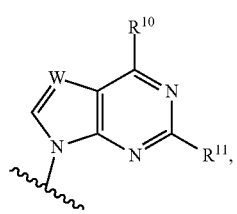

wherein W is N, $R^{10}$ is amino and $R^{11}$ is hydrogen.

In one embodiment is a compound according to Formula (I):

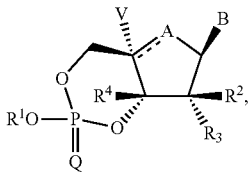
(I)

or a pharmaceutically acceptable salt, solvate or enantiomer thereof, wherein:
Q is O;
A is O or S;
$R^1$ is

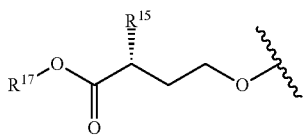

wherein $R^{15}$ is methyl and $R^{17}$ is selected from ethyl or propyl.
$R^2$ is F;
$R^3$, $R^4$ and V are H and
B is

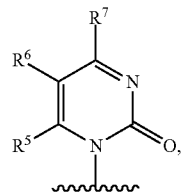

wherein, $R^5$ and $R^6$ are each hydrogen and $R^7$ is amino or NHC(O)$R^{18}$, wherein $R^{18}$ is $C_1$-$C_6$alkyl or $C_6$-$C_{10}$aryl.

In another embodiment is a compound according to Formula (I):

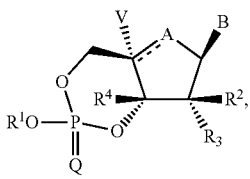
(I)

or a pharmaceutically acceptable salt, solvate or enantiomer thereof, wherein:
Q is O;
A is O or S;
$R^1$ is

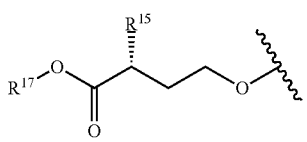

wherein $R^{15}$ is methyl and $R^{17}$ is selected from ethyl or propyl.

$R^2$, $R^3$, $R^4$ and V are hydrogen and
B is

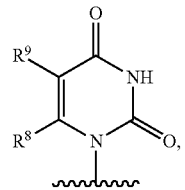

wherein, $R^8$ is hydrogen and $R^9$ is hydrogen or trifluoromethyl.

In another embodiment is a compound according to Formula (I):

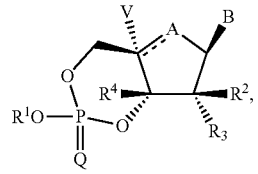
(I)

or a pharmaceutically acceptable salt, solvate or enantiomer thereof, wherein:
Q is O;
A is O or S;
$R^1$ is

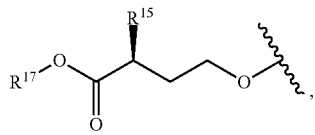

wherein $R^{15}$ is methyl and $R^{17}$ is selected from ethyl or propyl.
$R^2$ is hydrogen or fluorine;
$R^3$, $R^4$ and V are hydrogen and
B is

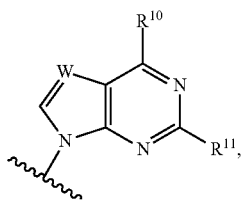

wherein W is N, $R^{10}$ is amino and $R^{11}$ is chloro.

In another embodiment is a compound according to Formula (I):

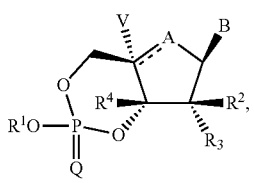
(I)

or a pharmaceutically acceptable salt, solvate or enantiomer thereof, wherein:

Q is O;
A is O;
R¹ is
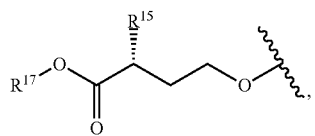
wherein R¹⁵ is methyl and R¹⁷ is selected from ethyl or propyl.
R² is hydroxy;
R³, R⁴ and V are hydrogen and
B is
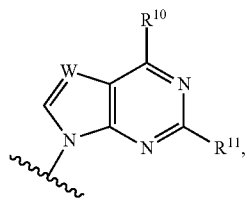
wherein W is N, R¹⁰ is methoxy and R¹¹ is amino.
In another embodiment is a compound of Formula I having the structure:
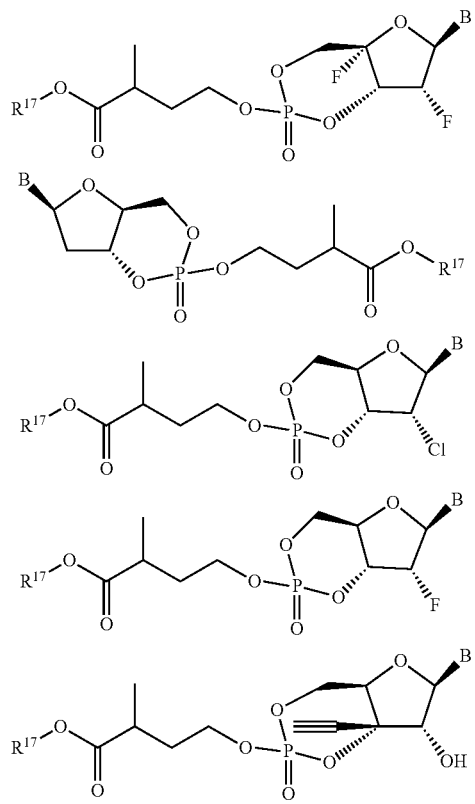
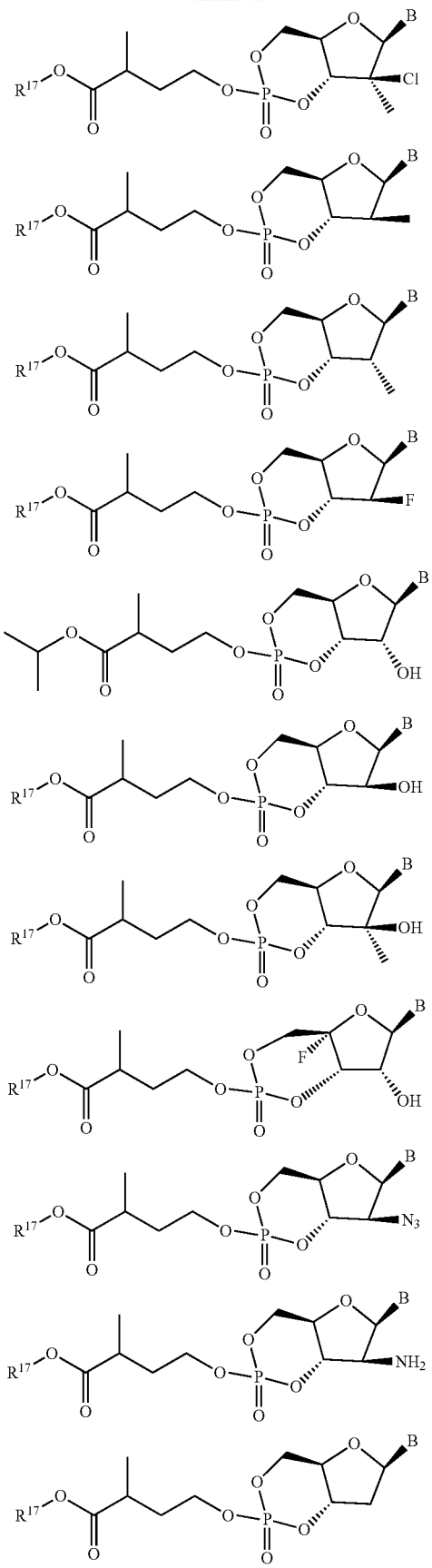

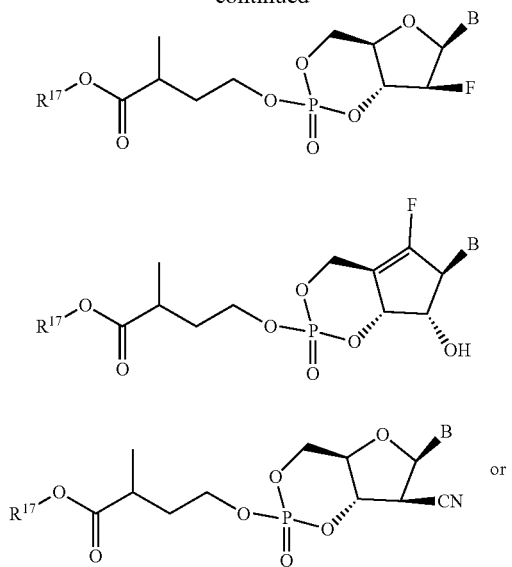
or a pharmaceutically acceptable salt or solvate thereof, wherein B and R$^{17}$ are as defined previously.
In another embodiment is a compound of Formula I having the structure:
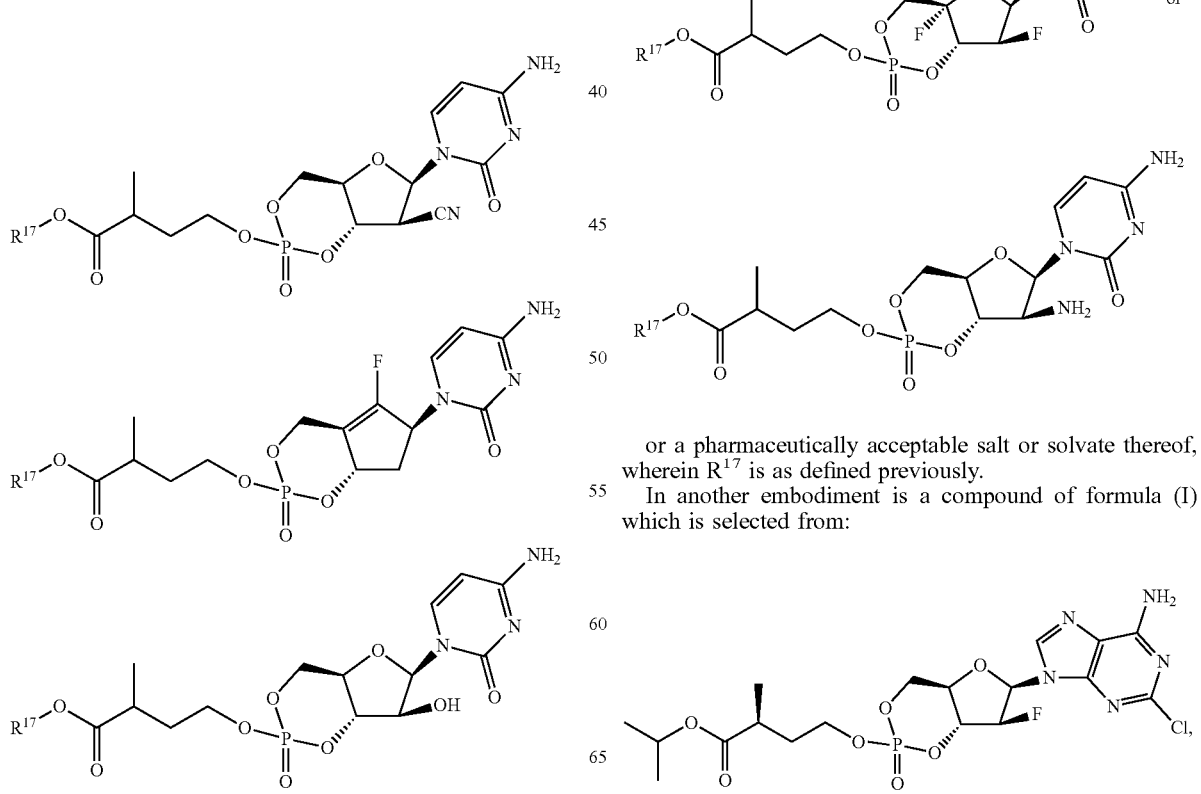
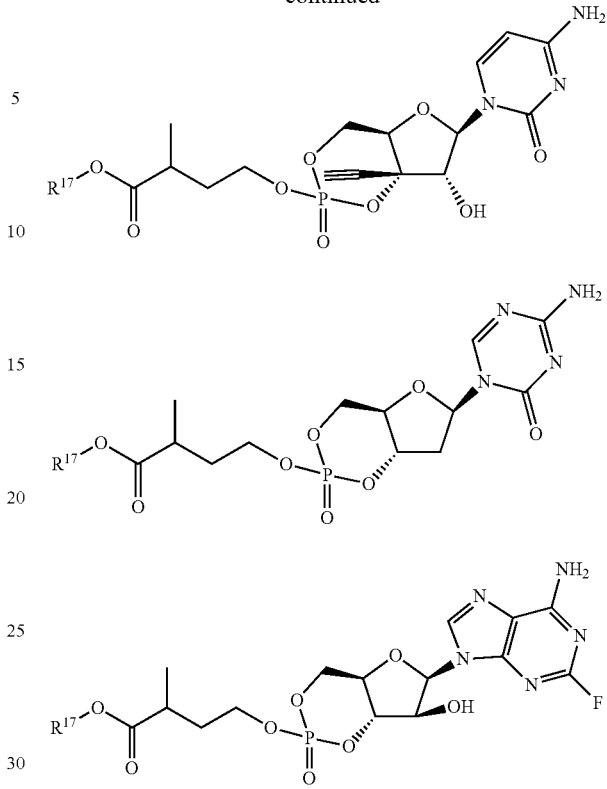
or a pharmaceutically acceptable salt or solvate thereof, wherein R$^{17}$ is as defined previously.
In another embodiment is a compound of formula (I) which is selected from:
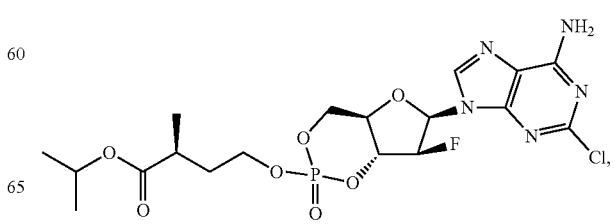

| 25 -continued | 26 -continued |
|---|---|
| 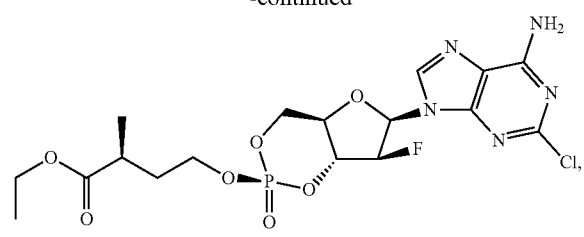 | 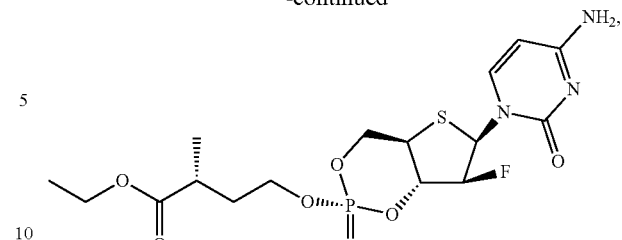 |
| 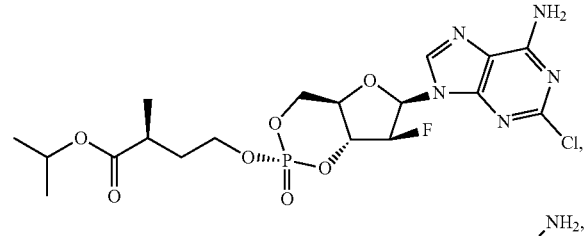 | 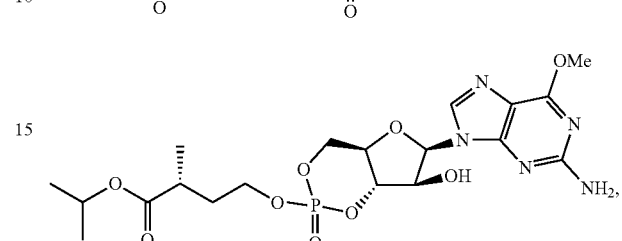 |
| 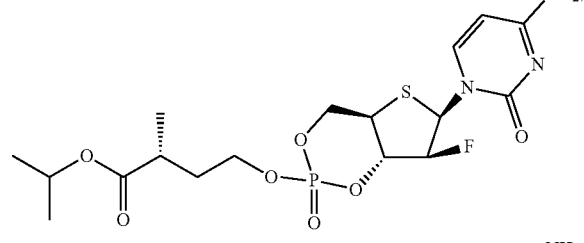 | 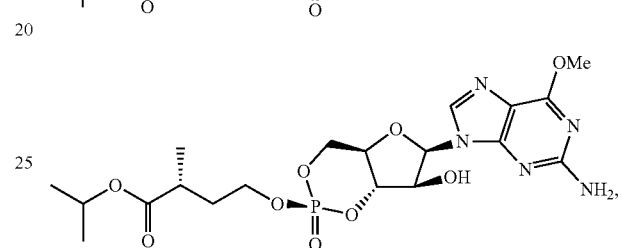 |
| 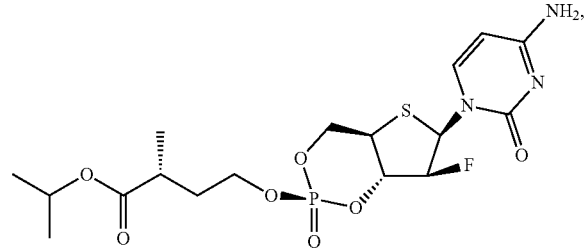 | 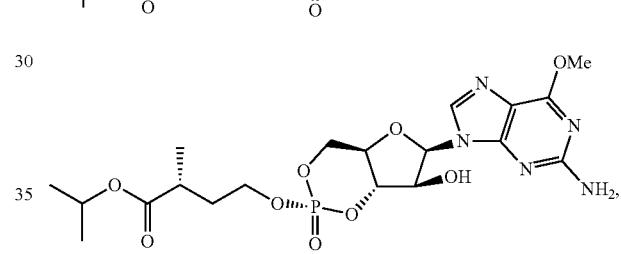 |
| 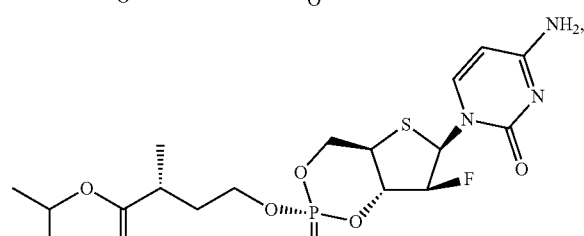 | 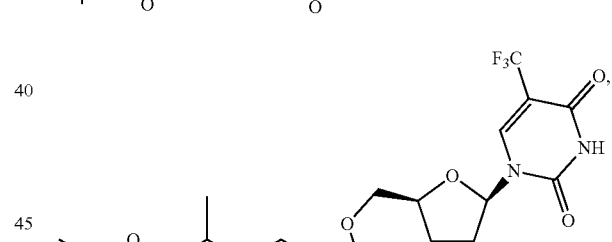 |
| 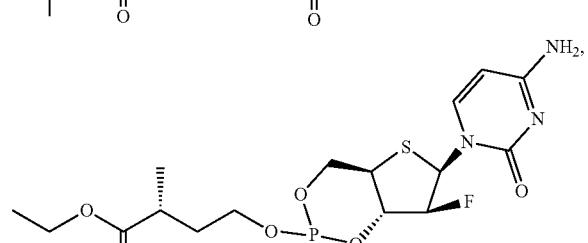 | 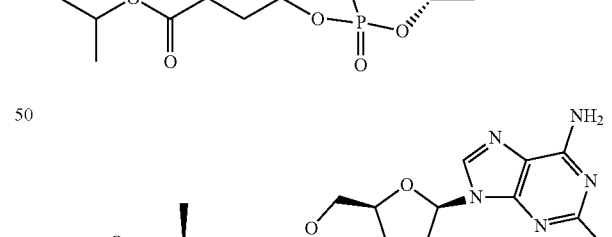 |
| 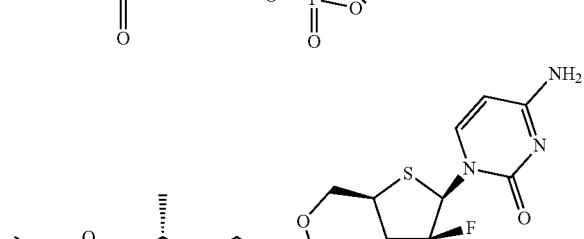 | 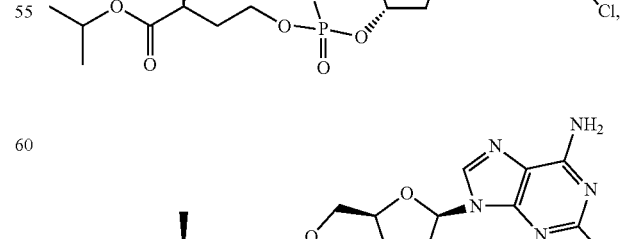 |

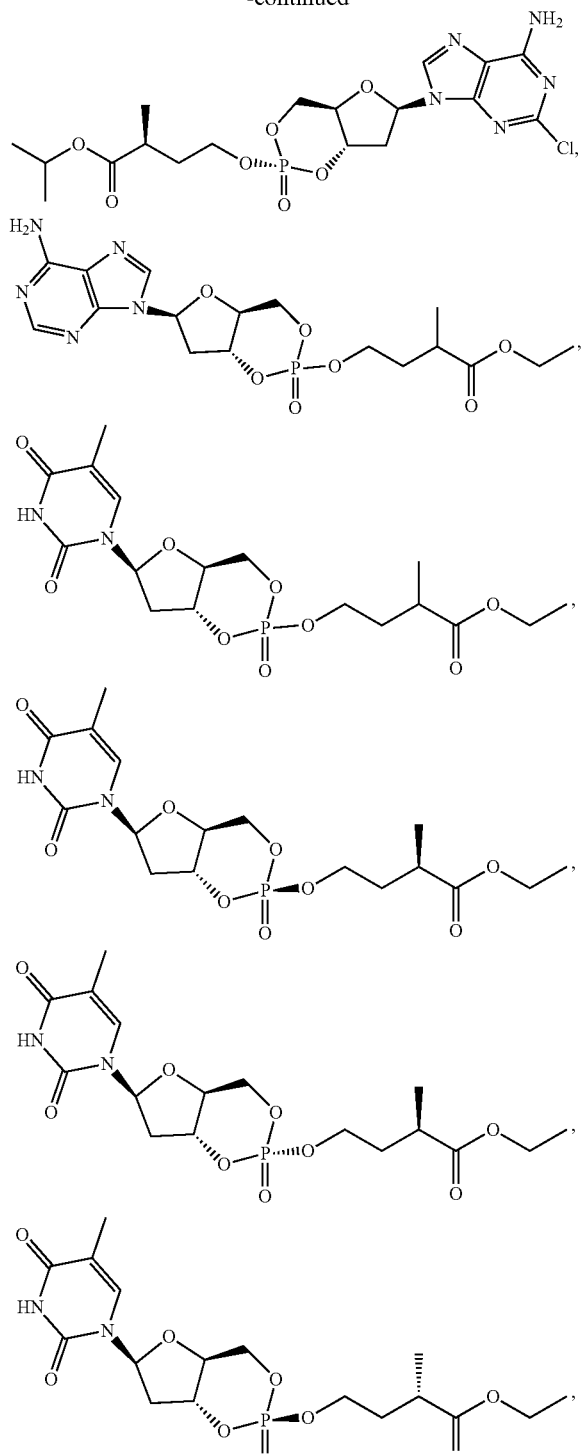

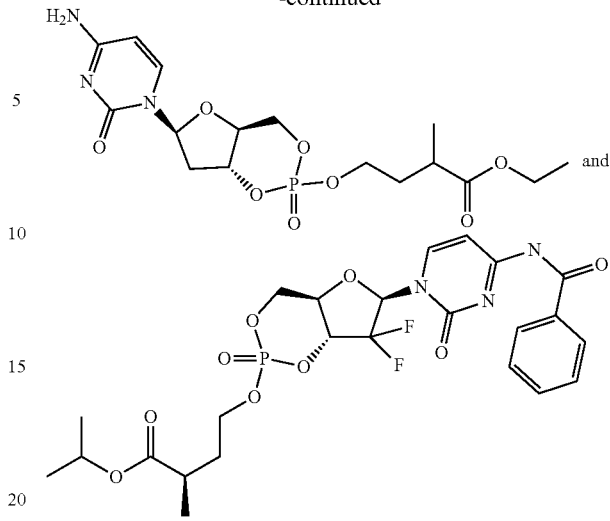

or a pharmaceutically acceptable salt or solvate thereof.

In one embodiment, variables A, B, $R^1$, $R^2$, $R^3$, Q and V for the Compounds of Formula (I) are selected independently of each other.

In another embodiment, the Compounds of Formula (I) are in substantially purified form.

The Compounds of Formula (II)

The present invention provides compounds of Formula (II), having the formula:

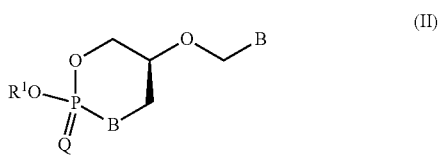

(II)

or a pharmaceutically acceptable salt or solvate thereof, wherein B, $R^1$ and Q are defined above for the compounds of Formula (II).

In one embodiment, Q is O.

In another embodiment, Q is S.

In one embodiment, $R^1$ is —$CH_2$—$C(R^{14})_2$—$C(R^{15})_2$—$C(O)OR^{17}$, wherein $R^{14}$, $R^{15}$ and $R^{17}$ are as previously defined.

In one embodiment, $R^1$ is —$CH_2$—$C(R^{14})_2$—$C(R^{15})_2$—$C(O)OR^{17}$, wherein $R^{14}$, $R^{15}$ and $R^{17}$ are each independently selected from hydrogen and $C_1$-$C_6$alkyl.

In another embodiment, $R^1$ is —$CH_2$—$CH_2$—$C(R^{15})_2$—$C(O)OR^{17}$, wherein $R^{15}$ and $R^{17}$ are as previously defined.

In another embodiment, $R^1$ is

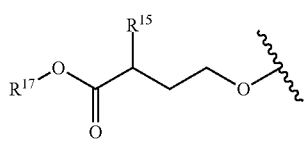

wherein $R^{15}$ and $R^{17}$ are as previously defined.

In another embodiment, $R^1$ is

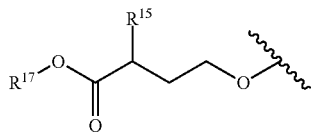

wherein $R^{15}$ and $R^{17}$ are each independently selected from $C_1$-$C_6$alkyl.

In another embodiment, $R^1$ is

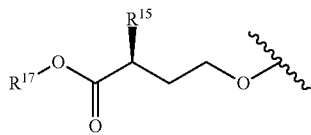

wherein $R^{15}$ and $R^{17}$ are each independently selected from $C_1$-$C_6$alkyl.

In another embodiment, $R^1$ is

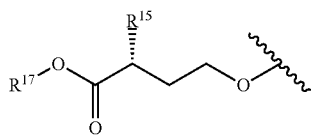

wherein $R^{15}$ and $R^{17}$ are each independently selected from $C_1$-$C_6$alkyl.

In another embodiment, $R^1$ is

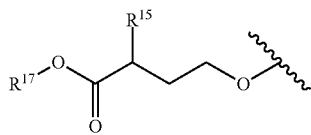

wherein $R^{15}$ is methyl and $R^{17}$ is selected from ethyl or propyl.

In another embodiment, $R^1$ is

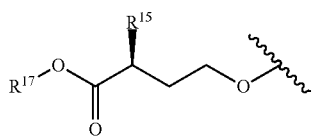

wherein $R^{15}$ is methyl and $R^{17}$ is selected from ethyl or propyl.

In another embodiment, $R^1$ is

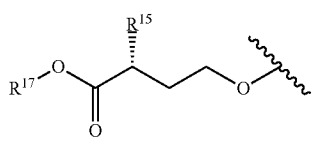

wherein $R^{15}$ is methyl and $R^{17}$ is selected from ethyl or propyl.

In another embodiment, $R^1$ is

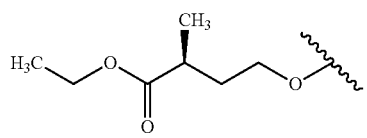 [SMILES: *OCC[C@@H](C)C(=O)OCC]

In another embodiment, $R^1$ is

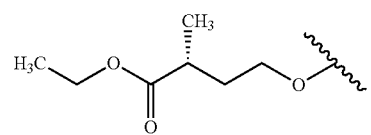

In another embodiment, $R^1$ is

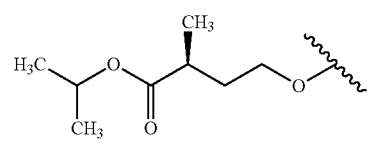

In another embodiment, $R^1$ is

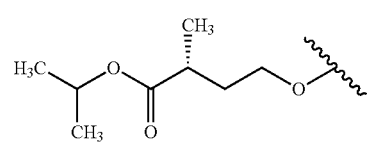 [SMILES: *OCC[C@@H](C)C(=O)OC(C)C]

In one embodiment, B is selected from the following groups:

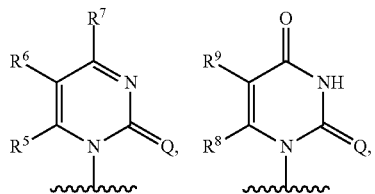

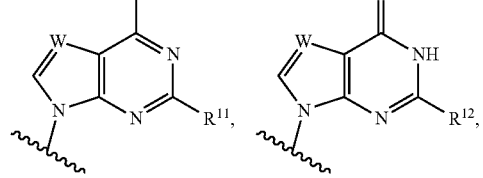

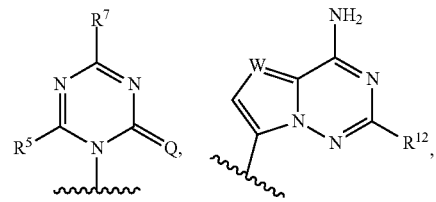

-continued

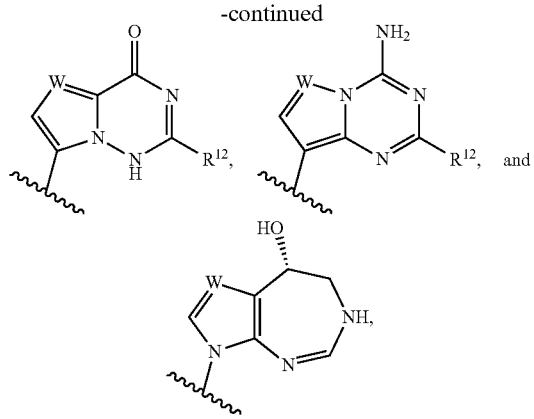

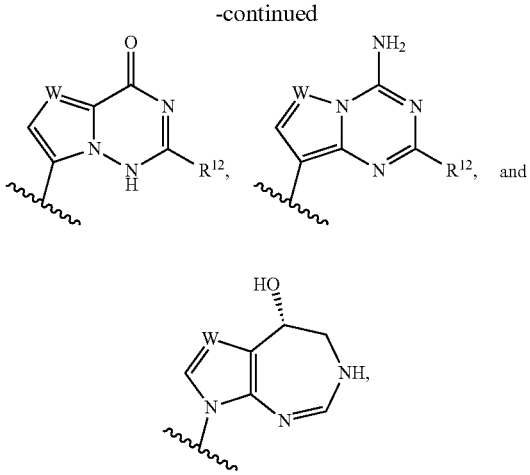

wherein Q, W and $R^5$ to $R^{12}$ are as defined previously.

In another embodiment, B is selected from the following groups:

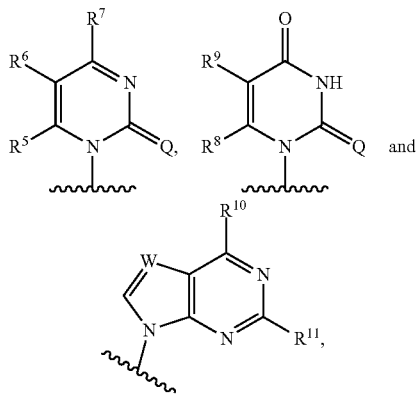

wherein Q, W and $R^5$ to $R^{11}$ are as defined previously.

In another embodiment, B is selected from the following groups:

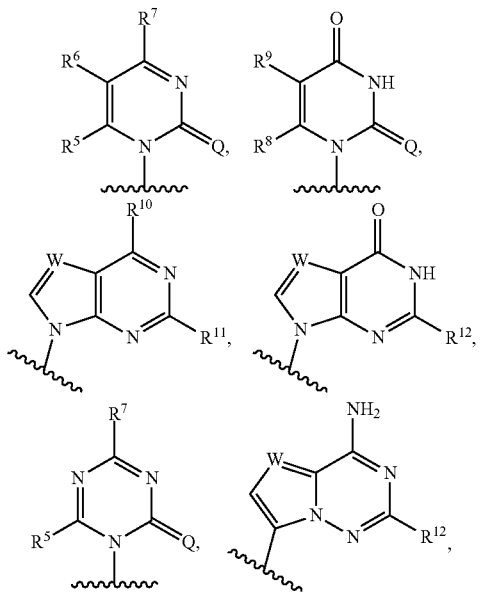

wherein Q is O; W is N or CH; $R^5$, $R^6$ and $R^8$ are each hydrogen; $R^7$ is amino; $R^9$ is hydrogen or trifluoromethyl; $R^{10}$ is —$NH_2$ or —O—$C_1$-$C_6$alkyl, $R^{11}$ is —$NH_2$ or halogen and $R^{12}$ is —$NH_2$ or halogen.

In another embodiment, B is selected from the following groups:

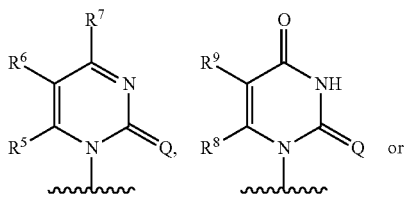

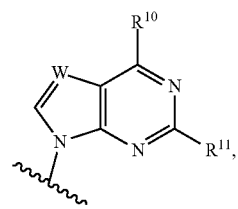

wherein Q is O; W is N; $R^5$, $R^6$ and $R^8$ are each hydrogen; $R^7$ is amino; $R^9$ is hydrogen or trifluoromethyl; $R^{10}$ is —$NH_2$ or —O—$C_1$-$C_6$alkyl and $R^{11}$ is —$NH_2$ or halogen.

In another embodiment, B is

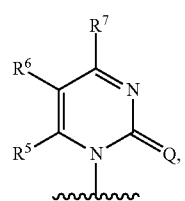

wherein, Q is O, $R^5$ and $R^6$ are each hydrogen and $R^7$ is amino or NHC(O)$R^{18}$, wherein $R^{18}$ is $C_1$-$C_6$alkyl or is $C_6$-$C_{10}$aryl In another embodiment, B is

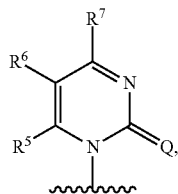

wherein, Q is O, $R^5$ and $R^6$ are each hydrogen and $R^7$ is amino.

In another embodiment, B is

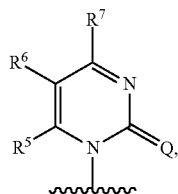

wherein, Q is O, $R^5$ and $R^6$ are each hydrogen and $R^7$ is $NHC(O)R^{18}$, wherein $R^{18}$ is $C_1$-$C_6$alkyl or is $C_6$-$C_{10}$aryl In another embodiment, B is:

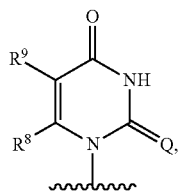

wherein Q is O and $R^8$ is hydrogen and $R^9$ is hydrogen or trifluoromethyl.

In another embodiment, B is:

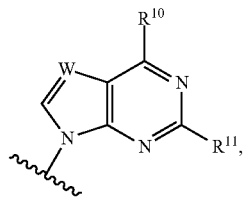

wherein W is N, $R^{10}$ is amino and $R^{11}$ is chloro.

In another embodiment, B is:

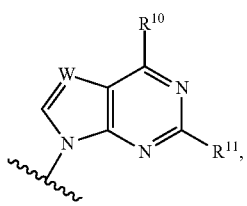

wherein W is N, $R^{10}$ is —$OR^{18}$ and $R^{11}$ is —$N(R^{18})_2$, wherein $R^{18}$ is as previously defined and each $R^{18}$ is selected independently of each other.

In another embodiment, B is:

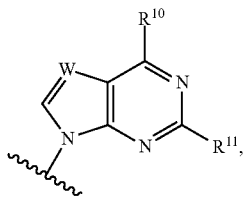

wherein W is N, $R^{10}$ is —O—$C_1$-$C_6$alkyl and $R^{11}$ is amino, wherein $R^{18}$ is as previously defined and each $R^{18}$ is selected independently of each other.

In another embodiment, B is:

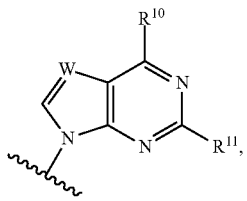

wherein W is N, $R^{10}$ is —O-ethyl and $R^{11}$ is amino, wherein $R^8$ is as previously defined and each $R^{18}$ is selected independently of each other.

In one embodiment is a compound according to Formula (II):

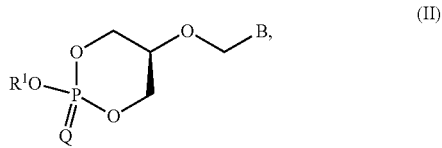

(II)

or a pharmaceutically acceptable salt or solvate thereof, wherein:
Q is O;
$R^1$ is

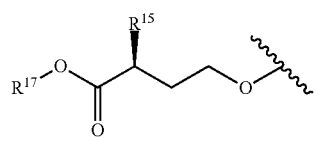

wherein $R^{15}$ is methyl and $R^{17}$ is selected from ethyl or propyl and
B is

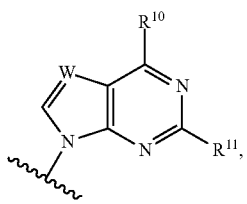

wherein, $R^{10}$ is —$OR^{18}$ and $R^{11}$ is $NHR^{18}$, wherein each $R^{18}$ is independently hydrogen or $C_1$-$C_6$alkyl.

In another embodiment is a compound according to Formula (II):

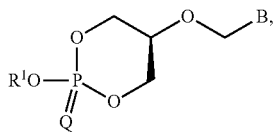

(II)

or a pharmaceutically acceptable salt or solvate thereof, wherein:

Q is O;

$R^1$ is

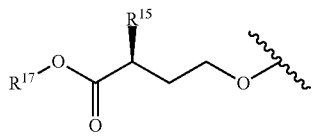

wherein $R^{15}$ is methyl and $R^{17}$ is selected from ethyl or propyl and

B is

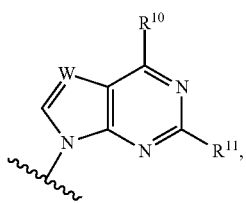

wherein, $R^{10}$ is —O-ethyl and $R^{11}$ is amino.

In another embodiment is a compound of formula (II) which is selected from:

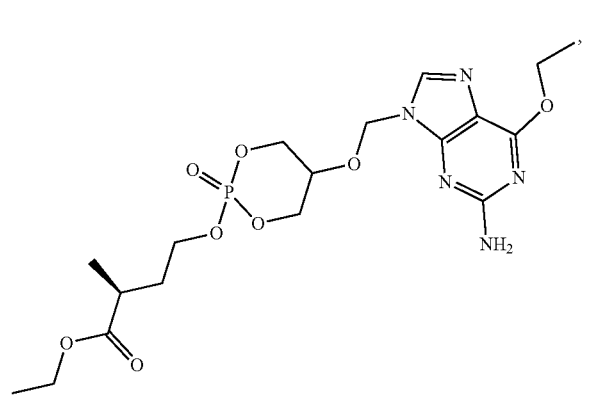

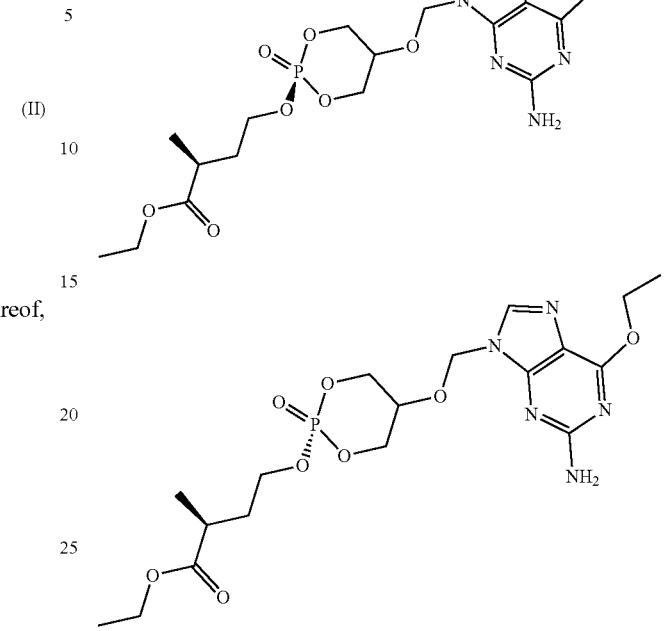

or a pharmaceutically acceptable salt or solvate thereof.

In one embodiment, variables B, $R^1$ and Q for the compounds of Formula (II) are selected independently of each other.

In another embodiment, the compounds of Formula (II) are in substantially purified form.

General Methods for Making the Compounds of Formula (I)

The compounds of Formula (I) or Formula (II) may be prepared from known or readily prepared starting materials, following methods known to one skilled in the art of organic synthesis. Methods useful for making the compounds of Formula (I) or Formula (II) are set forth in the Examples below and generalized in Schemes A, B and C below. Alternative synthetic pathways and analogous structures will be apparent to those skilled in the art of organic synthesis.

The following abbreviations are used herein:

| | |
|---|---|
| CH₃CN or ACN | acetonitrile |
| DBU | 1,8-diazabicyclo(5.4.0)undec-7-ene |
| DCM | dichloromethane |
| DMF | N,N-dimethylformamide |
| Et₃N | triethylamine |
| Et₂O | diethylether |
| NMI | N-methylimidazole |
| t-bu | tert-butyl |
| THF | tetrahydrofuran |

Scheme A shows a method useful for making nucleoside compounds of formula A4, which correspond to the compounds of Formula (I).

Scheme A

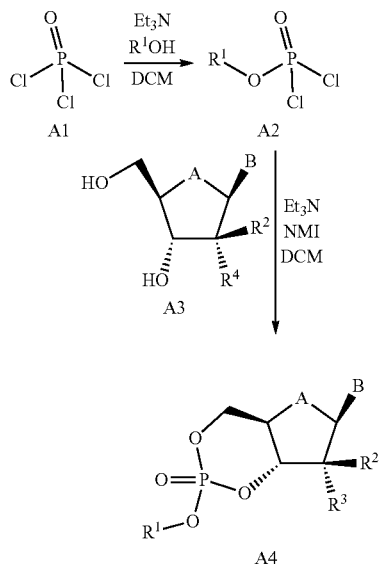

Phosphorus (V) oxychloride can be reacted with triethylamine and an alcohol of formula R¹OH as shown to provide a compound of formula A2. The compound of formula A2 is then reacted as shown with a nucleoside of formula A3 to provide a cyclic phosphate nucleoside prodrug of formula A4.

In Scheme A, the variables are as described in the context of Formula I. Nucleosides A3 can be prepared or obtained according to the knowledge in the art. Additional steps and reagents not provided in Scheme A would be known to those of skill in the art. Exemplary methods of preparation are described in detail in the Examples herein.

Scheme B shows an alternative method useful for making nucleoside compounds of formula A4, which correspond to the compounds of Formula (I).

Scheme B

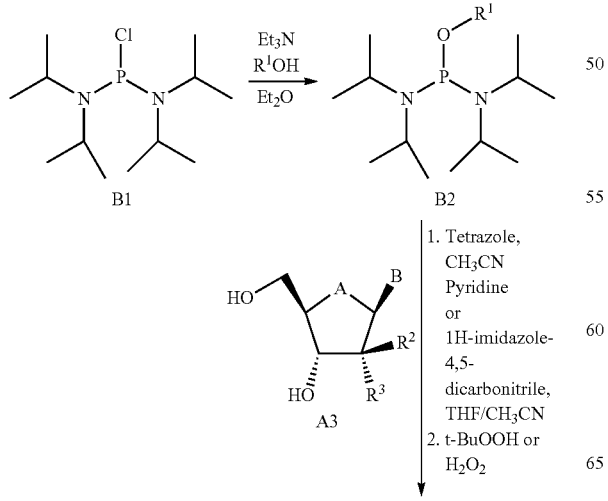

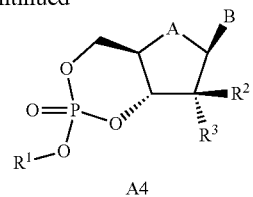

1-Chloro-N,N,N',N'-tetraisopropylphosphinediamine (B1) can be reacted as shown with triethylamine and an alcohol of formula R¹OH to provide a compound of formula B2. The compound of formula B2 is then reacted as shown with a nucleoside of formula A3 to provide a cyclic phosphate nucleoside prodrug of formula A4.

In Scheme B, the variables are as described in the context of Formula I. Nucleosides A3 can be prepared or obtained according to the knowledge in the art. Additional steps and reagents not provided in Scheme A would be known to those of skill in the art. Exemplary methods of preparation are described in detail in the Examples herein.

Scheme C shows an alternative method useful for making nucleoside compounds of formula A4, which correspond to the compounds of Formula (I).

Scheme C

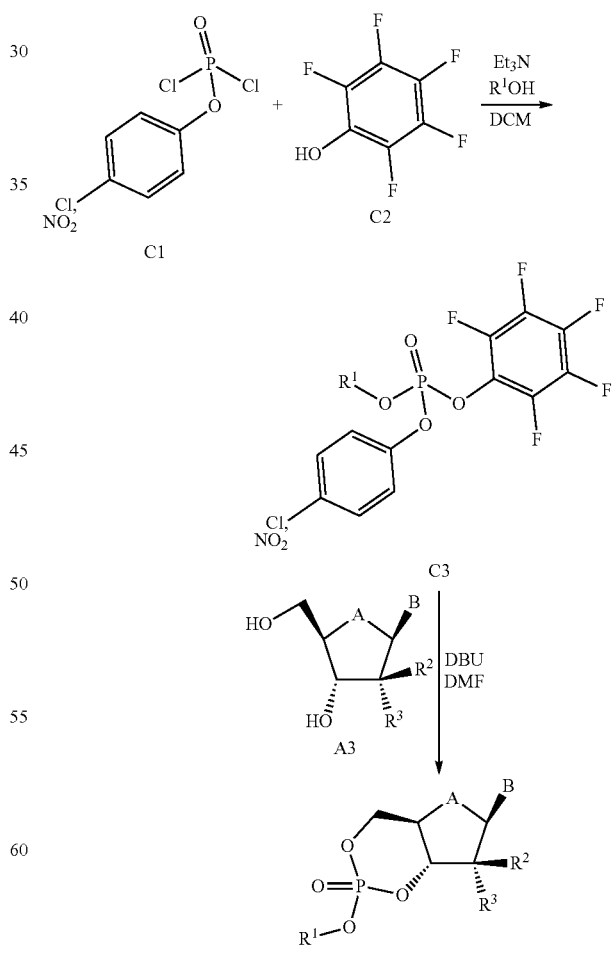

2,3,4,5,6-Pentafluorophenol (C2) can be reacted with 4-chlorophenyl phosphodichloridate or 4-nitrophenyl phosphodichloridate (C1), triethylamine and an alcohol of formula R¹OH as shown to provide a compound of formula C3. The compound of formula C3 is then reacted with a nucleoside of formula A3 as shown to provide a cyclic phosphate nucleoside prodrug of formula A4.

In Scheme C, the variables are as described in the context of Formula I. Nucleosides A3 can be prepared or obtained according to the knowledge in the art. Additional steps and reagents not provided in Scheme A would be known to those of skill in the art. Exemplary methods of preparation are described in detail in the Examples herein.

Compounds of Formula II can be prepared by analogous processes to those shown in Schemes A to C using the nucleoside A5 in place of nucleoside A3.

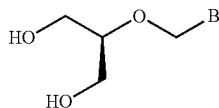

Nucleoside A5

FURTHER EMBODIMENTS OF THE COMPOUNDS OF FORMULA (I)

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Compound of Formula(I) or Formula (II), or a pharmaceutically acceptable salt of the compound. The transformation may occur by various mechanisms (e.g., by metabolic or chemical processes), such as, for example, through hydrolysis in blood.

For example, if a Compound of Formula(I) or Formula (II) contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a Compound of Formula(I) or Formula (II) contains an alcohol functional group, a prodrug can be formed by the replacement of one or more of the hydrogen atoms of the alcohol groups with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino$(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate). Other example of alcohol-derived prodrugs include —P(O)(OH)$_2$; —P(O)(—O—$C_1$-$C_6$alkyl)$_2$; —P(O)(—NH-(α-aminoacyl group))(—O-aryl); —P(O)(—O—$(C_1$-$C_6$ alkylene)-S-acyl)(—NH-arylalkyl); and those described in U.S. Pat. No. 7,879,815; International Publication Nos. WO2005/003047, WO2008/082602, WO2010/0081628, WO2010/075517 and WO2010/075549; Mehellou, *Chem. Med. Chem.*, 5:1841-1842(2005); Bobeck et al., *Antiviral Therapy* 15:935-950 (2010); Furman et al., Future Medicinal Chemistry, 1:1429-1452 (2009); and Erion, *Microsomes and Drug Oxidations, Proceedings of the International Symposium*, 17th, Saratoga Springs, N.Y., United States, Jul. 6-10, 2008, 7-12 (2008).

If a Compound of Formula(I) or Formula (II) incorporates an amine functional group, a prodrug can be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY¹ wherein Y¹ is H, $(C_1-C_6)$alkyl or benzyl, —C(OY²)Y³ wherein Y² is $(C_1-C_4)$ alkyl and Y³ is $(C_1-C_6)$alkyl; carboxy $(C_1-C_6)$alkyl; amino$(C_1-C_4)$alkyl or mono-N— or di-N,N—$(C_1-C_6)$alkylaminoalkyl; —C(Y⁴) Y⁵ wherein Y⁴ is H or methyl and Y⁵ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The compounds of Formula (I) or Formula (II) can form salts which are also within the scope of this invention. The term "salt(s)", as employed herein, denotes acidic salts formed with inorganic and/or organic acids, as well as basic salts formed with inorganic and/or organic bases. In addition, when a compound of Formula (I) or Formula (II) contains both a basic moiety, such as, a pyridine or imidazole, and an acidic moiety, such as, a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the compounds of Formula (I) or Formula (II) may be formed, for example, by reacting a compound of Formula (I) or Formula (II) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers (e.g., substituted biaryls) and diastereomeric forms, are contemplated within the scope of this invention. If a compound of Formula (I) or Formula (II) incorporates a double bond or a fused ring, both the cis- and trans-forms, as well as mixtures, are embraced within the scope of the invention.

It is also possible that the compounds of Formula (I) or Formula (II) may exist in different tautomeric forms, and all such forms are embraced within the scope of the invention. For example, all keto-enol and imine-enamine forms of the compounds are included in the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" and the like, is intended to apply equally to the salt and solvate of enantiomers, stereoisomers, rotamers, tautomers, positional isomers, racemates or prodrugs of the inventive compounds.

Diastereomeric mixtures may be separated into their individual diastereomers on the basis of their physical chemical differences by methods well-known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Stereochemically pure compounds may also be prepared by using chiral starting materials or by employing salt resolution techniques. Enantiomers can also be directly separated using chiral chromatographic techniques.

In the compounds of Formula (I) or Formula (II), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I) or Formula (II). For example, different isotopic forms of hydrogen (H) include protium (H) and deuterium (H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of Formula (I) or Formula (II) may be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) or Formula (II) has one or more of its hydrogen atoms replaced with deuterium.

Polymorphic forms of the compounds of Formula (I) or Formula (II), and of the salts or solvates of the Compounds of Formula (I) or Formula (II), are intended to be included in the present invention.

The compounds provided herein are based, at least in part, on the discovery that the cyclic phosphate prodrugs can provide superior human pharmacokinetics including superior accumulation of active nucleoside and nucleotide analogs in target cells, such as liver cells. Any compound provided herein is preferably in the form of a composition that is substantially free of other stereoisomers of the compound, as described herein.

Other embodiments of the present invention include the following:

(a) A pharmaceutical composition comprising an effective amount of a compound of Formula (I) or Formula (II), or a pharmaceutically acceptable salt, solvate or enantiomer thereof, and a pharmaceutically acceptable carrier or diluent.

(b) The pharmaceutical composition of (a), further comprising a second therapeutic agent selected from the group consisting of immunomodulators, anti-infective agents and anticancer agents.

(c) The pharmaceutical composition of (b), wherein the anti-infective agent is an antiviral, such as an HBV inhibitor.

(d) A combination comprising a compound of Formula (I) or Formula (II), or a pharmaceutically acceptable salt, solvate or enantiomer thereof and one, two, three or more other therapeutic agents.

(e) The combination of (d) that is (i) a Compound of Formula (I) or (II), or a pharmaceutically acceptable salt, solvate or enantiomer thereof, and (ii) a second therapeutic agent selected from the group consisting of immunomodulators, and anti-infective agents; wherein the Compound of Formula (I) or (II) and the second therapeutic agent are each employed in an amount that renders the combination effective for inhibiting HBV replication, or for treating HBV infection and/or reducing the likelihood or severity of symptoms of HBV infection.

(f) The combination of (d), wherein the anti-infective agent is an antiviral such as an HBV inhibitor.

(g) The combination of (d) that is (i) a Compound of Formula (I) or (II), or a pharmaceutically acceptable salt, solvate or enantiomer thereof, and (ii) a second therapeutic agent which is an anticancer agent; wherein the Compound of Formula (I) or (II) and the second therapeutic agent are each employed in an amount that renders the combination effective for treating and/or reducing the likelihood or severity of symptoms of cancer.

(h) A Compound of Formula (I) or (II), or a pharmaceutically acceptable salt, solvate or enantiomer thereof for use in therapy.

(i) The Compound for use of (h), wherein the therapy is treating cancer and/or reducing the likelihood or severity of symptoms of cancer, for example liver cancer, breast cancer, ovarian cancer, lung cancer, pancreatic cancer, cholangiocarcinoma, biliary tract cancer, hepatocellular carcinoma or leukemia, in a subject.

(j) The Compound for use of (h), wherein the therapy is treating HBV infection and/or reducing the likelihood or severity of symptoms of HBV infection in a subject.

(k) The Compound for use of (h), wherein the therapy is treating Ebolavirus infection and/or reducing the likelihood or severity of symptoms of Ebolavirus infection in a subject.

(l) The Compound for use of (h), (i), (j) or (k), wherein said compound is administered in combination with one or more other therapeutic agents.

(m) A method of treating or preventing cancer and/or reducing the likelihood or severity of symptoms of cancer, for example liver cancer, breast cancer, ovarian cancer, lung cancer, pancreatic cancer, cholangiocarcinoma, biliary tract cancer, hepatocellular carcinoma or leukemia, in a subject in need thereof which comprises administering to the subject an effective amount of a compound of Formula (I) of Formula (II) or a pharmaceutically acceptable salt, solvate or enantiomer thereof.

(n) A method of treating or preventing cancer and/or reducing the likelihood or severity of symptoms of cancer, for example liver cancer, breast cancer, ovarian cancer, lung cancer, pancreatic cancer, cholangiocarcinoma, biliary tract cancer, hepatocellular carcinoma or leukemia, in a subject in need thereof which comprises administering to the subject the pharmaceutical composition of (a), (b) or (c) or the combination of (d) or (g).

(o) A method of inhibiting HBV replication in a subject in need thereof which comprises administering to the subject an effective amount of a compound of Formula (I) or Formula (II) or a pharmaceutically acceptable salt, solvate or enantiomer thereof.

(p) A method of treating HBV infection and/or reducing the likelihood or severity of symptoms of HBV infection in a subject in need thereof which comprises administering to the subject an effective amount of a compound of Formula (I) of Formula (II) or a pharmaceutically acceptable salt, solvate or enantiomer thereof.

(q) A method of treating Ebolavirus infection and/or reducing the likelihood or severity of symptoms of Ebolavirus infection in a subject in need thereof which comprises administering to the subject an effective amount of a compound of Formula (I) of Formula (II) or a pharmaceutically acceptable salt, solvate or enantiomer thereof.

(r) The method of (o), (p) or (q) wherein the compound of Formula (I) or Formula (II) is administered in combination with an effective amount of at least one second therapeutic agent selected from the group consisting of immunomodulators, and anti-infective agents.

(s) The method of (r), wherein the anti-infective agent is an antiviral, such as an HBV inhibitor.

(t) A method of inhibiting HBV replication in a subject in need thereof which comprises administering to the subject the pharmaceutical composition of (a), (b) or (c) or the combination of (d), (e) or (f).

(u) A method of treating HBV infection and/or reducing the likelihood or severity of symptoms of HBV infection in a subject in need thereof which comprises administering to the subject the pharmaceutical composition of (a), (b) or (c) or the combination of (d), (e) or (f).

(v) A method of treating Ebolavirus infection and/or reducing the likelihood or severity of symptoms of Ebolavirus infection in a subject in need thereof which comprises administering to the subject the pharmaceutical composition of (a), (b) or (c) or the combination of (d).

Additional embodiments of the invention include the pharmaceutical compositions, combinations and methods set forth in (a)-(v) above and the uses set forth in the discussion below, wherein the compound of the present invention employed therein is a compound of one of the embodiments, aspects, classes, sub-classes, or features of the compounds described above. In all of these embodiments, the compound may optionally be used in the form of a pharmaceutically acceptable salt or solvate as appropriate. It is understood that references to compounds would include the compound in its present form as well as in different forms, such as polymorphs and solvates as applicable.

It is further to be understood that the embodiments of compositions and methods provided as (a) through (v) above are understood to include all embodiments of the compounds, including such embodiments as result from combinations of embodiments.

Treatment or Prevention of Cancer

Compounds of Formula (I) and Formula (II) are further useful in the treatment or prevention of cancer and/or reducing the likelihood or severity of symptoms of cancer, In one embodiment, the cancer is selected from liver cancer, breast cancer, ovarian cancer, lung cancer, pancreatic cancer or leukemic cancer. In a further embodiment the cancer is liver cancer. Liver cancers which can be treated include primary and secondary liver cancers. In particular embodiments, the liver cancer is hepatocellular carcinoma, cholangiocarcinoma, or biliary tract cancer. In particular embodiments, the liver cancer is a metastasis in the liver originated from other cancers (such as colon cancer, pancreatic cancer, etc).

Accordingly, the invention also provides methods for treating or preventing cancer and/or reducing the likelihood or severity of symptoms of cancer in a patient, the methods comprising administering to the patient an effective amount of at least one compound of Formula (I) or Formula (II) or a pharmaceutically acceptable salt, solvate or enantiomer thereof.

In further embodiments, the cancers which can be treated by the compounds described herein include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Cholangiocarcinoma; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

The compounds of Formula (I) and Formula (II) are further useful in inhibiting the growth of a cancer cell or inhibiting replication of a cancer cell. In certain embodiments, the cancer is selected from liver cancer, breast cancer, ovarian cancer, lung cancer, pancreatic cancer or leukemic cancer. In an embodiment the cancer is liver cancer. In certain embodiments, the liver cancer is hepatocellular carcinoma, cholangiocarcinoma, or biliary tract cancer. In particular embodiments, the cancer is hepatocellular carcinoma.

Treatment or Prevention of Viral Infection

The compounds of Formula (I) and Formula (II) are useful in the inhibition of viral infection, the treatment viral infection and/or reduction of the likelihood or severity of symptoms of viral infection and the inhibition of viral replication and/or viral production in a cell-based system. For example, the compounds of Formula (I) and Formula (II) are useful in treating viral infection after suspected past exposure to the virus by such means as blood transfusion, exchange of body fluids, bites, accidental needle stick, or exposure to patient blood during surgery or other medical procedures.

In a further embodiment, the compounds of Formula (I) and Formula (II) are useful in the inhibition of HBV, the treatment of HBV infection and/or reduction of the likelihood or severity of symptoms of HBV infection and the inhibition of HBV replication and/or HBV production in a cell-based system. For example, the compounds of Formula (I) and Formula (II) are useful in treating infection by HBV after suspected past exposure to HBV by such means as blood transfusion, exchange of body fluids, bites, accidental needle stick, or exposure to patient blood during surgery or other medical procedures.

In one embodiment, the hepatitis B infection is acute hepatitis B. In another embodiment, the hepatitis B infection is chronic hepatitis B.

Accordingly, in one embodiment, the invention provides methods for treating HBV infection in a patient, the methods comprising administering to the patient an effective amount of at least one compound of Formula (I) or Formula (II) or a pharmaceutically acceptable salt, solvate or enantiomer thereof. In a specific embodiment, the amount administered is effective to treat or prevent infection by HBV in the patient. In another specific embodiment, the amount administered is effective to inhibit HBV viral replication and/or viral production in the patient.

In a further embodiment, the compounds and compositions provided herein are useful in methods of treatment of a liver disorder, that comprise further administration of a second or more agent effective for the treatment of the disorder, such as HBV infection in a subject in need thereof. The second agent can be any agent known to those of skill in the art to be effective for the treatment of the disorder, including those currently approved by the FDA.

In a further embodiment, the compounds of Formula (I) and Formula (II) are useful in the inhibition of ebola virus, the treatment of Ebolavirus infection and/or reduction of the likelihood or severity of symptoms of Ebolavirus infection and the inhibition of Ebolavirus replication and/or Ebolavirus production in a cell-based system. For example, the compounds of Formula (I) and Formula (II) are useful in treating infection by Ebolavirus after suspected past exposure to ebola virus by such means as blood transfusion, exchange of body fluids, bites, accidental needle stick, or exposure to patient blood during surgery or other medical procedures.

Combination Therapy

In another embodiment, the present compounds, compositions, combinations and methods for treating or preventing liver diseases, such as cancer or viral infection, can further comprise the administration of one or more additional therapeutic agents which are not compounds of Formula (I) or Formula (II).

In one embodiment, the additional therapeutic agent is an anticancer agent.

In another embodiment, the additional therapeutic agent is an antiviral agent.

In another embodiment, the additional therapeutic agent is an immunomodulatory agent, such as an immunosuppressive agent.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for illustration purposes, a Compound of Formula (I) or Formula (II) and an additional therapeutic agent may be present in fixed amounts (dosage amounts) in a single dosage unit (e.g., a capsule, a tablet and the like).

In one embodiment, the at least one compound of Formula (I) or Formula (II) is administered during a time when the additional therapeutic agent(s) exert their prophylactic or therapeutic effect, or vice versa.

In another embodiment, the at least one compound of Formula (I) or Formula (II) and the additional therapeutic agent(s) are administered in doses commonly employed when such agents are used as monotherapy for treating a cancer or a viral infection.

In another embodiment, the at least one compound of Formula (I) or Formula (II) and the additional therapeutic agent(s) are administered in doses lower than the doses commonly employed when such agents are used as monotherapy for treating a cancer or a viral infection.

In still another embodiment, the at least one compound of Formula (I) or Formula (II) and the additional therapeutic agent(s) act synergistically and are administered in doses lower than the doses commonly employed when such agents are used as monotherapy for treating a cancer or a viral infection.

In one embodiment, the at least one compound of Formula (I) or Formula (II) and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

In another embodiment, the present invention provides compositions comprising a Compound of Formula (I) or Formula (II), a pharmaceutically acceptable carrier, and a second therapeutic agent selected from the group consisting of immunomodulators, anti-infective agents and anti-cancer agents.

In another embodiment, the present invention provides compositions comprising a Compound of Formula (I) or Formula (II), a pharmaceutically acceptable carrier, and two additional therapeutic agents, each of which are independently selected from the group consisting of immunomodulators, anti-infective agents and anti-cancer agents.

In one embodiment, the present invention provides a compound of Formula (I) or Formula (II) for use in treating cancer in a patient comprising administering to the patient: (i) at least one compound of Formula (I) or Formula (II) (which may include two or more different 2'-Substituted Nucleoside Derivatives), or a pharmaceutically acceptable salt or solvate thereof, and (ii) at least one additional therapeutic agent that is other than a compound of Formula (I) or Formula (II), wherein the amounts administered are together effective to treat or prevent cancer.

In certain embodiments the compounds and compositions provided herein are useful in the treatment of a liver cancer, that comprise further administration of a second agent effective for the treatment of the liver cancer in a subject in need thereof. The second agent can be any agent known to those of skill in the art to be effective for the treatment of the liver cancer, including those currently approved by the FDA.

In certain embodiments, a compound provided herein is administered in combination with one second agent. In further embodiments, a compound provided herein is administered in combination with two second agents. In still further embodiments, a compound provided herein is administered in combination with two or more second agents.

The active compounds provided herein can be administered in combination or alternation with another therapeutic agent, in particular an anti-cancer agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

In certain embodiments, the second agent is selected from the group consisting of sorafenib tosylate (Nexavar), radiation therapy, selective internal radiation therapy (e.g., SIR-Spheres and TheraSphere), ethiodized oil (Lipidol), pexastimogene devacirepvec (Pexa-Vec, JX-594, Jennarex), Quinacrine (Clevelane BioLabs), CC-223 (Celgene), CF102 (Can-Fite), SGI-110 (Astex), and G-202 (Genspera).

In one embodiment, the other anticancer agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3, PD-1 antagonists and BET bromodomain inhibitors.

Examples of vascular endothelial growth factor (VEGF) receptor inhibitors include, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-y!)-2-[(4-pyridinyimethyj)amino]-3-pyfidin-ecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors include, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents include, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, and sold under the tradename Thioplex®.

Examples of anti-tumor antibiotics include, doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), and pentostatin (sold under the tradename Nipent®).

Examples of retinoids include, alitretinoin (sold under the tradename Panretin®), tretinoin (all-trans retinoic acid, also known as ATRA, sold under the tradename Vesanoid®), Isotretinoin (13-c/s-retinoic acid, sold under the tradenames Accutane®, Amnesteem®, Claravis®, Clarus®, Decutan®, Isotane®, Izotech®, Oratane®, Isotret®, and Sotret®), and bexarotene (sold under the tradename Targretin®).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the compositions and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include, an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, arsenic trioxide (sold under the tradename Trisenox®), asparaginase (also known as L-asparaginase, and *Erwinia* L-asparaginase, sold under the tradenames Elspar® and Kidrolase®).

In an embodiment, the other anticancer agent is a BET bromodomain inhibitor. Examples of BET bromodomain inhibitor include the compounds described in U.S. Pat. No. 5,712,274, WO1994006802, U.S. Pat. No. 8,476,260 and WO2009/084693.

In a further embodiment, the present invention provides a compound of Formula (I) or Formula (II) for use in treating a viral infection in a patient comprising administering to the patient: (i) at least one compound of Formula (I) or Formula (II) (which may include two or more different 2'-Substituted Nucleoside Derivatives), or a pharmaceutically acceptable salt or solvate thereof, and (ii) at least one additional therapeutic agent that is other than a compound of Formula (I) or Formula (II), wherein the amounts administered are together effective to treat or prevent a viral infection.

Accordingly, in one embodiment, the present invention provides compositions comprising: (i) at least one Compound of Formula (I) or Formula (II) or a pharmaceutically acceptable salt, solvate or enantiomer thereof; (ii) one or more additional therapeutic agents that are not a Compound of Formula (I) or Formula (II); and (iii) a pharmaceutically acceptable carrier, wherein the amounts in the composition are together effective to prevent HBV replication and/or treat HBV infection.

In another embodiment, the present invention provides compositions comprising: (i) at least one Compound of Formula (I) or Formula (II) or a pharmaceutically acceptable salt, solvate or enantiomer thereof; (ii) one or more additional therapeutic agents that are not a Compound of Formula (I) or Formula (II); and (iii) a pharmaceutically acceptable carrier, wherein the amounts in the composition are together effective to prevent Ebolavirus replication and/or treat Ebolavirus infection.

Viral infections and virus-related disorders that may be treated or prevented using the combination therapy of the present invention include those listed above.

In one embodiment, the viral infection is HBV infection.

In another embodiment, the viral infection is Ebolavirus infection.

The at least one compound of Formula (I) or Formula (II) and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one compound of Formula (I) or Formula (II) and the additional therapeutic agent(s) may inhibit the resistance of a viral infection to these agents.

Examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, one or more compounds of the invention are administered with one or more additional therapeutic agents, including the therapeutic agents described, supra.

In one embodiment, the additional therapeutic agent is a viral protease inhibitor.

In another embodiment, the additional therapeutic agent is a viral replication inhibitor.

In another embodiment, the additional therapeutic agent is an HBV entry inhibitor.

In another embodiment, the additional therapeutic agent is an HBV capsid inhibitor.

In still another embodiment, the additional therapeutic agent is an HBV polymerase inhibitor.

In another embodiment, the additional therapeutic agent is a nucleoside inhibitor.

In another embodiment, the additional therapeutic agent is an interferon.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In still another embodiment, one or more compounds of the present invention are administered with two additional therapeutic agents.

In another embodiment, one or more compounds of the present invention are administered with three additional therapeutic agents.

In another embodiment, one or more compounds of the present invention are administered with an HBV polymerase inhibitor.

In another embodiment, one or more compounds of the present invention are administered with lamivudine.

In a further embodiment, one or more compounds of the present invention are administered with tenofovir.

In another embodiment, one or more compounds of the present invention are administered with pegylated-interferon alpha and ribavirin.

In one embodiment, the additional therapeutic agents comprise a viral protease inhibitor and a viral polymerase inhibitor.

In still another embodiment, the additional therapeutic agents comprise a viral protease inhibitor and an immunomodulator agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In another embodiment, the additional therapeutic agents comprise a nucleoside and an HBV polymerase inhibitor.

In a further embodiment, the additional therapeutic agents comprise a viral protease inhibitor, a viral polymerase inhibitor and an immunomodulatory agent.

In another embodiment, the additional therapeutic agent is ribavirin.

HBV polymerase inhibitors useful in the present compositions and treatments include lamivudine (Epivir), adefovir (Hepsera), tenofovir (Viread), telbivudine (Tyzeka), ganciclovir (Cytovene), entecavir (Baraclude), interferon alpha-2a, and PEGylated interferon alpha-2a (Pegasys).

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (ZymoGenetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Examples of other HBV inhibitors useful in the present compositions and treatments include TLR-3 or TLR-7 agonists, virus entry inhibitors, cccDNA formation inhibitors, silenceor of cccDNA, nucleocapsid formation inhibitors, virion maturation, assembly or secretion inhibitors.

The doses and dosage regimen of the other agents used in the combination therapies of the present invention for the treatment or prevention of the viral infection may be determined using the attending clinician, taking into consideration the approved doses and dosage regimen in the package insert; the age, sex and general health of the patient; and the type and severity of the viral infection or related disease or disorder. When administered in combination, the compound of Formula (I) or Formula (II) and the other agent(s) may be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Compound of Formula (I) or Formula (II) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

Compositions and Administration

Due to their activity, the compounds of Formula (I) and Formula (II) are useful in veterinary and human medicine. As described above, the compounds of Formula (I) and Formula(II) are useful for treating or preventing liver diseases, such as cancer, HBV infection or Ebolavirus infection in a patient.

When administered to a patient, the compounds of Formula (I) or Formula (II) may be administered as a component of a composition that comprises a pharmaceutically acceptable carrier or vehicle. The present invention provides pharmaceutical compositions comprising an effective amount of at least one compound of Formula (I) or Formula (II) or a pharmaceutically acceptable salt, solvate or enantiomer thereof and a pharmaceutically acceptable carrier or diluent. In the pharmaceutical compositions and uses of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more compounds of Formula (I) or Formula (II) are administered orally.

In another embodiment, the one or more compounds of Formula (I) or Formula (II) are administered intravenously.

In one embodiment, a pharmaceutical preparation comprising a compound of Formula (I) or Formula (II) is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the compound of Formula (I) or Formula (II) by weight or volume. In various embodiments, the present compositions can contain, in one embodiment, from about 1% to about 70% or from about 5% to about 60% of the compound of Formula (I) or Formula (II) by weight or volume.

The quantity of compound of Formula (I) or Formula (II) in a unit dose of preparation may be varied or adjusted from about 1 mg to about 2500 mg. In various embodiments, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the compounds of Formula (I) or Formula (II) will be regulated according to the judgment of the attending clinician considering such factors as age, condition and size of the patient as well as severity of the symptoms being treated. Generally, a total daily dosage of the compounds of Formula (I) or Formula (II) range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

EXAMPLES

The invention is illustrated by the following examples. For all of the examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

The following abbreviations are used herein:

| | |
|---|---|
| Ac | acetyl |
| Ac$_2$O | acetic anhydride |
| ACN | acetonitrile |
| AcOH or HOAc | acetic acid |
| APCI | atmospheric-pressure chemical ionization |
| aq | aqueous |
| Bn | benzyl |
| Boc or BOC | tert-butoxycarbonyl |
| Bz | benzoyl |
| Cbz | benzyloxycvarbonyl |
| calc'd | calculated |
| Celite | diatomaceous earth |
| DBU | 1,8-diazabicyclo(5.4.0)undec-7-ene |
| DCM | dichloromethane |
| DIEA or DIPEA | N,N-diisopropylethylamine |
| DMAP | 4-dimethylaminopyridine |
| DMF | N,N-dimethylformamide |
| DMSO | dimethyl sulfoxide |
| dMTrCl | 4,4'-dimethoxytrityl chloride |
| EDCI | 1-ethyl-3-(3-dimethylaminopropyl)carbodiimide |
| EDTA | ethylenediamine tetraacetic acid |
| ESI | electrospray ionization |
| Et | ethyl |
| Et$_2$O | diethyl ether |
| EtOH | ethanol |
| EtOAc | ethyl acetate |
| Et$_3$N | triethylamine |
| h | hour |
| HPLC | high-performance liquid chromatography |
| IPA | isopropanol |
| iPr | isopropyl |
| LC | liquid chromatography |
| LCMS | liquid chromatography mass spectrometry |
| Me | Methyl |
| MeCN | acetonitrile |
| MeOH | methanol |
| mg | milligrams |
| min | minute |
| μL | microliters |
| mL | milliliters |
| mmol | millimoles |
| MS | mass spectrometry |
| MTBE | methyl tert-butyl ether |
| MTS | (3-(4,5-dimethylthiazol-2-yl)-5-(3-carboxymethoxyphenyl)-2-(4-sulfophenyl)-2H-tetrazolium) |
| NMR | nuclear magnetic resonance spectroscopy |
| PDA | photodiode array |
| PE | petroleum ether |
| Ph | phenyl |
| Pr | Propyl |
| PS | Polystyrene |
| Rac | racemic mixture |
| Rh(COD)$_2$OTf | Bis(1,5-cyclooctadiene)rhodium(I) trifluoromethanesulfonate |
| Rosphos bistriflate | (+)-1,2-Bis[(2S,5S)-2,5-dimethyl-(3S,4S)-3,4-dihydroxyphospholano]benzene bis(trifluoromethanesulfonate)salt |
| RT | room temperature |
| Rt | retention time |
| Sat | saturated |
| SFC | supercritical fluid chromatography |
| TBAF | tert-butyl ammonium fluoride |
| TBS or TBDMS | tert-butyldimethylsilyl |
| TBSCL | tert-butyldimethylsilyl chloride |
| t-Bu | tert-butyl |
| TEA | triethylamine |
| TFA | trifluoroacetic acid |
| THF | tetrahydrofuran |
| TLC | thin layer chromatography |
| TMS | trimethylsilyl |
| Tris | tris(hydroxymethyl)aminomethane |
| UPLC | ultra-performance liquid chromatography |

General Procedures

Reactions sensitive to moisture or air were performed under nitrogen or argon atmosphere using anhydrous solvents and reagents. The progress of reactions was determined using either analytical thin layer chromatography (TLC) usually performed with E. Merck pre-coated TLC plates, silica gel 60F-254, layer thickness 0.25 mm or liquid chromatography-mass spectrometry (LC-MS).

The analytical UPLC-MS system used consisted of a Waters SQD2 platform with electrospray ionization in positive and negative detection mode with an Acquity UPLC I-class solvent manager, column manager, sample manager and PDA detector. The column used for standard methods was a CORTECS UPLC C18 1.6 μm, 2.1×30 mm, and the column used for polars method was an ACQUITY UPLC HSST3 1.8 μm, 2.1×30 mm, the column temperature was 40° C., the flow rate was 0.7 mL/min, and injection volume was 1 μL. UV detection was in the range 210-400 nm. The mobile phase consisted of solvent A (water plus 0.05% formic acid) and solvent B (acetonitrile plus 0.05% formic acid) with different gradients for 4 different methods: 1/Starting with 99% solvent A for 0.2 minutes changing to 98% solvent B over 1 minutes, maintained for 0.4 minutes, then reverting to 99% solvent A over 0.1 min; 2/Starting with 99% solvent A for 0.5 minutes changing to 98% solvent B over 3.7 minutes, maintained for 0.4 minutes, then reverting to 99% solvent A over 0.1 min; 3/Starting with 100% solvent A for 0.4 minutes changing to 98% solvent B over 0.9 minutes, maintained for 0.3 minutes, then reverting to 100% solvent A over 0.1 min; 4/Starting with 100% solvent A for 0.8 minutes changing to 98% solvent B over 3.4 minutes, maintained for 0.4 minutes, then reverting to 100% solvent A over 0.1 minutes.

The analytical LC-MS system used consisted of a Agilent 6140 quadrupole LC/MS platform with electrospray ionization in positive and negative detection mode with an Agilent 1200 Series solvent manager, column manager, sample manager and PDA detector. The column for standard method was Purospher® STAR RP-18 endcapped 2 μm, Hibar® HR 50-2.1, the column temperature was 60° C., the flow rate was 0.8 mL/min, and injection volume was 0.5-5 μL. UV detection was in the range 210-400 nm. The mobile phase consisted of solvent A (water plus 0.05% formic acid) and solvent B (acetonitrile plus 0.05% formic acid) with different gradients for 2 different methods: 1) Starting with 98% solvent A changing to 100% solvent B over 1.8 minutes, maintained for 0.8 min; 2) Starting with 98% solvent A changing to 100% solvent B over 5.8 minutes, maintained for 0.3 minutes.

Preparative HPLC purifications were usually performed using a mass spectrometry directed system. Usually they were performed on a Waters Chromatography Workstation (MassLynx V4.1) configured with LC-MS System Consisting of: Waters ZQ™ 2000 (quad MS system with Electrospray Ionization), Waters 2545 Gradient Pump, Waters 2767 Injecto/Collector, Waters 2998 PDA Detector, the MS Conditions of: 100-1400 amu, Positive Electrospray, Collection Triggered by MS, and a Waters SUNFIRE® C-18 5 micron, 19 mm (id)×150 mm column. The mobile phases consisted of mixtures of acetonitrile (5-95%) in water containing 0.02% formic acid. Flow rates were maintained at 20 mL/min, the injection volume was 500 to 3000 μL, and the UV detection range was 210-400 nm. Mobile phase gradients were optimized for the individual compounds. The analytical system consisted of the same system with a Waters SUNFIRE® C-18 5 μm, 4.6×150 mm column, or a XSelect® CSH™ C-18 5 μm, 4.6×150 mm column. The mobile phases consisted of mixtures of acetonitrile (5-95%) in water containing 0.02% formic acid. Flow rates were maintained at 1.2 mL/min, the injection volume was 5 to 20 μL. Preparative HPLC were also performed on a Gilson system GX-281 (Trilution). The column was a Waters SUNFIRE® Prep C18 5 μm OBD, dimension 50×150 mm. The mobile phase consisted of acetonitrile (5-50%) in water containing 0.02% HCOOH over 60 minutes. Flow rates were maintained at 117 mL/min, the injection volume was 1000 to 7000 μL, and the UV detection range was 260 nm.

Reactions performed using microwave irradiation were normally carried out using an Emrys Optimizer manufactured by Personal Chemistry, or an Initiator manufactured by Biotage. Concentration of solutions was carried out on a rotary evaporator in vacuo. Flash chromatography was usually performed using a Biotage® Flash Chromatography apparatus (Isolera) on silica gel (15-45μ, 40-63μ, or spheric silica) in pre-packed cartridges of the size noted. $^1$H NMR spectra were acquired at 400 MHz or 500 MHz spectrometers in $CDCl_3$ solutions unless otherwise noted. Chemical shifts were reported in parts per million (ppm). Tetramethylsilane (TMS) was used as internal reference in $CDCl_3$ solutions, and residual $CH_3OH$ peak or TMS was used as internal reference in $CD_3OD$ solutions. Coupling constants (J) were reported in hertz (Hz). Chiral analytical chromatography was performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of CHIRALPAK AS, of CHIRALPAK AD, CHIRALCEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

Preparation of Intermediate Compounds:

Preparation of Intermediate Compound A:

Method 1:

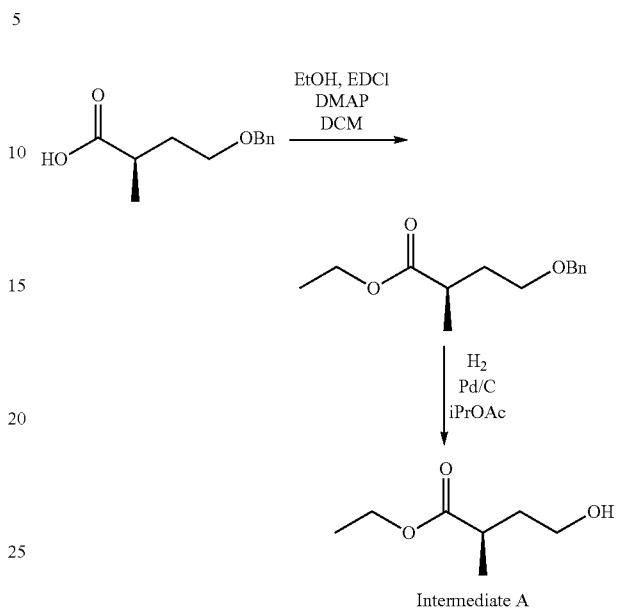

Intermediate A

Intermediate A: Ethyl (R)-4-hydroxy-2-methylbutanoate: Step 1: To a solution of (R)-4-(benzyloxy)-2-methylbutanoic acid (11.43 g, 54.95 mmol) in DCM (170 mL) were added N-(3-Dimethylaminopropyl)-N-ethylcarbodiimide hydrochloride (13.40 g, 70.16 mmol), 4-dimethylamino pyridine (0.69 g, 5.65 mmol) and ethanol (34 mL, 0.58 mol). The reaction mixture was stirred under nitrogen at RT overnight. The resulting reaction mixture was washed with water (100 mL). The organic layer was washed with a 10% solution of citric acid (100 mL) and with a 1:1 mixture of brine and water (100 mL), dried over sodium sulfate, filtered and concentrated under reduced pressure to afford ethyl (R)-4-(benzyloxy)-2-methylbutanoate. Step 2: To a suspension of palladium on carbon (1.64 g, 15.41 mmol) in isopropyl acetate (400 mL) was added a solution of ethyl (R)-4-(benzyloxy)-2-methylbutanoate (15.34 g, 65.00 mmol) in isopropyl acetate (50 mL). The reaction mixture was degassed few times with nitrogen. Then the flask was filled with hydrogen and it was stirred under an atmosphere of hydrogen for 7 h. The resulting reaction mixture was filtered through a pad of celite and washed with ethyl acetate (180 mL). The filtrates were concentrated under reduced pressure to afford the expected intermediate.

Method 2:

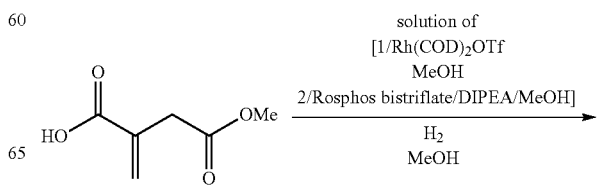

-continued

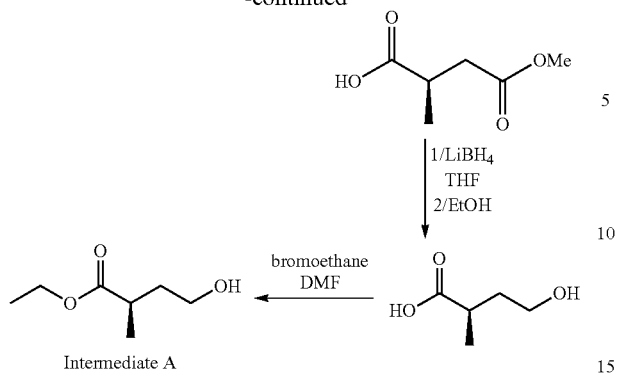

Intermediate A

Intermediate A: Ethyl (R)-4-hydroxy-2-methylbutanoate: Step 1: a/ In a glass autoclave, 4-methoxy-2-methylene-4-oxobutanoic acid (50 g, 0.347 mol) and methanol (70 mL) were stirred until complete dissolution. The system was then pump-fill degassed with nitrogen (3×). b/ To Rosphos bis-triflate (95 mg, 0.142 mmol) under $N_2$ was added methanol (1.5 mL, purged with $N_2$), followed by diisopropylethylamine (36.5 mg, 0.283 mmol) in methanol (0.5 mL). c/ To a solution of Rh(COD)$_2$OTf (63 mg, 0.135 mmol) purged with $N_2$ in methanol (1 mL, purged with $N_2$), cooled in an ice/methanol bath, was added dropwise over 2 min the phosphine solution prepared above. This solution was allowed to warm to RT, and then added to the autoclave, via syringe. The autoclave was took to 5 bar of hydrogen. The reaction mixture was stirred at 50° C. for 1 h, and then at 60° C. for 50 min. The system was allowed to cool to RT overnight. The resulting solution was transferred to an RBF with methanol, and concentrated under reduced pressure to afford the expected intermediate without further purification.

Step 2: To a solution of (R)-4-methoxy-2-methyl-4-oxobutanoic acid (52 g, 356 mmol) in THF (2 L) was added lithium borohydride (16.5 g, 712 mmol) portionwise over 40 min at RT. The reaction mixture was stirred at RT for 40 min, and then ethanol (400 mL) was added dropwise over 90 min. The reaction mixture was then stirred at RT overnight, and then concentrated under reduced pressure, azeotroping with THF to afford the expected intermediate used directly in the next step without further purification.

Step 3: To a suspension of previous intermediate in DMF (800 mL) was added bromoethane (270 mL, 3.6 mol). The reaction mixture was stirred for 2 days. The reaction mixture was extracted with MTBE and a pH 6.75 buffer (NaH$_2$PO$_4$.H$_2$O, 55.7 g; Na$_2$HPO$_4$.2H$_2$O, 61.6 g in 1 L of water), and then with brine. The organic layers were dried, filtered and concentrated under reduced pressure at 30° C. to afford the crude expected compound. This material was purified by column chromatography (DCM/EtOAc: 0 to 30%)

Preparation of Intermediate Compound B:

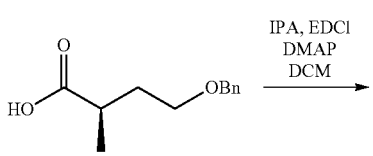

-continued

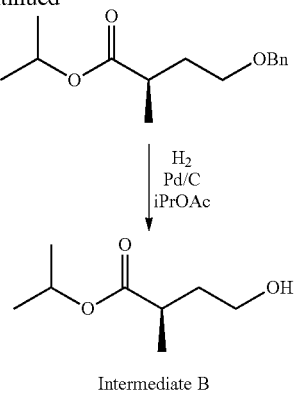

Intermediate B

Intermediate B: Isopropyl (R)-4-hydroxy-2-methylbutanoate: Step 1: To a stirred solution of (R)-4-(benzyloxy)-2-methylbutanoic acid (15.00 g, 72.00 mmol) in DCM (220 mL), was added isopropanol (55.2 mL, 0.72 mol) followed by the addition of a solution of N-(3-dimethylaminopropyl)-N-ethylcarbodiimide hydrochloride (16.60 g, 86.44 mmol) in DCM (100 mL). The reaction mixture was stirred, and then, 4-dimethylamino pyridine (0.88 g, 7.20 mmol) was added to the mixture. The reaction mixture was stirred under nitrogen at RT overnight. The resulting reaction mixture was washed with water (250 mL). The organic layer was washed with a 10% solution of citric acid (×2) and with brine, then it was dried over sodium sulfate, filtered and concentrated under reduced pressure to afford isopropyl (R)-4-(benzyloxy)-2-methylbutanoate. Step 2: To a suspension of palladium on carbon (3.30 g, 31.00 mmol) in isopropyl acetate (50 mL) was added a solution of isopropyl (R)-4-(benzyloxy)-2-methylbutanoate (16.50 g, 66.00 mmol) in isopropyl acetate (500 mL). The reaction mixture was degassed few times with nitrogen. Then the flask was filled with hydrogen and it was stirred under an atmosphere of hydrogen overnight. The reaction mixture was filtered through a pad of celite. The filtrates were concentrated under reduced pressure (water bath: 30° C.) and the resulting product was dried in vacuum oven for 4 h to afford the expected intermediate.

Preparation of Intermediate Compound C:

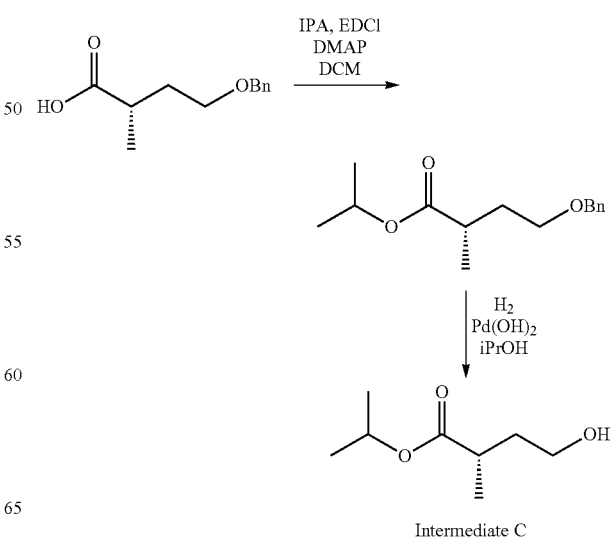

Intermediate C

Intermediate C: Isopropyl (S)-4-hydroxy-2-methylbutanoate: Step 1: To a stirred solution of (S)-4-(benzyloxy)-2-methylbutanoic acid (21.0 g, 101 mmol) in DCM (420 mL), was added isopropanol (38.5 mL, 504 mmol), N-(3-dimethylaminopropyl)-N-ethylcarbodiimide hydrochloride (23.20 g, 121 mmol) and 4-dimethylamino pyridine (1.23 g, 10.08 mmol). The reaction mixture was stirred under nitrogen at RT overnight. The resulting reaction mixture was washed with water (250 mL). The organic layer was washed with a 10% solution of citric acid (×2) and with brine, then it was dried over sodium sulfate, filtered and concentrated under reduced pressure to afford the expected intermediate; MS (ESI) m/z=251.3 (MH⁺). Step 2: To isopropyl (S)-4-(benzyloxy)-2-methylbutanoate (25.3 g, 101 mmol) was added propan-2-ol (500 mL) and dihydroxypalladium (2.13 g, 15.15 mmol). The reaction mixture was degassed few times with nitrogen. Then the flask was filled with hydrogen and the reaction mixture was stirred under an atmosphere of hydrogen for 9 h. The reaction mixture was filtered through a pad of celite. The filtrates were concentrated under reduced pressure (water bath: 30° C.) to afford the expected intermediate; $^1$H NMR (CDCl$_3$, 400 MHz) δ (ppm) 4.99 (heptuplet, J=6.24 Hz, 1H), 3.70-3.61 (m, 2H), 2.60-2.51 (m, 1H), 1.94-1.85 (m, 1H), 1.70-1.62 (m, 1H), 1.22-1.20 (m, 6H), 1.15 (d, J=7.00 Hz, 3H); MS (ESI) m/z=183.0 (MNa⁺).

Preparation of Intermediate Compound D:

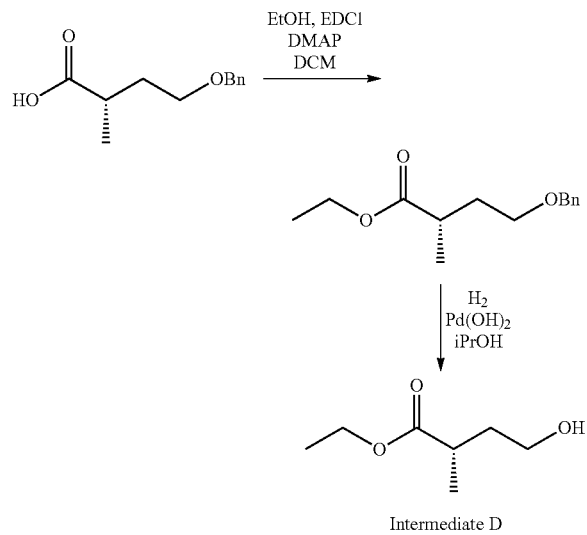

Intermediate D

Intermediate D: Ethyl (S)-4-hydroxy-2-methylbutanoate: Step 1: To a solution of (S)-4-(benzyloxy)-2-methylbutanoic acid (30.0 g, 144 mmol) in DCM (600 mL) were added N-(3-Dimethylaminopropyl)-N-ethylcarbodiimide hydrochloride (33.1 g, 173 mmol), 4-dimethylamino pyridine (1.76 g, 14.41 mmol) and ethanol (42.1 mL, 720 mmol). The reaction mixture was stirred under nitrogen at RT overnight. The resulting reaction mixture was washed with water (250 mL). The organic layer was washed with a 10% solution of citric acid (250 mL) and with brine, and then filtered through a phase separator and concentrated under reduced pressure to afford the expected intermediate; MS (ESI) m/z=237.1 (MH⁺). Step 2: To a solution of ethyl (S)-4-(benzyloxy)-2-methylbutanoate (29.5 g, 125 mmol) in ethanol (624 mL) was added dihydroxypalladium (2.63 g, 18.73 mmol). The reaction mixture was degassed few times with nitrogen. Then the flask was filled with hydrogen and the reaction mixture was stirred under an atmosphere of hydrogen for 9 h. The reaction mixture was filtered through a pad of celite. The filtrates were concentrated under reduced pressure to afford the expected intermediate; $^1$H NMR (CDCl$_3$, 400 MHz) δ (ppm) 4.04 (q, J=7.09 Hz, 2H), 3.56 (t, J=6.40 Hz, 2H), 2.57-2.48 (m, 1H), 1.81-1.79 (m, 1H), 1.61-1.53 (m, 1H), 1.18 (t, J=7.09 Hz, 3H), 1.09 (d, J=6.99 Hz, 3H).

Preparation of Intermediate Compounds E and F:

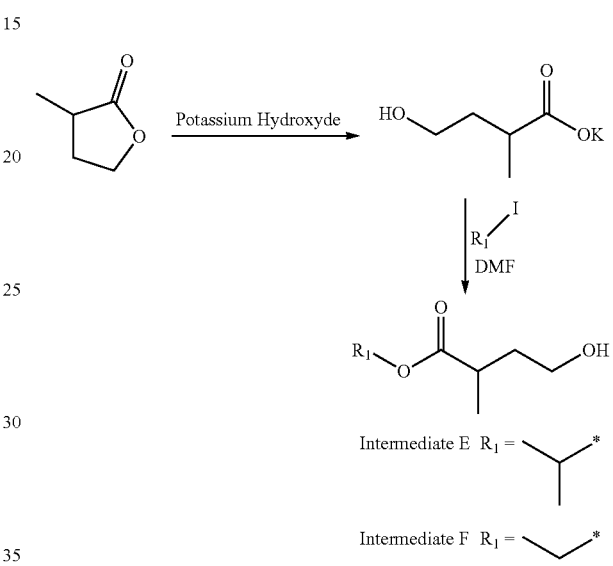

Intermediate E: Isopropyl 4-hydroxy-2-methylbutanoate: Step 1: A solution of α-methyl-γ-butyrolactone (50.0 g, 499 mmol) in 1M aqueous potassium hydroxide solution (499 mL, 499 mmol) was stirred under reflux for 3 hours, then cooled to RT and concentrated under reduced pressure. The crude solid was triturated in diethyl ether, filtered off and washed with diethyl ether. The solid was then dried in vacuo over P$_2$O$_5$ at 45° C. Step 2: To a solution of the product of step 1 (25.0 g, 160.0 mmol) in DMF (200 mL) was added dropwise at RT under nitrogen 2-iodopropane (31.9 mL, 320 mmol). The reaction mixture was stirred at RT for 5 h. 2-iodopropane (8.0 mL, 80 mmol) was added, and the reaction mixture was stirred at RT overnight. The mixture was diluted with EtOAc, and the organic layer was washed with a metabisulfite solution and brine. The organic layer was dried, filtered and concentrated under reduced pressure at 20-30° C. to provide the expected intermediate. $^1$H NMR (400 MHz, CDCl$_3$) δ 4.97 (heptuplet, J=6.23 Hz, 1H), 3.66-3.60 (m, 2H), 2.59-2.50 (m, 1H), 1.92-1.84 (m, 1H), 1.67-1.59 (m, 1H), 1.195 (d, J=6.23 Hz, 3H), 1.19 (d, J=6.23 Hz, 3H), 1.14 (d, J=7.09 Hz, 3H).

Intermediate F: Intermediate F was synthesized using the method described for the synthesis of intermediate compound E starting for step 2 from iodoethane (1.2 eq.). $^1$H NMR (400 MHz, CDCl$_3$) δ 4.14 (q, J=7.11 Hz, 2H), 3.69-3.63 (m, 2H), 2.67-2.58 (m, 1H), 1.98-1.89 (m, 1H), 1.71-1.63 (m, 1H), 1.26 (t, J=7.11 Hz, 3H), 1.19 (d, J=7.10 Hz, 3H).

Example 1

Preparation of Compounds 1A and 1B

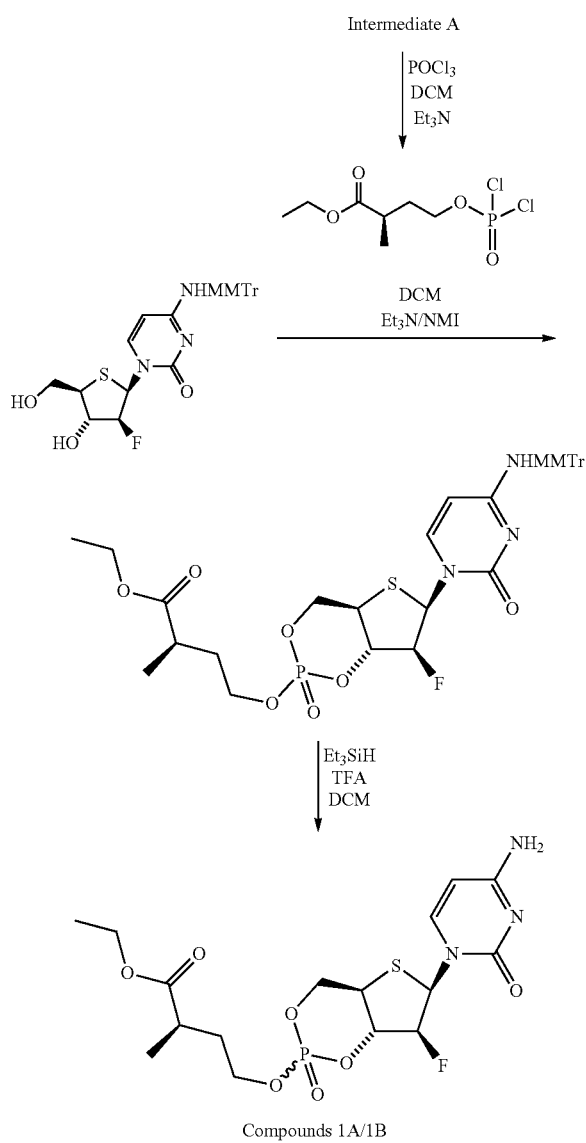

Compounds 1A/1B: Ethyl (R)-4-(((2S,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)oxy)-2-methylbutanoate and Ethyl (R)-4-(((2R,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)oxy)-2-methylbutanoate Step 1: A solution of phosphorus (V) oxychloride (0.12 mL, 1.29 mmol) in anhydrous DCM (4 mL) was cooled to −20° C. A solution of intermediate A (171 mg, 1.17 mmol) and triethylamine (0.18 mL, 1.29 mmol) in anhydrous DCM (3 mL) was added to the previous solution dropwise at −20° C. The reaction mixture was stirred at −25° C. for 64 h. The resulting reaction mixture was warmed to RT and solvent was removed in vacuo at 30° C. Diethyl ether was added to the residue, filtered and concentrated under reduced pressure to afford the expected intermediate, which was used in the next step without further purification.

Step 2: To a solution of previous intermediate of step 1 in DCM (10 mL) was added dropwise a solution of 1-((2R,3S,4S,5R)-3-fluoro-4-hydroxy-5-(hydroxymethyl)tetrahydrothiophen-2-yl)-4-(((4-methoxyphenyl)diphenylmethyl)amino)pyrimidin-2(1H)-one (500 mg, 0.94 mmol) and triethylamine (0.45 mL, 3.23 mmol) in DCM (3 mL). The reaction mixture was stirred for 30 min at RT, and then, a solution of 1-methylimidazole (77 mg, 0.94 mmol) in DCM (0.5 mL) was added. The reaction mixture was stirred at RT overnight, and then, concentrated under reduced pressure. The crude residue was dissolved in ethyl acetate (100 mL) and the resulting solution was washed with brine. The organic layer was dried over sodium sulfate, filtered and concentrated under reduced pressure. The crude compound was purified via silica gel flash column chromatography (DCM/EtOAc 50%) to afford the 2 expected isomers Sp and Rp. Diastereoisomer 1: MS (ESI) m/z=723.8 (MH$^+$); Diastereoisomer 2: MS (ESI) m/z=723.6 (MH$^+$).

Step 3: To a solution of diastereoisomer 1 of ethyl (2R)-4-(((4aR,6R,7S,7aS)-7-fluoro-6-(4-(((4-methoxyphenyl)diphenylmethyl)amino)-2-oxopyrimidin-1(2H)-yl)-2-oxidotetrahydro-4H-thieno[3,2-d][1,3,2]dioxaphosphinin-2-yl)oxy)-2-methylbutanoate (40 mg, 55 μmol) in DCM (5 mL) was added triethylsilane (0.5 mL). A solution of trifluoroacetic acid (0.5 mL) in DCM (5 mL) was added dropwise to the reaction mixture. The reaction mixture was stirred at RT for 90 min. Solvent was removed under reduced pressure and the residue was azeotroped with toluene (×2) (30° C. bath). The crude residue was purified via silica gel flash column chromatography (DCM/EtOH 0-10%) to afford the expected isomer.

Compound 1 Diastereoisomer 1: $^1$H NMR (DMSO-d$_6$, 400 MHz) δ (ppm) 8.13 (d, J=7.61 Hz, 1H), 7.47-7.41 (m, 2H), 6.62-6.61 (m, 1H), 5.81 (d, J=7.61 Hz, 1H), 5.51-5.33 (m, 1H), 5.29-5.20 (m, 1H), 4.69-4.58 (m, 2H), 4.15-4.04 (m, 2H), 4.07 (q, J=7.03 Hz, 2H), 3.72-3.66 (m, 1H), 2.59-2.53 (m, 1H), 1.99-1.90 (m, 1H), 1.75-1.67 (m, 1H), 1.19 (t, J=7.03 Hz, 3H), 1.11 (d, J=7.17 Hz, 3H); $^{31}$P NMR (DMSO-d$_6$, 162 MHz) δ (ppm) −6.59 (s, 1P); $^{19}$F NMR (DMSO-d$_6$, 376 MHz) δ (ppm) −198.26 (s, 1F); MS (ESI) m/z=452.4 (MH$^+$).

Step 3 bis: To a solution of diastereoisomer 2 of ethyl (2R)-4-(((4aR,6R,7S,7aS)-7-fluoro-6-(4-(((4-methoxyphenyl)diphenylmethyl)amino)-2-oxopyrimidin-1(2H)-yl)-2-oxidotetrahydro-4H-thieno[3,2-d][1,3,2]dioxaphosphinin-2-yl)oxy)-2-methylbutanoate (35 mg, 48 μmol) in DCM (5 mL) was added triethylsilane (0.5 mL). A solution of trifluoroacetic acid (0.5 mL) in DCM (5 mL) was added dropwise to the reaction mixture. The reaction mixture was stirred at RT for 2 h. Solvent was removed under reduced pressure and the residue was azeotroped with toluene (×2) (30° C. bath). The crude residue was purified via silica gel flash column chromatography (DCM/EtOH 0-10%) to afford the expected isomer.

Compound 1 Diastereoisomer 2: $^1$H NMR (DMSO-d$_6$, 400 MHz) δ (ppm) 8.03 (d, J=7.41 Hz, 1H), 7.35 (brs, 2H), 6.66-6.63 (m, 1H), 5.81 (d, J=7.41 Hz, 1H), 5.52-5.35 (m, 1H), 4.98-4.89 (m, 1H), 4.70-4.60 (m, 1H), 4.47-4.40 (m, 1H), 4.12-4.05 (m, 4H), 3.69-3.63 (m, 1H), 2.64-2.61 (m, 1H), 2.06-1.97 (m, 1H), 1.86-1.78 (m, 1H), 1.18 (t, J=7.06 Hz, 3H), 1.13 (d, J=7.08 Hz, 3H); $^{31}$P NMR (DMSO-d$_6$, 162 MHz) δ (ppm) −7.99 (s, 1P); $^{19}$F NMR (DMSO-d$_6$, 376 MHz) δ (ppm) −197.94 (s, 1F); MS (ESI) m/z=452.3 (MH$^+$).

Example 2

Preparation of Compounds 2A and 2B

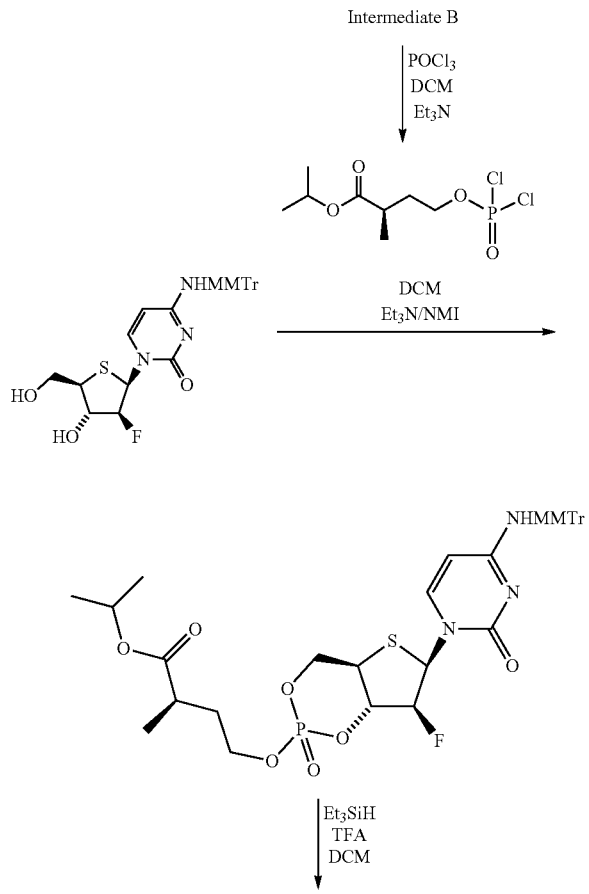

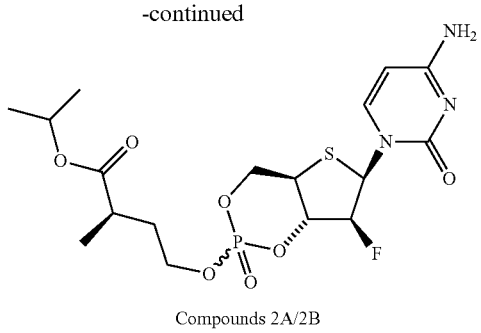

Compounds 2A/2B

Compounds 2A/2B: Isopropyl (R)-4-(((2S,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)oxy)-2-methylbutanoate and Isopropyl (R)-4-(((2R,4aR,6R,7S,7aS)-6-(4-amino-2-oxopyrimidin-1(2H)-yl)-7-fluoro-2-oxidotetrahydro-4H-thieno[3,2-d][1,3,2]dioxaphosphinin-2-yl)oxy)-2-methylbutanoate Compounds 2A/2B were synthesized according to a similar procedure than the procedure described for Compounds 1A/1B using Intermediate B as starting material.

Compound 2 Diastereoisomer 1: $^1$H NMR (DMSO-d$_6$, 400 MHz) δ (ppm) 9.01 (brs, 1H), 8.45-8.42 (m, 2H), 6.49 (d, J=7.96 Hz, 1H), 6.03 (d, J=7.83 Hz, 1H), 5.58-5.41 (m, 1H), 5.25-5.17 (m, 1H), 4.89 (heptuplet, J=6.26 Hz, 1H), 4.72-4.60 (m, 2H), 4.13-4.06 (m, 2H), 3.72-3.66 (m, 1H), 2.53-2.52 (m, 1H), 1.98-1.89 (m, 1H), 1.74-1.66 (m, 1H), 1.185 (d, J=6.26 Hz, 3H), 1.18 (d, J=6.26 Hz, 3H), 1.10 (d, J=7.05 Hz, 3H); $^{31}$P NMR (DMSO-d$_6$, 162 MHz) δ (ppm) −6.53 (s, 1P); $^{19}$F NMR (DMSO-d$_6$, 376 MHz) δ (ppm) −198.18 (s, 1F); MS (ESI) m/z=466.5 (MH$^+$).

Compound 2 Diastereoisomer 2: $^1$H NMR (DMSO-d$_6$, 400 MHz) δ (ppm) 8.48 (brs, 1H), 8.26 (d, J=7.65 Hz, 1H), 8.07 (brs, 1H), 6.55 (d, J=8.09 Hz, 1H), 5.97 (d, J=7.65 Hz, 1H), 5.58-5.41 (m, 1H), 4.96-4.87 (m, 2H), 4.72-4.62 (m, 1H), 4.44 (t, J=10.50 Hz, 1H), 4.13-4.05 (m, 2H), 3.70-3.63 (m, 1H), 2.62-2.55 (m, 1H), 2.05-1.97 (m, 1H), 1.84-1.76 (m, 1H), 1.18 (d, J=6.28 Hz, 3H), 1.175 (d, J=6.28 Hz, 3H), 1.11 (d, J=7.0 Hz, 3H); $^{31}$P NMR (DMSO-d$_6$, 162 MHz) δ (ppm) −8.04 (s, 1P); $^{19}$F NMR (DMSO-d$_6$, 376 MHz) δ (ppm) −197.83 (s, 1F); MS (ESI) m/z=466.5 (MH$^+$).

Example 3

Preparation of Compounds 3A and 3B 1-chloro-N,N,N′,N′-tetraisopropylphosphinediamine

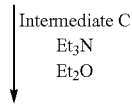

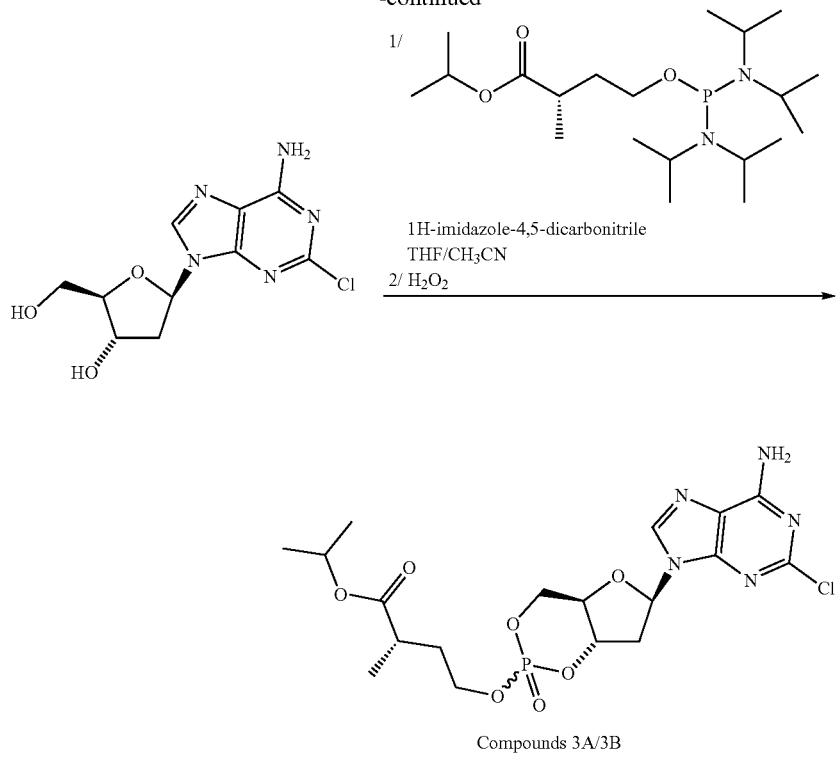

Compounds 3A/3B

Compounds 3A/3B: Isopropyl (S)-4-(((2S,4aR,6R,7aS)-6-(6-amino-2-chloro-9H-purin-9-yl)-2-oxidotetrahydro-4H-furo[3,2-d][1,3,2]dioxaphosphinin-2-yl)oxy)-2-methylbutanoate and Isopropyl (S)-4-(((2R,4aR,6R,7aS)-6-(6-amino-2-chloro-9H-purin-9-yl)-2-oxidotetrahydro-4H-furo[3,2-d][1,3,2]dioxaphosphinin-2-yl)oxy)-2-methylbutanoate Step 1: To a −15° C. solution of 1-chloro-N,N,N',N'-tetraisopropylphosphinediamine (15 g, 56.2 mmol) and triethylamine (7.84 mL, 56.2 mmol) in diethyl ether (187 mL), under nitrogen, was added dropwise a solution of isopropyl (S)-4-hydroxy-2-methylbutanoate (9.01 g, 56.2 mmol) in diethyl ether (94 mL). The reaction mixture was stirred at −15° C. for 1 h and then at RT for 2 h. The resulting suspension was filtered under nitrogen and washed with diethyl ether. The filtrate was concentrated in vacuo at RT under nitrogen to provide a crude intermediate compound, which was stored at −20° C. under nitrogen and was directly used in the next step without further purification: $^{31}$P NMR (162 MHz, CDCl$_3$) δ 124.0 (s, 1P).

Step 2: To a solution of THF (3.2 mL) under nitrogen at RT were simultaneously slowly added a solution of (2R,3S,5R)-5-(6-amino-2-chloro-9H-purin-9-yl)-2-(hydroxymethyl)tetrahydrofuran-3-ol (400 mg, 1.4 mmol) and 1H-imidazole-4,5-dicarbonitrile (413 mg, 3.5 mmol) (coevaporated 3 times with CH$_3$CN and THF) in THF (10.2 mL) and CH$_3$CN (5.1 mL), and a solution of the intermediate compound of step 1 (729 mg, 1.68 mmol) in THF (3.2 mL). The reaction mixture was stirred at RT overnight. Hydrogen peroxide (0.21 mL, 7.0 mmol) was then added dropwise at RT for 15 min. The reaction mixture was stirred at RT for 3 hours, and then, diluted with EtOAc and water. The aqueous layer was washed twice with EtOAc. The combined organic layers were washed with brine, dried, and concentrated under reduced pressure. The crude residue was purified by flash chromatography on silica gel (DCM/MeOH: 0 to 10%) followed by preparative MS/HPLC to afford the 2 title compounds (isolated diasteromers at P).

Compound 3 Diastereoisomer 1: $^1$H NMR (DMSO-d$_6$, 400 MHz) δ (ppm) 8.38 (s, 1H), 7.90 (brs, 2H), 6.46-6.43 (m, 1H), 5.32-5.26 (m, 1H), 4.89 (heptuplet, J=6.25 Hz, 1H), 4.61 (ddd, J=21.97 Hz, 9.26 Hz, 4.63 Hz, 1H), 4.34-4.29 (m, 1H), 4.18-4.09 (m, 2H), 4.05-3.99 (m, 1H), 2.80-2.76 (m, 2H), 2.68-2.59 (m, 1H), 2.09-2.00 (m, 1H), 1.86-1.78 (m, 1H), 1.16 (d, J=6.25 Hz, 6H), 1.13 (d, J=7.00 Hz, 3H); $^{31}$P NMR (DMSO-d$_6$, 162 MHz) δ (ppm) −6.61 (s, 1P); MS (ESI) m/z=490.3 (MH$^+$).

Compound 3 Diastereoisomer 2: $^1$H NMR (DMSO-d$_6$, 400 MHz) δ (ppm) 8.46 (s, 1H), 7.89 (brs, 2H), 6.48-6.45 (m, 1H), 5.33-5.26 (m, 1H), 4.91 (heptuplet, J=6.33 Hz, 1H), 4.66-4.59 (m, 1H), 4.47-4.40 (m, 1H), 4.16-4.06 (m, 3H), 2.83-2.72 (m, 2H), 2.57-2.53 (m, 1H), 2.01-1.92 (m, 1H), 1.76-1.68 (m, 1H), 1.21 (d, J=6.33 Hz, 3H), 1.20 (d, J=6.33 Hz, 3H), 1.12 (d, J=7.06 Hz, 3H); $^{31}$P NMR (DMSO-d$_6$, 162 MHz) δ (ppm) −4.93 (s, 1P); MS (ESI) m/z=490.3 (MH$^+$).

Example 4

Preparation of Compounds 4A and 4B

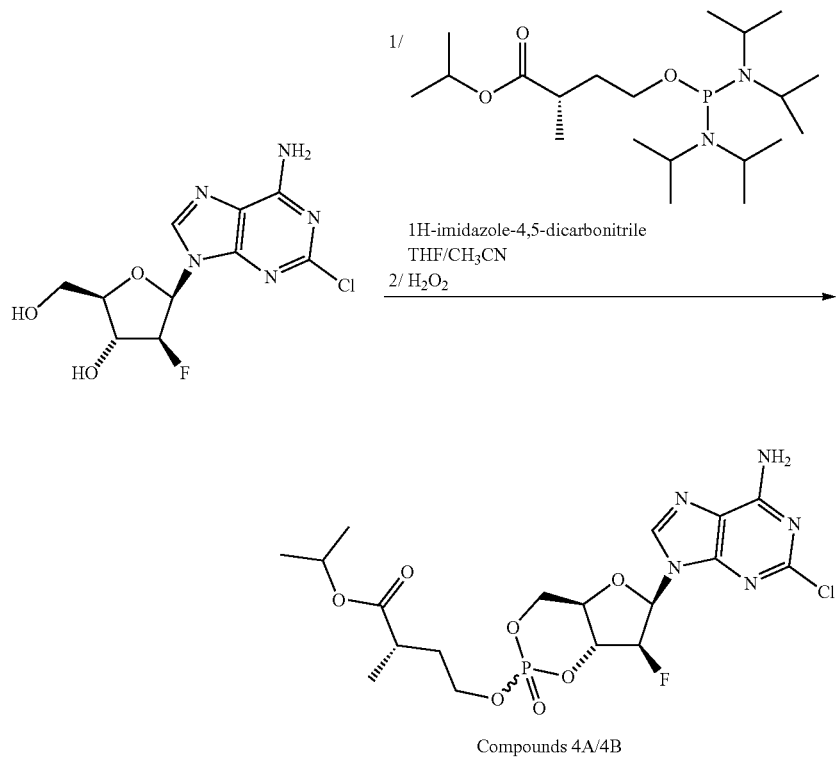

Compounds 4A/4B

Compounds 4A/4B: Isopropyl (S)-4-(((2S,4aR,6R,7S,7aR)-6-(6-amino-2-chloro-9H-purin-9-yl)-7-fluoro-2-oxidotetrahydro-4H-furo[3,2-d][1,3,2]dioxaphosphinin-2-yl)oxy)-2-methylbutanoate and Isopropyl (S)-4-(((2R,4aR,6R,7S,7aR)-6-(6-amino-2-chloro-9H-purin-9-yl)-7-fluoro-2-oxidotetrahydro-4H-furo[3,2-d][1,3,2]dioxaphosphinin-2-yl)oxy)-2-methylbutanoate Compounds 4A/4B were synthesized according to a similar procedure than the procedure described for Compounds 3A/3B using (2R,3R,4S,5R)-5-(6-amino-2-chloro-9H-purin-9-yl)-4-fluoro-2-(hydroxymethyl)tetrahydrofuran-3-ol as starting material.

Compound 4 Diastereoisomer 1: $^1$H NMR (DMSO-d$_6$, 400 MHz) δ (ppm) 8.43 (s, 1H), 7.98 (brs, 2H), 6.63-6.60 (m, 1H), 5.96-5.79 (m, 1H), 5.60-5.50 (m, 1H), 4.90 (heptuplet, J=6.29 Hz, 1H), 4.75-4.66 (m, 1H), 4.50-4.46 (m, 1H), 4.24-4.13 (m, 3H), 2.65-2.58 (m, 1H), 2.11-2.03 (m, 1H), 1.87-1.79 (m, 1H), 1.18 (d, J=6.29 Hz, 6H), 1.12 (d, J=7.06 Hz, 3H); $^{31}$P NMR (DMSO-d$_6$, 162 MHz) δ (ppm) −6.92 (s, 1P); $^{19}$F NMR (DMSO-d$_6$, 376 MHz) δ (ppm) −200.16 (s, 1F); MS (ESI) m/z=508.3 (MH$^+$).

Compound 4 Diastereoisomer 2: $^1$H NMR (DMSO-d$_6$, 400 MHz) δ (ppm) 8.54-8.53 (m, 1H), 7.98 (brs, 2H), 6.65-6.62 (m, 1H), 5.92-5.74 (m, 1H), 5.67-5.57 (m, 1H), 4.91 (heptuplet, J=6.33 Hz, 1H), 4.74-4.67 (m, 1H), 4.61-4.54 (m, 1H), 4.32-4.26 (m, 1H), 4.18-4.09 (m, 2H), 2.57-2.54 (m, 1H), 2.02-1.93 (m, 1H), 1.78-1.69 (m, 1H), 1.205 (d, J=6.33 Hz, 3H), 1.20 (d, J=6.33 Hz, 3H), 1.12 (d, J=7.03 Hz, 3H); $^{31}$P NMR (DMSO-d$_6$, 162 MHz) δ (ppm) −5.20 (s, 1P); $^{19}$F NMR (DMSO-d$_6$, 376 MHz) δ (ppm) −199.57 (s, 1F); MS (ESI) m/z=508.3 (MH$^+$).

Example 5

Preparation of Compounds 5A and 5B

Intermediate B  →  1-chloro-N,N,N',N'-tetraisopropylphosphinediamine
Et$_3$N
Et$_2$O

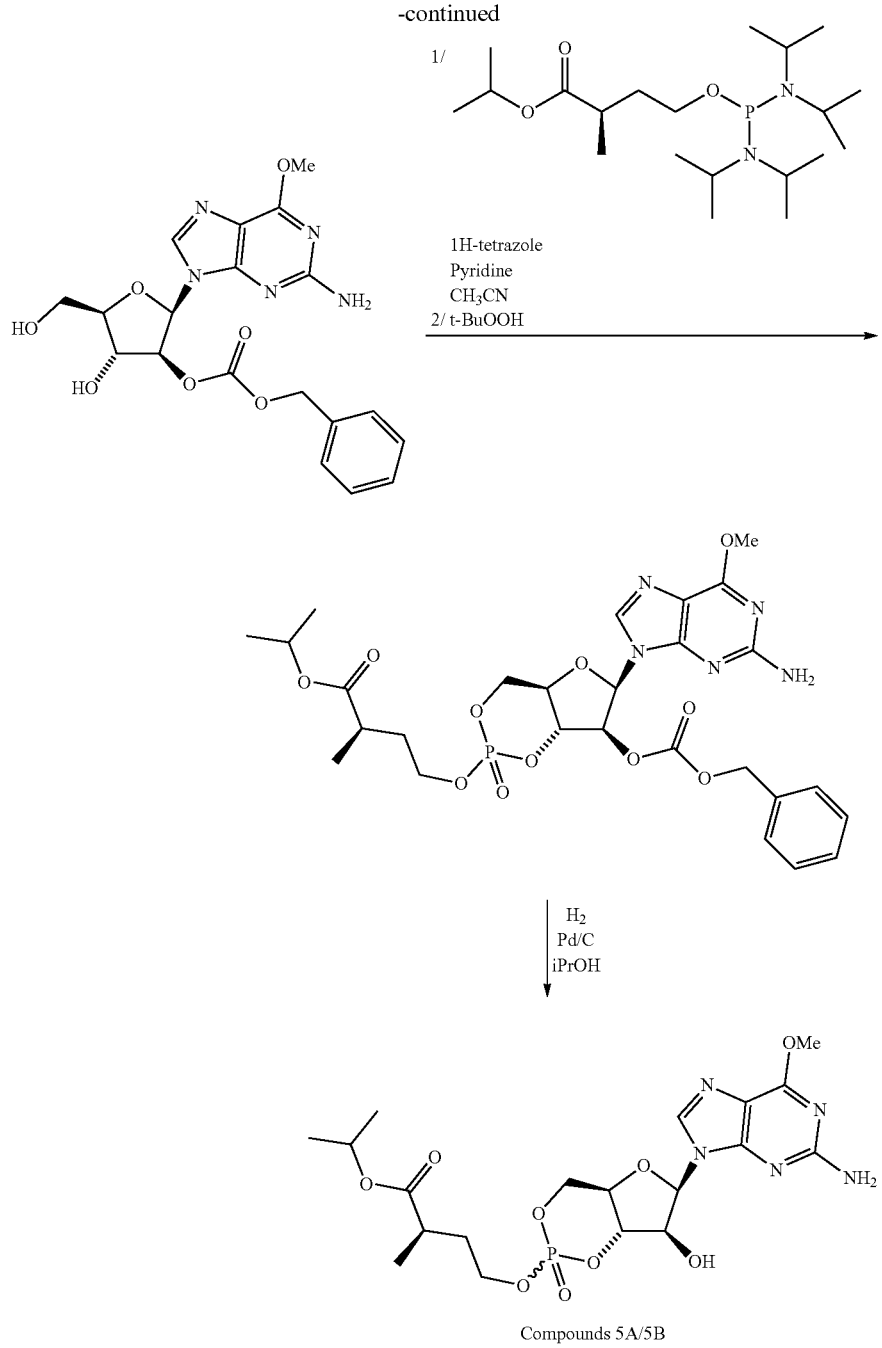

Compounds 5A/5B: Isopropyl (R)-4-(((2S,4aR,6R, 7S,7aS)-6-(2-amino-6-methoxy-9H-purin-9-yl)-7-hydroxy-2-oxidotetrahydro-4H-furo[3,2-d][1,3,2]dioxaphosphinin-2-yl)oxy)-2-methylbutanoate and Isopropyl (R)-4-(((2R,4aR,6R,7S,7aS)-6-(2-amino-6-methoxy-9H-purin-9-yl)-7-hydroxy-2-oxidotetrahydro-4H-furo[3,2-d][1,3,2]dioxaphosphinin-2-yl)oxy)-2-methylbutanoate Step 1: was similar than the procedure described for Step 1 of Compounds 3A/3B using Intermediate B as starting material. $^{31}$P NMR (162 MHz, CDCl$_3$) δ 123.89 (s, 1P).

Step 2: To a solution of (2R,3S,4R,5R)-2-(2-amino-6-methoxy-9H-purin-9-yl)-4-hydroxy-5-(hydroxymethyl)tetrahydrofuran-3-yl benzyl carbonate (500 mg, 1.16 mmol) in anhydrous pyridine (11 mL, 9.5 mL/mmol) was added under nitrogen at RT 1H-tetrazole (11 mL, 9.5 mL/mmol). The reaction mixture was cooled to −5° C. and a solution of the intermediate compound of step 1 (453 mg, 1.16 mmol) in CH$_3$CN (5 mL) was added dropwise. The reaction mixture was stirred at 0° C. for 1 h and then at RT for 2 h. The reaction was monitored by LC/MS. A solution of tert-butylhydroperoxide, 5M in decane (0.6 mL, 0.5 mL/mmol) was then added dropwise and the resulting reaction mixture was allowed to stir for 1 h at RT. The crude reaction mixture was concentrated under reduced pressure. The crude residue was purified using flash chromatography on silica gel (DCM/MeOH: 0 to 10%) to afford the intermediate compound as a mixture of diastereomers.

Step 3: To a solution of isopropyl (2R)-4-(((4aR,6R,7S,7aR)-6-(2-amino-6-methoxy-9H-purin-9-yl)-7-(((benzyloxy)carbonyl)oxy)-2-oxidotetrahydro-4H-furo[3,2-d][1,3,2]dioxaphosphinin-2-yl)oxy)-2-methylbutanoate (468 mg, 0.74 mmol) in propan-2-ol (5 mL) was added palladium on carbon (78 mg, 0.74 mmol). The reaction mixture was degassed few times with nitrogen. Then the flask was filled with hydrogen and the reaction mixture was stirred under hydrogen for 3 h. The reaction mixture was filtered through a pad of celite. The filtrate was concentrated under reduced pressure and purified by RP-18 chromatography ($H_2O$/$CH_3CN$) to afford the expected compound as a mixture of diastereoisomers.

Compound 5: Mixture of Diastereoisomers 5A/5B: $^1$H NMR (DMSO-$d_6$, 400 MHz) δ (ppm) 8.07 (s, 0.5H), 8.05 (s, 0.5H), 6.47 (brs, 2H), 6.31-6.29 (m, 1H), 6.07-6.04 (m, 1H), 5.04-4.99 (m, 0.5H), 4.95-4.87 (m, 1H), 4.74-4.66 (m, 1.5H), 4.62-4.44 (m, 2H), 4.20-4.03 (m, 3H), 3.96 (s, 3H), 2.63-2.55 (m, 1H), 2.09-1.91 (m, 1H), 1.86-1.68 (m, 1H), 1.21-1.18 (m, 6H), 1.15-1.10 (m, 3H); $^{31}$P NMR (DMSO-$d_6$, 162 MHz) δ (ppm) −4.87 (s, 0.5P), −6.40 (s, 0.5P); MS (ESI) m/z=502.2 (MH$^+$).

Example 6

Preparation of Compounds 6A and 6B

Compounds 6A/6B: Isopropyl 4-(((2S,4aR,6R,7aS)-6-(2,4-dioxo-5-(trifluoromethyl)-3,4-dihydropyrimidin-1(2H)-yl)-2-oxidotetrahydro-4H-furo[3,2-d][1,3,2]dioxaphosphinin-2-yl)oxy)-2-methylbutanoate and Isopropyl 4-(((2R,4aR,6R,7aS)-6-(2,4-dioxo-5-(trifluoromethyl)-3,4-dihydropyrimidin-1(2H)-yl)-2-oxidotetrahydro-4H-furo[3,2-d][1,3,2]dioxaphosphinin-2-yl)oxy)-2-methylbutanoate Compounds 6A/6B were synthesized according to a similar procedure than the procedure described for Compounds 3A/3B using 1-((2R,4S,5R)-4-hydroxy-5-(hydroxymethyl)tetrahydrofuran-2-yl)-5-(trifluoromethyl)pyrimidine-2,4(1H,3H)-dione and Intermediate E as starting materials.

Compound 6: Mixture of Diastereoisomers 6A/6B: $^1$H NMR (DMSO-$d_6$, 400 MHz) δ (ppm) 12.00 (brs, 1H), 8.16 (s, 0.1H), 8.13 (s, 0.9H), 6.23-6.17 (m, 1H), 4.90 (heptuplet, J=6.28 Hz, 1H), 4.85-4.77 (m, 1H), 4.67-4.59 (m, 1H), 4.41-4.36 (m, 1H), 4.13-4.03 (m, 2H), 3.98-3.92 (m, 1H), 2.65-2.55 (m, 2H), 2.04-1.92 (m, 1H), 1.82-1.71 (m, 1H), 1.19 (d, J=6.28 Hz, 6H), 1.12 (d, J=7.00 Hz, 3H); $^{31}$P NMR (DMSO-$d_6$, 162 MHz) δ (ppm) −4.84 (s, 0.1P), −6.69 (s, 0.9P); $^{19}$F NMR (DMSO-$d_6$, 376 MHz) (ppm) −61.43 (s, 0.1F), −61.58-(−61.59) (s, 0.9F); MS (ESI) m/z=523.2 (MNa$^+$).

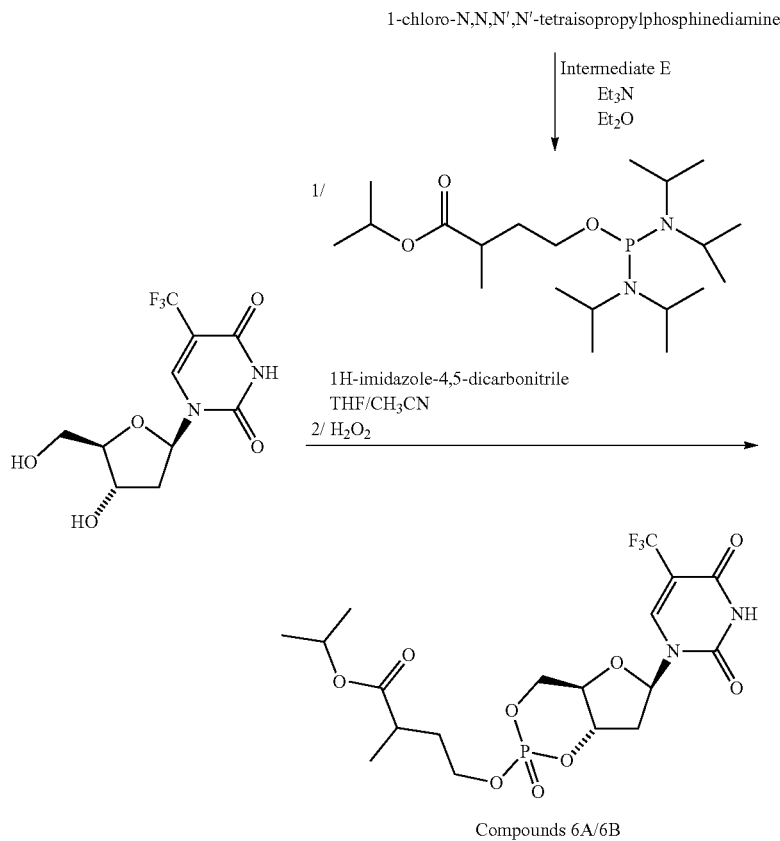

Compounds 6A/6B

Example 7

Preparation of Compounds 7A and 7B

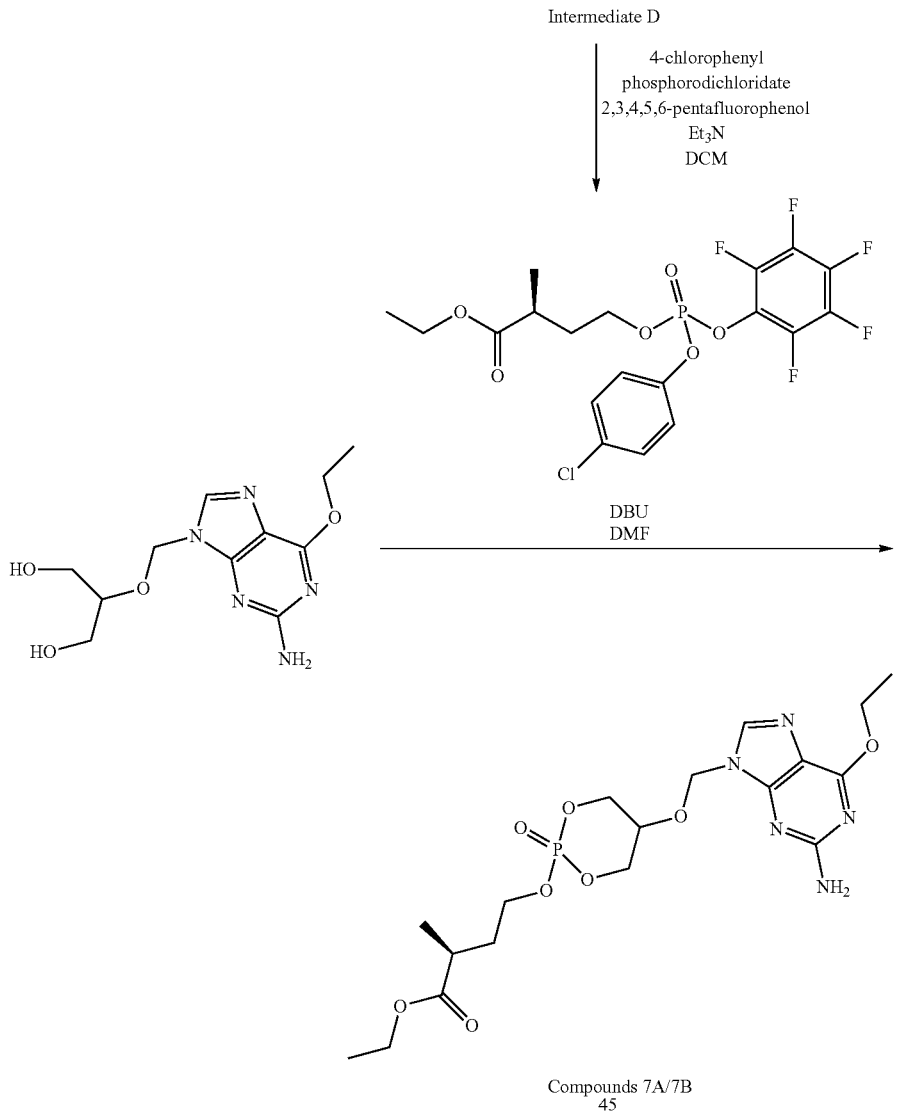

Compounds 7A/7B

Step 1: To a solution of 2,3,4,5,6-pentafluorophenol (2.77 g, 15.05 mmol) in DCM (25 mL) were added at −75° C. a solution of 4-chlorophenyl phosphodichloridate (3.69 g, 15.05 mmol) in DCM (25 mL), followed by triethylamine (2.01 mL, 15.05 mmol) dropwise. The reaction mixture was stirred at −75° C. for 30 min, then allowed to warm up to 0° C. A solution of intermediate D (2.5 g, 15.05 mmol) in DCM (25 mL) was then added followed by triethylamine (4.20 mL, 30.10 mmol) dropwise. The reaction mixture was stirred at RT for 1 h and then concentrated under reduced pressure. $^{31}$P NMR (DMSO-$d_6$, 162 MHz) δ (ppm) −11.57 (s, 1P).

Step 2: To a solution of 2-((2-amino-6-ethoxy-9H-purin-9-yl)methoxy)propane-1,3-diol (50 mg, 0.18 mmol) in DMF (880 µL) under nitrogen was added DBU (80 µL, 0.53 mmol). After stirring for 10 min, a solution of intermediate of step 1 (89 mg, 0.18 mmol) in DMF (880 µL) was then added dropwise at −10° C. The reaction mixture was stirred at 140° C. under microwaves irradiation for 20 min. The reaction mixture was then diluted with EtOAc and washed with saturated NaHCO$_3$ solution. The aqueous layer was extracted with EtOAc. The organic layers were combined, dried, filtered and concentrated under reduced pressure. The crude compound was purified by preparative MS/HPLC to afford a mixture of diastereoisomers.

Compound 7: Mixture of Diastereoisomers 7A/7B: $^{31}$P NMR (DMSO-$d_6$, 162 MHz) δ (ppm) −7.12 (s, 0.5P), −9.09 (s, 0.5P); MS (ESI) m/z=474.6 (MH$^+$).

The mixture of diastereoisomers was separated by preparative chiral SFC (CHIRALPAK-AD-H, 20*150 mm; Mobile Phase A: 20% IPA; Mobile Phase B CO$_2$) to afford the 2 expected separated diastereoisomers:

Compound 7 Diastereoisomer 1: $^1$H NMR (DMSO-$d_6$, 400 MHz) δ (ppm) 8.01 (s, 1H), 6.49 (s, 2H), 5.56 (s, 2H), 4.47-4.34 (m, 5H), 4.08-3.96 (m, 4H), 3.81 (m, 1H), 2.61-2.54 (m, 1H), 1.98-1.92 (m, 1H), 1.75-1.69 (m, 1H), 1.37-1.34 (m, 3H), 1.19-1.16 (m, 3H), 1.11-1.03 (m, 3H); $^{31}$P NMR (DMSO-$d_6$, 162 MHz) δ (ppm) −9.08 (s, 1P).

Compound 7 Diastereoisomer 2: $^1$H NMR (DMSO-$d_6$, 400 MHz) δ (ppm) 8.02 (s, 1H), 6.50 (s, 2H), 5.54 (s, 2H), 4.47-4.38 (m, 4H), 4.23-4.17 (m, 2H), 4.06-3.95 (m, 4H), 1.93-1.86 (m, 1H), 1.69-1.62 (m, 1H), 1.37-1.34 (m, 3H), 1.17-1.14 (m, 3H), 1.07-1.03 (m, 3H); $^{31}$P NMR (DMSO-$d_6$, 162 MHz) δ (ppm) −7.11 (s, 1P).

Example 8

Preparation of Compounds 8A and 8B

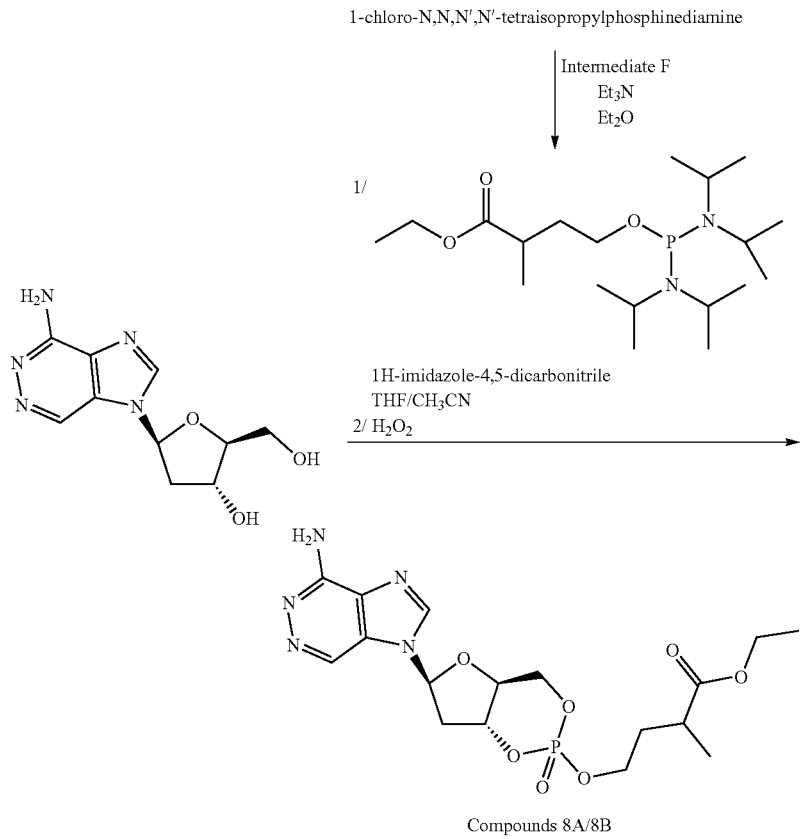

Compounds 8A/8B: Ethyl 4-(((2R,4aS,6S,7aR)-6-(6-amino-9H-purin-9-yl)-2-oxidotetrahydro-4H-furo[3,2-d][1,3,2]dioxaphosphinin-2-yl)oxy)-2-methylbutanoate and Ethyl 4-(((2S,4aS,6S,7aR)-6-(6-amino-9H-purin-9-yl)-2-oxidotetrahydro-4H-furo[3,2-d][1,3,2]dioxaphosphinin-2-yl)oxy)-2-methylbutanoate Compounds 8A/8B were synthesized according to a similar procedure than the procedure described for Compounds 3A/3B using (2S,3R,5S)-5-(6-amino-9H-purin-9-yl)-2-(hydroxymethyl)tetrahydrofuran-3-ol and Intermediate F as starting materials.

Compound 8: Mixture of Diastereoisomers 8A/8B: $^1$H NMR (DMSO-d$_6$, 400 MHz) δ (ppm) 8.40 (s, 0.2H), 8.36-8.35 (m, 0.8H), 8.19 (s, 0.2H), 8.16 (m, 0.8H), 7.36 (brs, 2H), 6.52-6.47 (m, 1H), 5.47-5.36 (m, 1H), 4.65-4.56 (m, 1H), 4.43-4.27 (m, 1H), 4.18-3.99 (m, 5H), 2.83-2.66 (m, 3H), 2.13-1.93 (m, 1H), 1.87-1.69 (m, 1H), 1.22-1.12 (m, 6H); $^{31}$P NMR (DMSO-d$_6$, 162 MHz) δ (ppm) −4.86 (s, 0.1P), −4.88 (s, 0.1P), −6.60 (s, 0.8P); MS (ESI) m/z=442.3 (MH$^+$).

Example 9

Preparation of Compounds 9A1, 9A2, 9B1 and 9B2

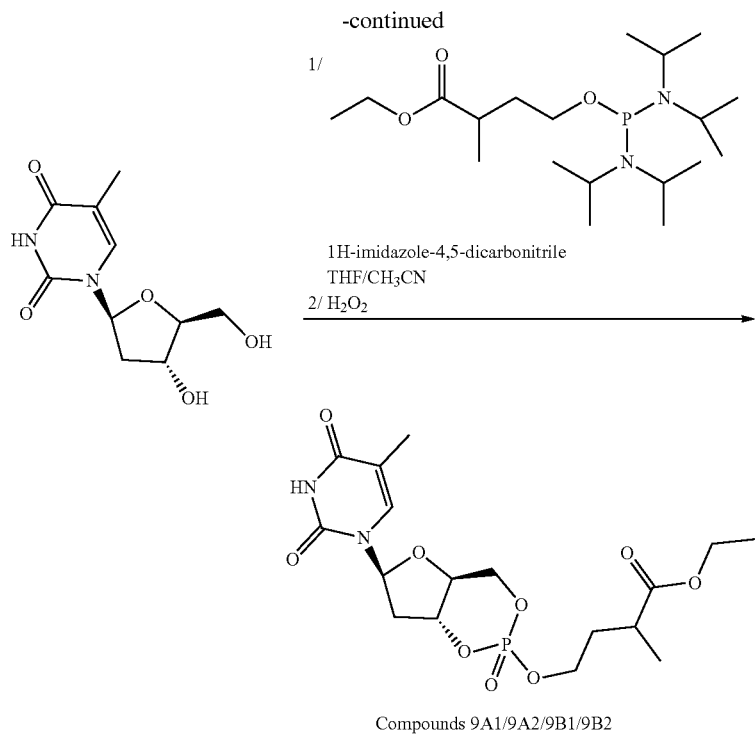

Compounds 9A1/9A2/9B1/9B2

Compounds 9A1/9A2/9B1/9B2: Ethyl (S)-2-methyl-4-(((2R,4aS,6S,7aR)-6-(5-methyl-2,4-dioxo-3,4-dihydropyrimidin-1(2H)-yl)-2-oxidotetrahydro-4H-furo[3,2-d][1,3,2]dioxaphosphinin-2-yl)oxy)butanoate, Ethyl (R)-2-methyl-4-(((2R,4aS,6S,7aR)-6-(5-methyl-2,4-dioxo-3,4-dihydropyrimidin-1(2H)-yl)-2-oxidotetrahydro-4H-furo[3,2-d][1,3,2]dioxaphosphinin-2-yl)oxy)butanoate, Ethyl (S)-2-methyl-4-(((2S,4aS,6S,7aR)-6-(5-methyl-2,4-dioxo-3,4-dihydropyrimidin-1(2H)-yl)-2-oxidotetrahydro-4H-furo[3,2-d][1,3,2]dioxaphosphinin-2-yl)oxy)butanoate and Ethyl (R)-2-methyl-4-(((2S,4aS,6S,7aR)-6-(5-methyl-2,4-dioxo-3,4-dihydropyrimidin-1(2H)-yl)-2-oxidotetrahydro-4H-furo[3,2-d][1,3,2]dioxaphosphinin-2-yl)oxy)butanoate Compounds 9A1/9A2/9B1/9B2 were synthesized according to a similar procedure than the procedure described for Compounds 3A/3B using 1-((2S,4R,5S)-4-hydroxy-5-(hydroxymethyl)tetrahydrofuran-2-yl)-5-methylpyrimidine-2,4(1H,3H)-dione and Intermediate F as starting materials.

Compound 9: Mixture of Diastereoisomers 9A1/9A2/9B1/9B2: $^1$H NMR (DMSO-$d_6$, 400 MHz) δ (ppm) 11.42 (s, 0.8H), 11.39 (s, 0.2H), 7.58 (s, 0.2H), 7.51 (s, 0.8H), 6.38-6.29 (m, 1H), 4.77 (q, J=9.06 Hz, 1H), 4.64-4.55 (m, 1H), 4.50-4.33 (m, 1H), 4.13-4.06 (m, 4H), 3.93-3.87 (m, 1H), 2.68-2.54 (m, 2H), 2.49-2.41 (m, 1H), 2.08-1.93 (m, 1H), 1.85-1.70 (m, 4H), 1.21-1.11 (m, 6H); $^{31}$P NMR (DMSO-$d_6$, 162 MHz) δ (ppm) -4.92 (s, 0.1P), -4.95 (s, 0.1P), -6.66 (s, 0.8P); MS (ESI) m/z=455.2 (MNa$^+$).

The mixture of diastereoisomers was separated by preparative chiral SFC to afford the 4 expected separated diastereoisomers:

Compound 9 Diastereoisomer 1: $^{31}$P NMR (DMSO-$d_6$, 162 MHz) δ (ppm) -4.94 (s, 1P).

Compound 9 Diastereoisomer 2: $^{31}$P NMR (DMSO-$d_6$, 162 MHz) δ (ppm) -4.91 (s, 1P).

Compound 9 Diastereoisomer 3: $^{31}$P NMR (DMSO-$d_6$, 162 MHz) δ (ppm) -6.66 (s, 1P).

Compound 9 Diastereoisomer 4: $^{31}$P NMR (DMSO-$d_6$, 162 MHz) δ (ppm) -6.66 (s, 1P).

Example 10

Preparation of Compound 10

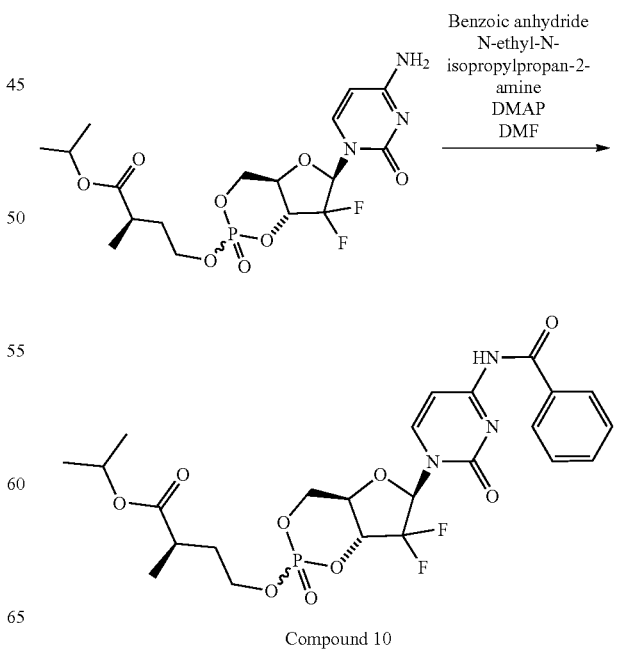

Compound 10

Compound 10: Isopropyl (2R)-4-(((4aR,6R,7aR)-6-(4-benzamido-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate To a solution of isopropyl (2R)-4-(((4aR,6R,7aR)-6-(4-amino-2-oxopyrimidin-1(2H)-yl)-7,7-difluoro-2-oxidotetrahydro-4H-furo[3,2-d][1,3,2]dioxaphosphinin-2-yl)oxy)-2-methylbutanoate (650 mg, 1.39 mmol), in DMF (4.6 mL), were added N-ethyl-N-isopropylpropan-2-amine (630 μL, 3.62 mmol), benzoic anhydride (440 mg, 1.95 mmol) and DMAP (51 mg, 0.42 mmol). The reaction mixture was stirred at RT for 3 hours. The crude compound was purified by preparative MS/HPLC to afford the title compound. $^1$H NMR (DMSO-d$_6$, 400 MHz) δ (ppm) 11.51 (brs, 1H), 8.31 (d, J=7.53 Hz, 1H), 8.03-8.01 (m, 2H), 7.67-7.63 (m, 1H), 7.56-7.52 (m, 2H), 7.44-7.43 (m, 1H), 6.48 (brs, 1H), 5.06 (brs, 1H), 4.90 (heptuplet, J=6.33 Hz, 1H), 4.83-4.74 (m, 1H), 4.65-4.60 (m, 1H), 4.44-4.38 (m, 1H), 4.21-4.13 (m, 2H), 2.63-2.55 (m, 1H), 2.09-2.01 (m, 1H), 1.85-1.77 (m, 1H), 1.19 (d, J=6.33 Hz, 3H), 1.185 (d, J=6.33 Hz, 3H), 1.13 (d, J=7.06 Hz, 3H); $^{31}$P NMR (DMSO-d$_6$, 162 MHz) δ (ppm) −7.50 (s, 1P); $^{19}$F NMR (DMSO-d$_6$, 376 MHz) δ (ppm) −115.93-(−117.39) (m, 2F); MS (ESI) m/z=572.5 (MH$^+$).

Example 11

Preparation of Compounds 11A and 11B

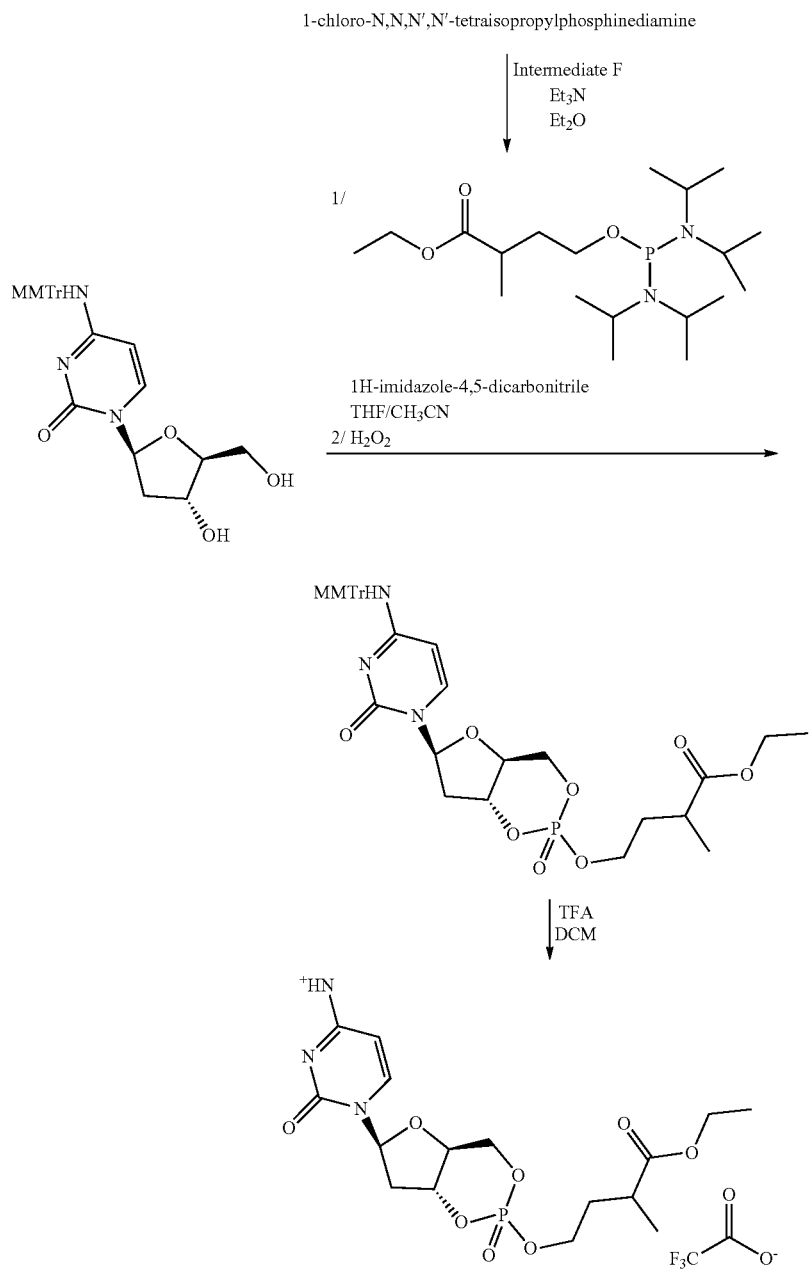

Compounds 11A/11B

Compounds 11A/11B: Ethyl 4-(((2R,4aS,6S,7aR)-6-(4-amino-2-oxopyrimidin-1(2H)-yl)-2-oxidotetrahydro-4H-furo[3,2-d][1,3,2]dioxaphosphinin-2-yl)oxy)-2-methylbutanoate and ethyl 4-(((2S,4aS,6S,7aR)-6-(4-amino-2-oxopyrimidin-1(2H)-yl)-2-oxidotetrahydro-4H-furo[3,2-d][1,3,2]dioxaphosphinin-2-yl)oxy)-2-methylbutanoate (TFA Salts)

Compounds 11A/11B were synthesized according to a similar procedure than the procedure described for Compounds 3A/3B using 1-((2S,4R,5S)-4-hydroxy-5-(hydroxymethyl)tetrahydrofuran-2-yl)-4-(((4-methoxyphenyl)diphenylmethyl)amino)pyrimidin-2(1H)-one and Intermediate F as starting materials.

Compound 11: Mixture of Diastereoisomers 11A/11B: $^1$H NMR (DMSO-$d_6$, 400 MHz) δ (ppm) 8.52 (s, 1H), 8.07 (s, 1H), 7.85 (d, J=7.59 Hz, 1H), 6.27-6.23 (m, 1H), 5.93 (d, J=7.59 Hz, 1H), 4.72-4.58 (m, 2H), 4.40 (t, J=10.05 Hz, 1H), 4.12-4.05 (m, 4H), 3.98-3.92 (m, 1H), 2.65-2.54 (m, 2H), 2.46-2.41 (m, 1H), 2.07-1.98 (m, 1H), 1.83-1.74 (m, 1H), 1.21-1.17 (m, 3H), 1.14 (d, J=7.10 Hz, 3H); $^{31}$P NMR (DMSO-$d_6$, 162 MHz) δ (ppm) −4.83 (s, 0.1P), −6.71 (s, 0.9P); MS (ESI) m/z=418.3 (MH$^+$).

Example 12

In Vitro Inhibition

The compounds of the invention were tested in cell based in vitro assays comprising HuH-1 cells and HepG2 cells, as in vitro models for potential hepatocellular carcinoma activity.
HuH-1 cells were purchased from JCRB, HepG2 cells from ATCC, and both tested with the following method:
Day 1:
Cells are suspended at a specific density in a specific culture medium. Then, 100 μl of cell suspension are plated per well in 96-well plates.
Day 2:
Compounds or negative controls (DMSO) are added to the cells (100p of a compound solution in its specific medium with a final concentration of 0.15% DMSO).
Each compound concentration is tested in duplicate (6 concentrations per compound).
Cells are incubated at 37° C. for 72 h without treating again.
Day 4:
SDS is added to control wells (final concentration of 1%) and kept for 15 min at 37° C. SDS 1% represents the positive control of proliferation inhibition.
Cell supernatant is removed and 100 μl of a MTT (3-[4.5-dimethylthiazol-2-yl]-2.5-diphenyltetrazolium bromide) solution in fresh medium are added per well (MTT final concentration of 0.5 mg/ml) and incubated for 4 h at 37° C. MTT reaction is stopped and homogenized by adding 100p/well of SDS 10%, 0.01M HCl and incubated for 2 h at 37° C.
Absorbance is measured at 570 nm.
The results for selected compounds are shown in Table 1.

TABLE 1

In vitro inhibition of HuH-1 and HepG2:

| Compound | HuH-1: Relative IC50 | HepG2: Relative IC50 |
|---|---|---|
| 1 Diastereoisomer 1 | A | ND |
| 2 Diastereoisomer 1 | A | ND |
| 2 Diastereoisomer 2 | A | B |
| 3 Diastereoisomer 1 | B | A |

TABLE 1-continued

In vitro inhibition of HuH-1 and HepG2:

| Compound | HuH-1: Relative IC50 | HepG2: Relative IC50 |
|---|---|---|
| Mixture 5A/5B | C | C |
| Mixture 6A/6B | C | C |

The IC$_{50}$ values in Table 1 are as follows:
A=<0.5 μM
B=≥0.5 μM and <5 μM
C=≥5 μM Example 13

In Vitro Conversion of Prodrug to Nucleoside Triphosphate

The degree of conversion of a prodrug compound of the present invention to its corresponding nucleoside triphosphate (NTP) can be measured in vitro using the procedure described below.

A 2 mM stock solution of the prodrug test compound is prepared in 5% DMSO/95% MeOH to provide a final sample concentration of 10 μM. A 5 μL aliquot is removed from this stock solution and added to 1 mL of either a rat or human cryopreserved hepatocyte sample to provide a control sample at concentration of 1 million cells/mL. This sample is assayed in triplicate and used as a test sample.

A 2 mM stock solution of (2R,3R,4R,5R)-2-(4-amino-7H-pyrrolo[2,3-d]pyrimidin-7-yl)-5-(hydroxymethyl)-3-methyltetrahydrofuran-3,4-diol is prepared in 5% DMSO/95% MeOH to provide a final sample concentration of 10 μM.

A 5 μL aliquot is removed from this stock solution and added to 1 mL of either a rat or human cryopreserved hepatocyte sample to provide a control sample at a concentration of 1 million cells/mL. This sample is assayed in triplicate and used as a control standard.

Human and rat hepatocytes are removed from liquid nitrogen storage and thawed by submerging the hepatocyte tube into a pre-heated 37° C. waterbath and gently shaking the tube back & forth until thawed. The thawed hepatocytes are then gently poured into a container of Hepatocyte Basal Medium (50 mL, pre-warmed to 37° C.) and washed. The hepatocyte tube is then rinsed out with pre-warmed Hepatocyte Basal Medium and the washed hepatocytes and rinse are combined and centrifuged at 500 rpm for 4 minutes at room temperature. The supernatant is then discarded and the resulting hepatocyte pellet is resuspended with Hepatocyte Basal Medium (pre-warmed to 37° C.) and the final hepatocyte concentration is adjusted to 1 million cells/mL to provide the final hepatocyte suspension.

A 1 mL aliquot is removed from the 1 million cells/mL final hepatocyte suspension, analyzed in triplicate and placed into 20 mL scintillation vial without a cap. 2 mM of the prodrug test sample is then added into the hepatocyte suspension to provide a 10 μM final concentration in the 1 mL hepatocyte sample. The sample is then incubated at 37° C./5% CO$_2$ for 4 hours. A blank hepatocyte sample as well as the control standard are also incubated in this fashion.

The incubated hepatocyte suspension samples are transferred to a microcentrifuge tube using a transfer pipette and centrifuged at 500 rpm for 4 minutes at room temperature. The supernatant is discarded and the resulting hepatocyte pellet was resuspended and the cells are extracted with 0.25 mL of a 4° C. solution of 70% methanol/30%(20 mM EDTA/20 mM EGTA) that has been adjusted to pH 8 using sodium hydroxide. The resulting extract solution is then stored in a refrigerator at 4° C. until ready for use, at which point the sample is first subjected to vortexing/sonication to ensure that all hepatocyte cells have burst. The sample is then centrifuged at 4000 rpm for 10 minutes at 4° C. and a 100 µL aliquot of the resulting supernatant is added into a bioanalytical plate (2 mL Square 96 well plate w/100 uL Tapered Reservoir), with the remaining supernatant immediately stored at −80° C. for re-assay if necessary. The blank control supernatant is transferred to a new tube for use as a control matrix in standard curves.

Alternatively, cryopreserved plateable hepatocytes are obtained from Celsis-In Vitro Technologies (Baltimore, Md.) and plated according to manufacturer's protocol at $0.7 \times 10^6$ cells/mL in In Vitro GRO CP Medium ($1.75 \times 10^6$ cells/well in 6-well plates) three hours prior to inhibitor treatment. An inhibitor in DMSO at the indicated concentration in In Vitro GRO CP Medium is added to the hepatocytes at t=0. At indicated times up to 48 hours post dosing, cells are washed in ice-cold PBS, extracted with ice-cold 1 mL 70% methanol: 30% 20 mM EDTA/EGTA and centrifuged. The supernatant is stored at −80° C. until analysis. For intracellular NTP analysis, an NTP calibration curve is first generated by spiking a blank extraction buffer with known concentrations of the NTP standard. LC/ESI-MS analysis is performed on a QTRAP 5500 LC/MS/MS system (Applied Biosystems, Foster City, Calif.) coupled to a Shimazu UFLC system, operated in the positive-ion mode. The HPLC system is consisted of solvent delivery module (LC20-AD XR), auto injector (SIL-20ACXR), and photo-diode array detector (SPD-M20A PDA) (Shimazu Corporation, Tokyo, Japan). All HPLC separations are performed at 40° C. The test samples are analyzed on a BioBasic AX column (5 µm particle size, 100×2.1 mm I.D., Thermo Scientific) using A (Acetonitrile: 10 mM NH$_4$Ac=30:70, v:v, pH=6) and B (Acetonitrile: 1 mM NH$_4$Ac=30:70, v:v, pH=10) as mobile phases at a flow rate of 1.0 mL/min. The injection volume is 50 µL. The mobile phase gradient starts at 0% B, and linearly increases to 100% B over 6 min. The MS analysis of all NTPs is performed on the same QTRAP 5500 MS instrument in the multiple ion monitoring mode (MRM), with Turbo-Ion-Spray ionization. The collision energy is 40 eV for all the analytes and standards. The quadrupole mass analyzer is set to unit resolution.

The results for selected compounds are shown in Table 2:

TABLE 2

| In vitro NTP in Human Hepatocytes: | |
|---|---|
| Compound | Human Hepatocyte 1 hour at 10 µM, NTP |
| 2 Diastereoisomer 2 | A |
| 1 Diastereoisomer 2 | A |
| 10 | C |

The NTP values in Table 2 are as follows:

A=<0.5 µM

B=≥0.5 µM and <1 µM

C=≥1 µM

The invention claimed is:

1. A compound according to Formula I or Formula II:

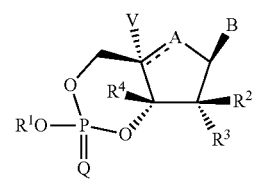

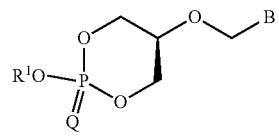

or a pharmaceutically acceptable salt or stereoisomer thereof wherein:

A is selected from O, S, CH$_2$, CF and C=CH$_2$, such that if R$^2$ is OH and R$^3$, R$^4$ and V are hydrogen, then A is other than S; and if A is CF or C=CH$_2$, then V is absent;

B is selected from the following groups:

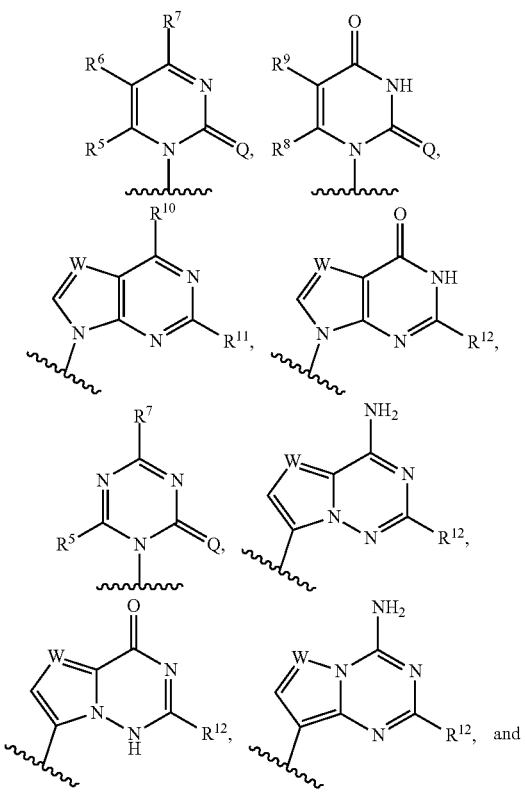

-continued

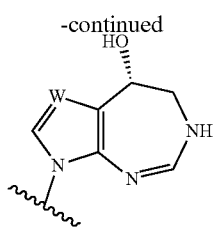

each Q is independently O or S;
V is hydrogen, halogen, —N(R$^{13}$)$_2$, —OR$^{13}$, alkyl, alkenyl, alkynyl, haloalkyl, N$_3$ or CN;
W is N, CH or CF;
R$^1$ is —CH$_2$—X—Y—R$^{16}$;
X is —C(R$^{14}$)$_2$;
Y is —C(R$^{15}$)$_2$, or C$_3$-C$_6$ cycloalkylene;
R$^2$ is fluoro, chloro, —OR$^{13}$, —CN, —N(R$^{13}$)$_2$, N$_3$, C$_1$-C$_3$alkyl, C$_1$-C$_3$haloalkyl, C$_2$-C$_6$alkenyl or C$_2$-C$_3$alkynyl;
R$^3$ is hydrogen;
R$^4$ is hydrogen, C$_1$-C$_6$alkyl, C$_2$-C$_6$alkenyl, C$_2$-C$_6$alkynyl, C$_1$-C$_6$haloalkyl, —OR$^{13}$, fluoro, chloro, N$_3$, —CN or —N(R$^{13}$)$_2$;
R$^5$, R$^6$, R$^8$ and R$^9$ are each independently selected from hydrogen, C$_1$-C$_6$alkyl, C$_1$-C$_6$haloalkyl, C$_1$-C$_6$hydroxyalkyl, halogen, —OR$^{18}$, —SR$^{18}$ and —N(R$^{18}$)$_2$;
R$^7$, R$^{10}$, R$^{11}$ and R$^{12}$ are each independently selected from hydrogen, C$_1$-C$_6$alkyl, C$_2$-C$_6$ alkenyl, C$_2$-C$_6$alkynyl, C$_3$-C$_7$cycloalkyl, C$_5$-C$_6$heteroaryl, C$_9$-C$_{10}$heteroaryl, halogen, —OR$^{18}$, —SR$^{18}$, —S(O)R$^{18}$, —S(O)$_2$R$^{18}$, —S(O)$_2$N(R$^{18}$)$_2$, —NHC(O)OR$^{18}$, —NHC(O)N(R$^{18}$)$_2$, C$_1$-C$_6$haloalkyl, C$_1$-C$_6$hydroxyalkyl, —O(C$_1$-C$_6$haloalkyl), —CN, —NO$_2$, —N(R$^{18}$)$_2$, —NH(C$_1$-C$_6$alkylene)-(C$_5$-C$_6$heteroaryl), —NH(C$_1$-C$_6$ alkylene)-(C$_9$-C$_{10}$heteroaryl), —C(O)R$^{18}$, —C(O)OR$^{18}$, —C(O)N(R$^{18}$)$_2$ and —NHC(O)R$^{18}$, wherein said C$_2$-C$_6$alkenyl group and said C$_2$-C$_6$alkynyl group are optionally substituted with one or more halogen;
each occurrence of R$^{13}$ is independently selected from hydrogen, C$_1$-C$_6$alkyl —C(O)R$^{18}$, or —C(O)OR$^{18}$;
R$^{14}$ is hydrogen, halogen, C$_1$-C$_6$alkyl, C$_1$-C$_6$haloalkyl, C$_1$-C$_6$hydroxyalkyl, C$_6$-C$_{10}$aryl-, OR$^{17}$, —OC(O)R$^{17}$, —N(R$^{12}$)C(O)OR$^{17}$ or —C(O)OR$^{17}$;
each occurrence of R$^{15}$ is independently selected from hydrogen, halogen, C$_1$-C$_6$alkyl, C$_1$-C$_6$haloalkyl, C$_1$-C$_6$hydroxyalkyl, C$_6$-C$_{10}$aryl-, OR$^{17}$, —OC(O)R$^{17}$, —N(R$^{12}$)C(O)OR$^{17}$ and —C(O)OR$^{17}$ or both R$^{15}$ groups together with the carbon atom to which they are attached can join to form a 3- to 6-membered spirocyclic cycloalkyl group, such that at least one R$^{15}$ group cannot be hydrogen;
R$^{16}$ is —C(O)OR$^{17}$;
each occurrence of R$^{17}$ is independently selected from hydrogen, halogen, C$_1$-C$_6$alkyl, C$_7$cycloalkyl and C$_6$-C$_{10}$aryl;
each occurrence of R$^{18}$ is independently selected from hydrogen, C$_1$-C$_{15}$alkyl, C$_1$-C$_6$haloalkyl, C$_1$-C$_6$hydroxyalkyl, —(C$_1$-C$_3$alkylene)$_m$-(C$_3$-C$_7$cycloalkyl), —(C$_1$-C$_3$alkylene)$_m$-(C$_6$-C$_{10}$aryl), —(C$_1$-C$_3$alkylene)$_m$-(C$_4$-C$_7$heterocycloalkyl), —(C$_1$-C$_3$alkylene)$_m$-(C$_5$-C$_6$heteroaryl) and —(C$_1$-C$_3$alkylene)$_m$-(C$_9$-C$_{10}$heteroaryl); and
each occurrence of m is independently 0 or 1.
2. The compound of claim 1 wherein A is O or S.

3. The compound of claim 1, wherein R$^1$ is

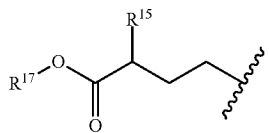

and wherein R$^{15}$ and R$^{17}$ are each independently selected from C$_1$-C$_6$alkyl.
4. The compound of claim 1, wherein R$^2$ is fluoro or hydroxyl.
5. The compound of claim 1, wherein R$^4$ is hydrogen.
6. The compound of claim 1, wherein V is hydrogen.
7. The compound of claim 1, wherein B is

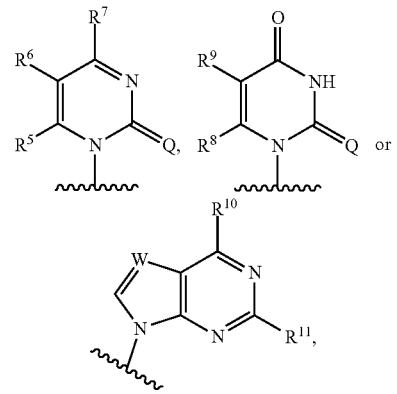

wherein
Q is O;
W is N;
R$^5$ and R$^6$ are hydrogen;
R$^7$ is NH$_2$ or —NHC(O)—(C$_6$-C$_{10}$ aryl);
R$^8$ is hydrogen;
R$^9$ is hydrogen or trifluoromethyl;
R$^{10}$ is —NH$_2$ or —O—C$_1$-C$_6$alkyl and
R$^{11}$ is —NH$_2$ or halogen.
8. A compound selected from the following:

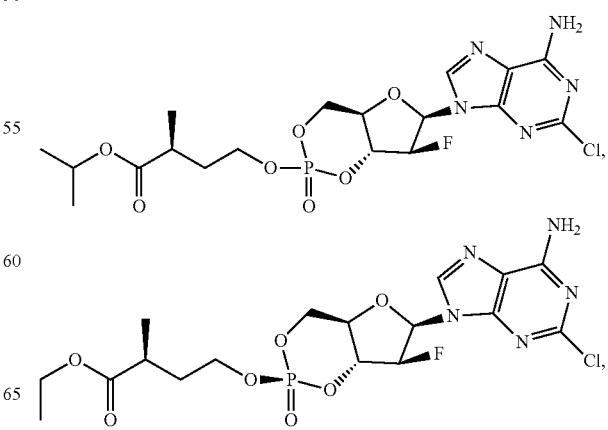

91
-continued
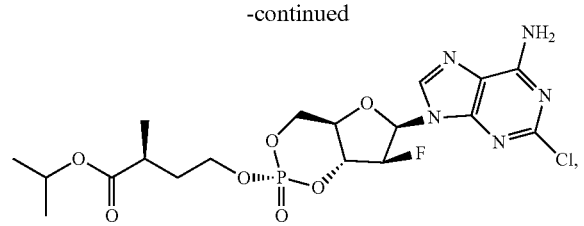
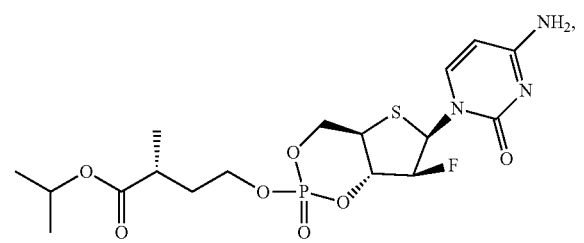
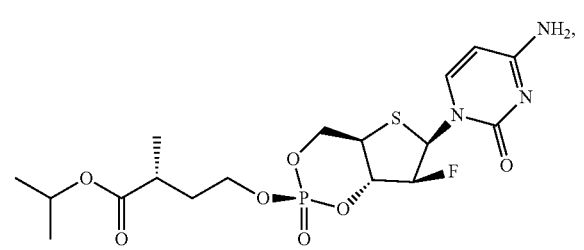
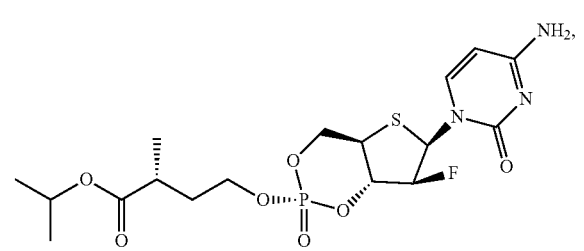
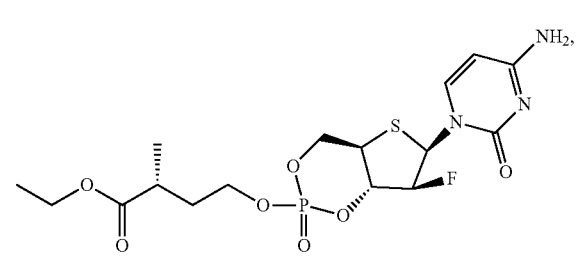
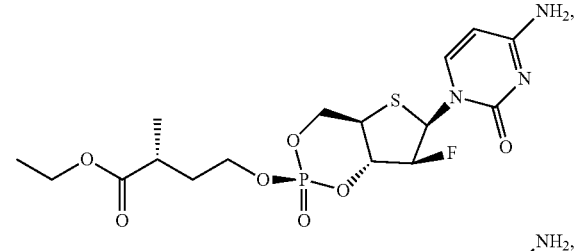
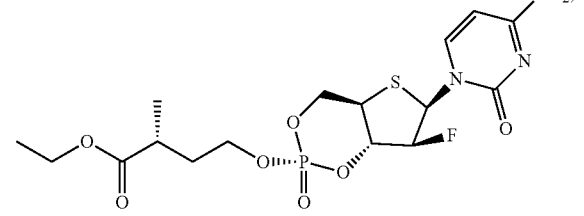
92
-continued
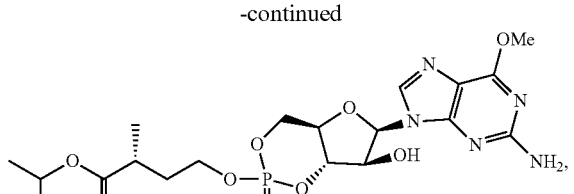
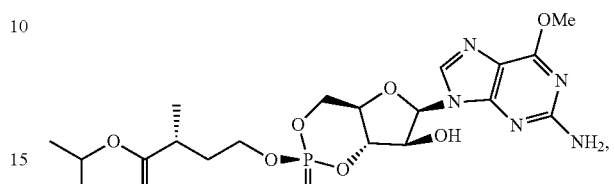
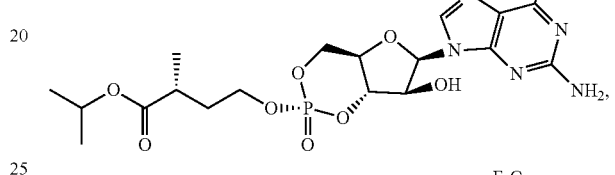
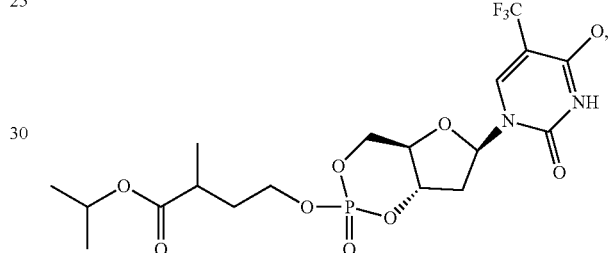
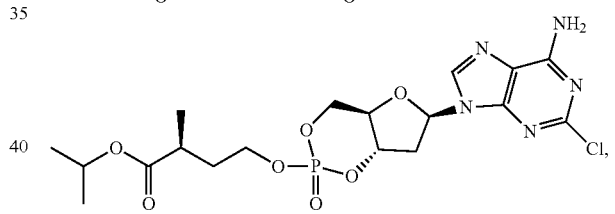
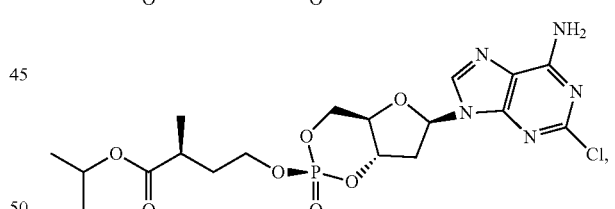
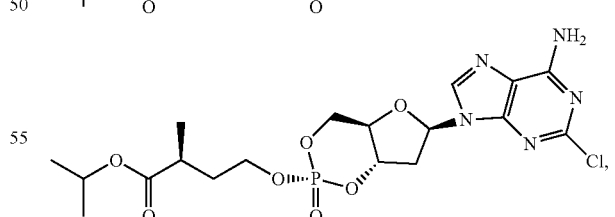
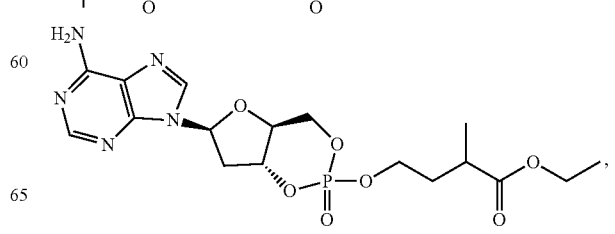

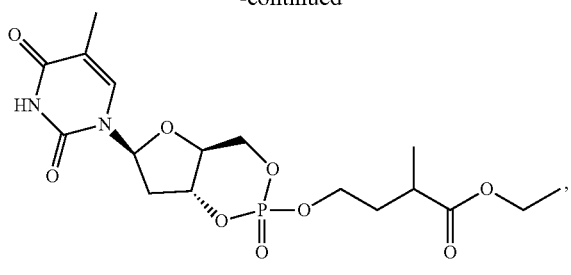

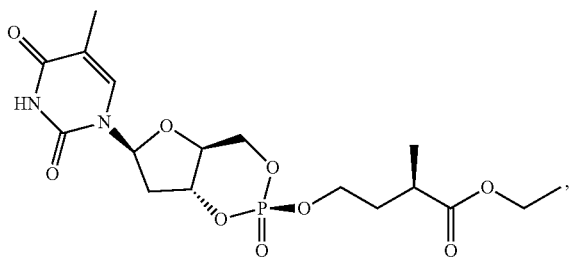

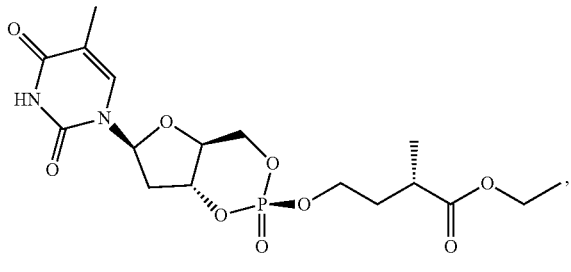

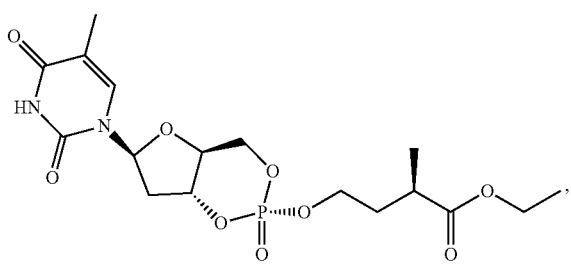

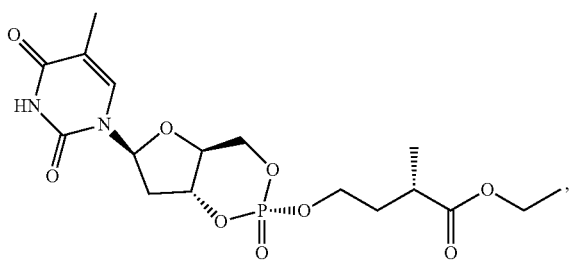

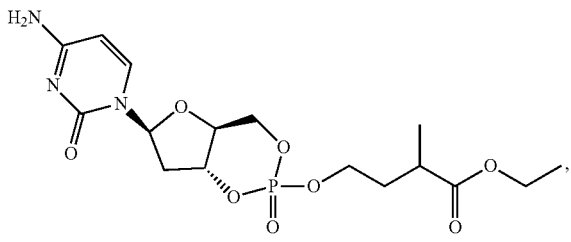

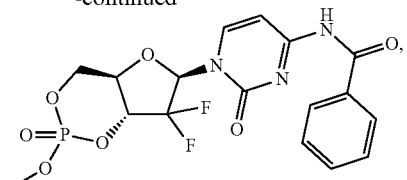

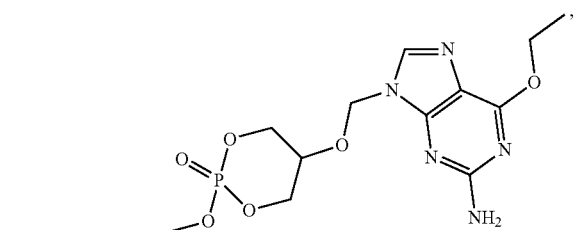

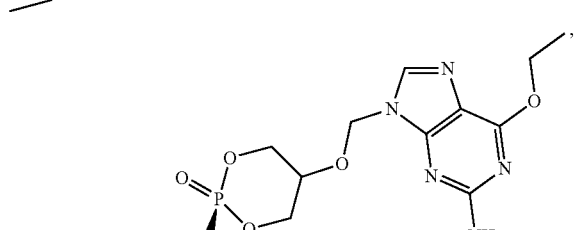

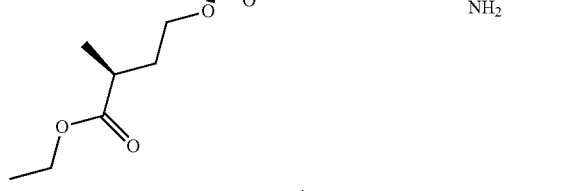

and

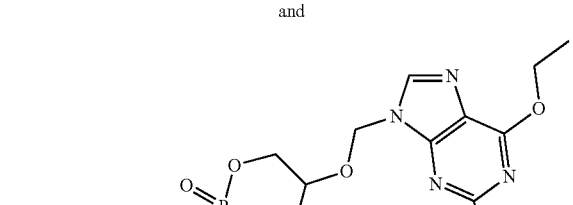

or a pharmaceutically acceptable salt thereof.

9. A pharmaceutical composition comprising a compound of claim 1, or a pharmaceutically acceptable salt or stereoisomer thereof, and a pharmaceutically acceptable carrier or diluent.

10. A method for treating a liver disease in a patient, the method comprising administering to the patient a compound of claim 1, or a pharmaceutically acceptable salt or stereoisomer thereof, wherein said liver disease is hepatocellular carcinoma, or HBV infection.

11. A method for treating Ebola virus infection in a patient, the method comprising administering to the patient a compound of claim 1, or a pharmaceutically acceptable salt or stereoisomer thereof.

\* \* \* \* \*